US012638454B2

(12) United States Patent
Peterson et al.

(10) Patent No.: US 12,638,454 B2
(45) Date of Patent: May 26, 2026

(54) METHODS FOR DETECTING A FOOD SPECIFIC IMMUNE RESPONSE

(71) Applicant: University of Utah Research Foundation, Salt Lake City, UT (US)

(72) Inventors: Kathryn A. Peterson, Salt Lake City, UT (US); Gerald J. Gleich, Salt Lake City, UT (US); Mark D. Yandell, Salt Lake City, UT (US); Edwin Lin, Salt Lake City, UT (US); Hedieh Saffari, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 1009 days.

(21) Appl. No.: 17/767,250

(22) PCT Filed: Oct. 8, 2020

(86) PCT No.: PCT/US2020/054819
§ 371 (c)(1),
(2) Date: Apr. 7, 2022

(87) PCT Pub. No.: WO2021/072103
PCT Pub. Date: Apr. 15, 2021

(65) Prior Publication Data
US 2022/0373560 A1 Nov. 24, 2022

Related U.S. Application Data

(60) Provisional application No. 62/912,505, filed on Oct. 8, 2019.

(51) Int. Cl.
*G01N 33/02* (2006.01)
*G01N 33/68* (2006.01)

(52) U.S. Cl.
CPC ..... *G01N 33/6854* (2013.01); *G01N 2800/06* (2013.01); *G01N 2800/24* (2013.01)

(58) Field of Classification Search
CPC .......... G01N 33/6854; G01N 2800/06; G01N 2800/24; G01N 2333/415;
(Continued)

(56) References Cited

U.S. PATENT DOCUMENTS

| | | | |
|---|---|---|---|
| 6,858,398 B2 | 2/2005 | Vojdani | |
| 8,802,375 B2 * | 8/2014 | Sampson | ........... G01N 33/6854 435/7.1 |
| 2015/0132221 A1 * | 5/2015 | Pease | ..................... A61K 51/08 424/1.73 |

FOREIGN PATENT DOCUMENTS

| | | |
|---|---|---|
| AU | 2020363878 | 10/2020 |
| CA | 3154110 | 10/2020 |

(Continued)

OTHER PUBLICATIONS

H Agata, N Kondo, O Fukutomi, S Shinoda, T Orii, Effect of elimination diets on food-specific IgE antibodies and lymphocyte proliferative responses to food antigens in atopic dermatitis patients exhibiting sensitivity to food allergens, J of Allergy and Clin Immun, vol. 91, Issue 2, pp. 668-679, (Year: 1993) .*

(Continued)

*Primary Examiner* — Gregory S Emch
*Assistant Examiner* — Michael Cameron Sveiven
(74) *Attorney, Agent, or Firm* — BALLARD SPAHR LLP

(57) ABSTRACT

Disclosed are methods of diagnosing and treating a subject with active or inactive eosinophilic esophagitis (EoE). The methods may include the steps of detecting whether a level of one or more immunoglobulin antibodies is elevated in an esophageal secretion sample obtained from a subject, diagnosing the subject with active EoE when the level of one or more immunoglobulin antibodies in the sample is elevated
(Continued)

above a pre-determined cut-off value and diagnosing the subject with inactive EoE when the level of one or more immunoglobulin antibodies level in the sample is below a pre-determined cut-off value; and treating the subject diagnosed with active EoE.

17 Claims, 17 Drawing Sheets

(58) Field of Classification Search
CPC ....... G01N 2333/435; G01N 2333/465; G01N 2333/4731; G01N 33/6893; G01N 33/686; G01N 33/02; A61P 37/08
See application file for complete search history.

(56) References Cited

FOREIGN PATENT DOCUMENTS

| | | | | |
|---|---|---|---|---|
| EP | 2732288 B1 * | 7/2017 | ....... | G01N 33/54386 |
| EP | 20875355.8 | 10/2020 | | |
| JP | 2017-511478 A | 10/2015 | | |
| JP | 2022-521560 | 10/2020 | | |
| KR | 10-2022-7014939 | 10/2020 | | |

OTHER PUBLICATIONS

F Clayton, JC Fang, GJ Gleich, AJ Lucendo, JM Olalla, LA Vinson, A Lowichik, X Chen, L Emerson, K Cox, MA O'Gorman, KA Peterson, Eosinophilic Esophagitis in Adults Is Associated With IgG4 and Not Mediated by IgE, Gastroenterology, vol. 147, Issue 3, 2014, pp. 602-609, ISSN 0016-5085 (Year: 2014).*
Gleich GJ, Yunginger JW. The radioallergosorbent test: a method to measure IgE antibodies, IgG blocking antibodies, and the potency of allergy extracts. Bull N Y Acad Med. Sep. 1981;57(7):559-67. PMID: 6944131; PMCID: PMC1805262. (Year: 1981).*
Zar, Sameer M.R.C.P.; Benson, Martin J. M.D., F.R.C.P.; Kumar, Devinder Ph.D., F.R.C.S.. Food-Specific Serum IgG4 and IgE Titers to Common Food Antigens in Irritable Bowel Syndrome. American Journal of Gastroenterology 100(7):p. 1550-1557, Jul. 2005. (Year: 2005).*
Y. Y. Chua, M.D., K. Bremner, BSc., J. 1. Llobet, M.D., H. 1. Kokubu, and C. Collins-Williams, M.D. "Diagnosis of food allergy by the radioallergosorbent test". J. Allergy Clin. Immunol. vol. 58, No. 4, pp. 477-482. (Year: 1976).*
Dellon ES et al., "Sa1154—an Allergen-Specific Immune Signature Identifies Food Triggers in Eosinophilic Esophagitis with High Accuracy", Gastroenterology, vol. 154, No. 6, May 2018.
Dellon ES et al., "Sa1155—A Novel Allergen-Specific Immune Signature-Directed Approach to Dietary Elimination Therapy Has Efficacy in Adults with Eosinophilic Esophagitis: A Prospective Clinical Study", Gastroenterology, Elsevier Inc, US, vol. 154, No. 6, May 1, 2018 (May 1, 2018), XP085389906.
Erwin EA et al., "Serum IgE measurement and detection of food allergy in pediatric patients with eosinophilic esophagitis", Annals of Allergy, Asthma, vol. 104, No. 6, Jun. 1, 2010, pp. 496-502.
James et al., "Immunologic changes associated with the development of tolerance in children with cow milk allergy", Journal of Pediatrics, vol. 121, No. 3, Sep. 1992, pp. 371-377.
Kagalwalla AF et al., "Efficacy of a 4-Food Elimination Diet for Children With Eosinophilic Esophagitis", Clinical Gastroenterology and Hepatology, vol. 15, No. 11, Jun. 2017, p. 1698.
Wilson JM et al., "IgG4 Component Allergens Are Preferentially Increased in Eosinophilic Esophagitis As Compared to Patients with Milk Anaphylaxis or Galactose-Alpha-1,3-Galactose Allergy", Journal of Allergy and Clinical Immunology, vol. 137, No. 2.
Aceves SS. Allergy Testing in Patients with Eosinophilic Esophagitis. Gastroenterol Hepatol (N Y) 2016; 12:516-518.

Ahrens N, et al. Immune tolerance induction in patients with IgA anaphylactoid reactions following long-term intravenous IgG treatment. Clin Exp Immunol 2008; 151(3):455-8.
Alexander, ES, et al. Twin and family studies reveal strong environmental and weaker genetic cues explaining heritability of eosinophilic esophagitis. The Journal of Allergy and Clinical Immunology, 134(5):1084-1092.e1, Nov. 2014.
Andreae, DA, et al. Swallowed Fluticasone Propionate Is an Effective Long-Term Maintenance Therapy for Children With Eosinophilic Esophagitis. The American Journal of Gastroenterology, 111(8):1187-1197, Jun. 2016.
Andre C. Letter: Allergy, tolerance, and immunoglobulin A. Lancet 1974; 2:782.
Anyane-Yeboa A, et al. The Role of Allergy Testing in Eosinophilic Esophagitis. Gastroenterol Hepatol (N Y) Aug. 2018; 14(8):463-469.
Arias, A and Lucendo, AJ. Incidence and prevalence of eosinophilic oesophagitis increase continiously in adults and children in Central Spain: A 12-year population-based study. Digestive and Liver Disease, Jan. 2019;51(1):55-62.
Armbruster-Lee, J, et al. Understanding fibrosis in eosinophilic esophagitis: Are we there yet? Journal of Leukocyte Biology, 104(1):31-40, Jul. 2018.
Assa'AD, AH, et al. An antibody against IL-5 reduces numbers of esophageal intraepithelial eosinophils in children with eosinophilic esophagitis. Gastroenterology, 141(5):1593-1604, Nov. 2011.
Assa'AD A. Detection of causative foods by skin prick and atopy patch tests in patients with eosinophilic esophagitis: things are not what they seem. Ann Allergy Asthma Immunol 2005; 95:309-11.
Bjorksten B, et al. Immunoglobulin E and immunoglobulin G4 antibodies to cow's milk in children with cow's milk allergy. Allergy 1983; 38:119-24.
Blanchard, C, et al. IL-13 involvement in eosinophilic esophagitis: transcriptome analysis and reversibility with glucocorticoids. The Journal of Allergy and Clinical Immunology, 120(6):1292-1300, Dec. 2007.
Blanchard, C, et al. Inhibition of human interleukin-13-induced respiratory and oesophageal inflammation by anti-human-interleukin-13 antibody (CAT-354). Clinical and Experimental Allergy, 35(8):1096-1103, Aug. 2005.
Blanchard C, et al. Eosinophilic esophagitis: unclear roles of IgE and eosinophils. J Intern Med 2017; 281:448-457.
Butz, BK, et al. Efficacy, dose reduction, and resistance to high-dose fluticasone in patients with eosinophilic esophagitis. Gastroenterology, 147(2):324-33.e5, Aug. 2014.
Carlier FM, et al. The epithelial barrier and immunoglobulin A system in allergy. Clin Exp Allergy 2016; 46:1372-1388.
Chehade M and Sher E. Medical therapy versus dietary avoidance in eosinophilic esophagitis: Which approach is better? Allergy Asthma Proc 2017; 38:170-176.
Clayton, F, et al., Eosinophilic Esophagitis in Adults is Associated with IgG4 and Not Mediated by IgE. Gastroenterology. Sep. 2014, vol. 147, pp. 602-609.
De Bortoli N, et al. Eosinophilic esophagitis: Update in diagnosis and management. Position paper by the Italian Society of Gastroenterology and Gastrointestinal Endoscopy (SIGE). Dig Liver Dis 2017; 49:254-260.
Dellon, ES, et al. A phenotypic analysis shows that eosinophilic esophagitis is a progressive fibrostenotic disease. Gastrointestinal Endoscopy, 79(4):577-585.e4, 2014.
Dellon, ES; Updated international consensus diagnostic criteria for eosinophilic esophagitis: proceedings of the AGREE conference. Gastroenterology, 155(4):1022-1033.e10, Sep. 2018.
Dellon, ES. Epidemiology of eosinophilic esophagitis. Gastroenterology Clinics of North America, 43(2):201-218, Jun. 2014.
Erwin EA, et al. IgE Antibody Detection and Component Analysis in Patients with Eosinophilic Esophagitis. J Allergy Clin Immunol Pract 2015; 3:896-904 e3.
Fahey LM, et al. Food allergen triggers are increased in children with the TSLP risk allele and eosinophilic esophagitis. Clin Transl Gastroenterol 2018; 9:139.
Fogg, MI, et al. Pollen and eosinophilic esophagitis. The Journal of Allergy and Clinical Immunology, 112(4):796-797, Oct. 2003.

(56)         References Cited

OTHER PUBLICATIONS

Gonsalves N. Dietary Therapy in Eosinophilic Esophagitis. Gastrointest Endosc Clin N Am 2018; 28:89-96.

Gonsalves, N, et al. Elimination diet effectively treats eosinophilic esophagitis in adults; food reintroduction identifies causative factors. Gastroenterology, 142(7):1451-9.e1; quiz e14, Jun. 2012.

Gottlieb, SJ, et al. A role for food allergy testing in eosinophilic esophagitis. J Allergy Clin Immunol 2013; 131:242-3.

Guhsl, EE, et al. IgE, IgG4 and IgA specific to Bet v 1-related food allergens do not predict oral allergy syndrome. Allergy 2015; 70:59-66.

Holbreich M. Pearls and pitfalls in the management of eosinophilic esophagitis. Allergy Asthma Proc 2019;40:198-203.

Hommeida, S, et al. Assessing the incidence trend and characteristics of eosinophilic esophagitis in children in Olmsted County, Minnesota. Diseases of the Esophagus, 31(12), Dec. 2018.

Inage, E. Eosinophilic esophagitis: pathophysiology and its clinical implications. American Journal of Physiology. Gastrointestinal and Liver Physiology, Nov. 1, 018;315(5):G879-G886.

Jensen, ET, et al. Health-care utilization, costs, and the burden of disease related to eosinophilic esophagitis in the United States. The American journal of gastroenterology, 110(5):626-632, May 2015.

Kamdar TA, et al. Skin prick testing does not reflect the presence of IgE against food allergens in adult eosinophilic esophagitis patients: a case study. Clin Mol Allergy 2010; 8:16.

King, AR and Aug. 2012 University of Kansas Drug Information Center Experiential Rotation Students. Gluten content of the top 200 medications: Follow-up to the influence of gluten on a patient's medication choices. Hospital pharmacy, 48(9):736-743, Oct. 2013.

Koninckx CR, et al. IgA antigliadin antibodies in celiac and inflammatory bowel disease. J Pediatr Gastroenterol Nutr 1984; 3:676-82.

Kottyan, LC, et al. Genome-wide association analysis of eosinophilic esophagitis provides insight into the tissue specificity of this allergic disease. Nature Genetics, 46(8):895-900, Aug. 2014.

Lamm ME, et al. IgA and mucosal defense. APMIS 1995; 103:241-6.

Liacouras, CA, et al. Eosinophilic esophagitis: updated consensus recommendations for children and adults. The Journal of Allergy and Clinical Immunology, 128(1):3-20.e6; quiz 21, Jul. 2011.

Li-Kim-Moy, JP, et al. Esophageal subepithelial fibrosis and hyalinization are features of eosinophilic esophagitis. Journal of Pediatric Gastroenterology and Nutrition, 52(2):147-153, Feb. 2011.

Lucendo, AJ, et al. Systematic review: health-related quality of life in children and adults with eosinophilic oesophagitis-instruments for measurement and determinant factors. Aliment Pharmacol Ther 2017; 46:401-409.

Lucendo, AJ, et al. Empiric 6-food elimination diet induced and maintained prolonged remission in patients with adult eosinophilic esophagitis: a prospective study on the food cause of the disease. The Journal of Allergy and Clinical Immunology, 131(3):797-804, Mar. 2013.

Lucendo, AJ, et al. Guidelines on eosinophilic esophagitis: evidence-based statements and recommendations for diagnosis and management in children and adults. United European gastroenterology journal, 5(3):335-358, Apr. 2017.

Mansoor, E and Cooper, GS. The 2010-2015 Prevalence of Eosinophilic Esophagitis in the USA: A Population-Based Study. Digestive Diseases and Sciences, 61(10):2928-2934, Jun. 2016.

Mcgowan, EC, et al. Food allergy, eosinophilic esophagitis, and the enigma of IgG4. Ann Allergy Asthma Immunol Jun. 2019;122(6):563-564.

Molina-Infante, J, et al. Review article: proton pump inhibitor therapy for suspected eosinophilic oesophagitis. Alimentary Pharmacology & Therapeutics, 37(12):1157-1164, Jun. 2013.

Molina-Infante, J, et al. Four-food group elimination diet for adult eosinophilic esophagitis: A prospective multicenter study. The Journal of Allergy and Clinical Immunology, 134(5):1093-9.e1, Nov. 2014.

Motegi, Y, et al. Role of secretory IgA, secretory component, and eosinophils in mucosal inflammation. Int Arch Allergy Immunol 2000;122 Suppl 1:25-7.

Muraki, M, et al. Antigen-specific IgG and IgA, but not IgE, activate the effector functions of eosinophils in the presence of antigen. Int Arch Allergy Immunol 2011; 154:119-27.

O'Shea, KM, et al., Pathophysiology of Eosinophilic Esophagitis. 154(2):333-345, 2018.

Paquet B, et al. Variable yield of allergy patch testing in children with eosinophilic esophagitis. J Allergy Clin Immunol 2013;131:613.

Peiris CD, and Tarbox JA. Eosinophilic Esophagitis. JAMA 2019; 321:1418.

Peterson, KA, et al. Elemental diet induces histologic response in adult eosinophilic esophagitis. The American Journal of Gastroenterology, 108(5):759-766, May 2013.

Philpott, H, et al. Eosinophilic esophagitis: current understanding and evolving concepts. Asia Pacific allergy, 7(1):3-9, Jan. 2017.

Philpott H, et al. Allergy tests do not predict food triggers in adult patients with eosinophilic oesophagitis. A comprehensive prospective study using five modalities. Aliment Pharmacol Ther 2016; 44:223-33.

Philpott H and Thien F. The Role of Allergy Testing in Eosinophilic Esophagitis: an Update of the Evidence. Curr Treat Options Gastroenterol 2017;15:26-34.

Philpott, H and Dellon, ES. A Penetrating Look at Eosinophilic Esophagitis Pathogenesis: Direct Antigen Exposure in the Esophagus? Gastroenterology 2017;153:605-606.

Pilotto, A, et al. Comparison of four proton pump inhibitors for the short-term treatment of esophagitis in elderly patients. World Journal of Gastroenterology, 13(33):4467-4472, Sep. 2007.

Pope, AE, et al. Esophageal IgG4: Clinical, Endoscopic, and Histologic Correlations in Eosinophilic Esophagitis. J Pediatr Gastroenterol Nutr 2019; 68:689-694.

Ramaswamy AT, et al. Esophageal IgE, IgG4, and mucosal eosinophilia in individuals with dysphagia. Int Forum Allergy Rhinol 2019; 9:870-875.

Reed, CC, et al. Seasonal exacerbation of eosinophilic esophagitis histologic activity in adults and children implicates role of aeroallergens. Annals of Allergy, Asthma & Immunology, 122(3):296-301, Mar. 2019.

Reed, CC and Dellon, ES. Eosinophilic Esophagitis. Med Clin North Am 2019; 103:29-4.

Robson, J, et al. Incidence and Prevalence of Pediatric Eosinophilic Esophagitis in Utah Based on a 5-Year Population-Based Study, Clinical Gastroenterology and Hepatology, 17(1):107-114.e1, Jan. 2019.

Rosenberg, CE, et al. Esophageal IgG4 levels correlate with histopathologic and transcriptomic features in eosinophilic esophagitis. Allergy 2018; 73:1892-1901.

Rothenberg, ME, et al. Intravenous anti-IL-13 mAb QAX576 for the treatment of eosinophilic esophagitis. The Journal of Allergy and Clinical Immunology, 135(2):500-507, Feb. 2015.

Roufosse, F. Targeting the Interleukin-5 Pathway for Treatment of Eosinophilic Conditions Other than Asthma. Frontiers in medicine, 5:49, Apr. 2018.

Saffari, H, et al. Measurement of Inflammation in Eosinophilic Esophagitis Using an Eosinophil Peroxidase Assay. The American journal of gastroenterology, 111(7):933-939, Jul. 2016.

Sallis, BF, et al. An algorithm for the classification of mRNA patterns in eosinophilic esophagitis: Integration of machine learning. The Journal of allergy and clinical immunology, 141(4):1354-1364.e9, Apr. 2018.

Schoepfer, AM, et al. Esophageal dilation in eosinophilic esophagitis: effectiveness, safety, and impact on the underlying inflammation. The American Journal of Gastroenterology, 105(5):1062-1070, May 2010.

Schuyler AJ, et al. Specific IgG 4 antibodies to cow's milk proteins in pediatric patients with eosinophilic esophagitis. J Allergy Clin Immunol 2018; 142:139-148.

Sherrill, JD. Analysis and expansion of the eosinophilic esophagitis transcriptome by RNA sequencing. Genes and Immunity, 15(6):361-369, Sep. 2014.

(56)                 References Cited

OTHER PUBLICATIONS

Spergel, JM, et al. Summary of the updated international consensus diagnostic criteria for eosinophilic esophagitis: AGREE conference. Annals of Allergy, Asthma & Immunology, 121(3):281-284, Jul. 2018.

Spergel, JM, et al. Reslizumab in children and adolescents with eosinophilic esophagitis: results of a double-blind, randomized, placebo-controlled trial. The Journal of Allergy and Clinical Immunology, 129(2):456-63, 463.e1, Feb. 2012.

Straumann, A, et al. Long-term budesonide maintenance treatment is partially effective for patients with eosinophilic esophagitis. Clinical Gastroenterology and Hepatology, 9(5):400-9.e1, May 2011.

Straumann, A, et al. Anti-interleukin-5 antibody treatment (mepolizumab) in active eosinophilic oesophagitis: a randomised, placebo-controlled, double-blind trial. Gut, 59(1):21-30, Jan. 2010.

Turnbull JL, et al. Review article: the diagnosis and management of food allergy and food intolerances. Aliment Pharmacol Ther 2015; 41:3-25.

Warners MJ, et al. Abnormal Responses to Local Esophageal Food Allergen Injections in Adult Patients With Eosinophilic Esophagitis. Gastroenterology 2018; 154:57-60 e2.

Warners MJ, et al. Disease activity in eosinophilic esophagitis is associated with impaired esophageal barrier integrity. Am J Physiol Gastrointest Liver Physiol 2017; 313:G230-G238.

Wechsler, JB, et al. Elimination diets in the management of eosinophilic esophagitis. Journal of asthma and allergy, 7:85-94, May 2014.

Wright BL, et al. Food-specific IgG 4 is associated with eosinophilic esophagitis. J Allergy Clin Immunol 2016; 138:1190-1192.

Wolf, WA, et al. The Six-Food Elimination Diet for Eosinophilic Esophagitis Increases Grocery Shopping Cost and Complexity. Dysphagia, 31(6):765-770, Aug. 2016.

Wolf, WA and Dellon, ES. Eosinophilic esophagitis and proton pump inhibitors: controversies and implications for clinical practice. Gastroenterology & hepatology, 10(7):427-432, Jul. 2014.

Zuo, L, et al. IL-13 induces esophageal remodeling and gene expression by an eosinophil-independent, IL-13R alpha 2-inhibited pathway. Journal of Immunology, 185(1):660-669, Jul. 2010.

International Search Report and Written Opinion were mailed on Feb. 10, 2021 by the International Searching Authority for International Application No. PCT/US2020/054819, filed on Oct. 8, 2020 and published as WO 2021/072103 on Apr. 15, 2021 (Applicant—University of Utah Research Foundation) (11 Pages).

U.S. Appl. No. 62/912,505, filed Oct. 8, 2019, Kathryn A. Peterson.

PCT/US2020/054819 (WO 2021/072103), Oct. 8, 2020 (Apr. 15, 2021), Kathryn A. Peterson (University of Utah Research Foundation).

* cited by examiner

IgA Response Values for Trigger Food and Nontrigger Food

FIG. 4A

Separate sampling of FSA-IgA Distal disease (25eos) and proximal (6eos)

Separate sampling of FSA-IgG4 in Disease (25) and areas without Disease (4)

Separate sampling of FSA-IgG4 in disease and areas with less disease (22 and 1)

Separate sampling of FSA-IgA in Disease and Less Disease (22 versus 1)

METHODS FOR DETECTING A FOOD SPECIFIC IMMUNE RESPONSE

CROSS REFERENCE TO RELATED APPLICATIONS

This application claims the benefit of priority under 35 U.S.C. § 371 of International Application No. PCT/US2020/054819, filed Oct. 8, 2019, which claims the benefit of the filing date of U.S. Provisional Application No. 62/912,505, filed Oct. 8, 2019. The content of these earlier filed applications is hereby incorporated by reference in their entirety.

BACKGROUND

Food antigens are implicated in the induction and persistence of eosinophilic esophagitis. Dietary elimination to identify triggers is invasive, tedious, and expensive. Alternatives that can mitigate cost and improve patient quality-of-life during this process are needed.

SUMMARY

Disclosed herein are methods of detecting the binding of one or more food specific immunoglobulin (Ig) antibodies to one or more food antigens in a sample, the methods comprising: contacting a sample obtained from a subject with one or more food antigens and detecting the binding of the one or more food specific Ig antibodies to the one or more food antigens.

Disclosed herein are methods of detecting a food specific immune response in a sample, the methods comprising: a) contacting the sample with one or more food antigens; b) determining the presence of or level of one or more immunoglobulin (Ig) antibodies bound to the one or more food antigens; and c) comparing the level of the one or more Ig antibodies in the sample bound to the one or more food antigens in b) to the level of one or more Ig antibodies bound to the one or more food antigens in a reference sample; thereby detecting the food specific immune response in the sample when the level of the one or more Ig antibodies in the sample bound to the one or more food antigens is higher than the level of one or more Ig antibodies in a reference sample.

Disclosed herein are methods of identifying a food allergy in a subject with active or inactive eosinophilic esophagitis (EoE) in a subject suffering from EoE, the methods comprising: a) detecting the presence of or level of one or more immunoglobulin (Ig) antibodies bound to the one or more food antigens in a sample; and b) comparing the level of the one or more Ig antibodies bound to the one or more food antigens in the sample to the level of one or more Ig antibodies bound to the one or more food antigens in a reference sample; wherein the level of the one or more Ig antibodies in the sample bound to the one or more food antigens is higher than the level of one or more Ig antibodies bound to the one or more food antigens in a reference sample identifies a food allergy in the subject.

Disclosed herein are methods of treating a subject with active or inactive eosinophilic esophagitis (EoE) in a subject suffering from EoE, the methods comprising: a) detecting the presence of or level of one or more immunoglobulin (Ig) antibodies bound to the one or more food antigens in a sample; b) comparing the level of the one or more Ig antibodies bound to the one or more food antigens in the sample to the level of one or more Ig antibodies bound to the one or more food antigens in a reference sample; and c) treating the subject.

Disclosed herein are methods of treating a subject with active eosinophilic esophagitis (EoE) in a subject suffering from EoE, the methods comprising: a) detecting the presence of or level of one or more immunoglobulin (Ig) antibodies bound to the one or more food antigens in a sample; b) comparing the level of the one or more Ig antibodies bound to the one or more food antigens in the sample to the level of one or more Ig antibodies bound to the one or more food antigens in a reference sample; and c) treating the subject.

Disclosed herein are methods of diagnosing and treating a subject with active or inactive eosinophilic esophagitis (EoE) in a subject suffering from EoE, the methods comprising: a) detecting the presence of or level of one or more one or more immunoglobulin (Ig) antibodies bound to the one or more food antigens in a sample; b) comparing the level of the one or more Ig antibodies bound to the one or more food antigens in the sample to the level of one or more Ig antibodies bound to the one or more food antigens in a reference sample; c) diagnosing the subject with active EoE when the level of the one or more Ig antibodies in the sample bound to the one or more food antigens is higher than the level of one or more Ig antibodies bound to the one or more food antigens in a reference sample and diagnosing the subject with inactive EoE when the level of the one or more Ig antibodies in the sample bound to the one or more food antigens is lower than the level of one or more Ig antibodies bound to the one or more food antigens in a reference sample level; and d) treating the subject diagnosed with active EoE, wherein the level of the one or more Ig antibodies in the sample bound to the one or more food antigens is higher than the level of one or more Ig antibodies bound to the one or more food antigens in a reference sample.

Disclosed herein are methods for diagnosing and treating eosinophilic esophagitis in a subject in need thereof, the methods comprising: (i) measuring the gene expression level for at least one gene in an esophageal biopsy sample from the patient, wherein the at least one gene selected from the group consisting of: eosinophil peroxidase, periostin, Eotaxin-3, stem cell factor, or CCL26, KITLG, and POSTN, wherein the measuring the gene expression level is performed by a method comprising DNA microarray analysis, polymerase chain reaction analysis, or both; (ii) comparing the gene expression level for the at least one gene to its expression level in an esophageal biopsy sample from a normal individual defined as having zero eosinophils per high power field and no basal layer expansion; (iii) diagnosing eosinophilic esophagitis in the subject where the expression level of the at least one gene is increased more than 10-fold compared to its expression level in the esophageal biopsy sample from a normal individual, and (iv) treating the eosinophilic esophagitis in the subject diagnosed according to step (iii) with one or more therapies selected from an anti-inflammatory therapy, allergen elimination, a cytokine inhibitor, an immunosuppressant, and a complement inhibitor.

Disclosed herein are method of diagnosing eosinophilic esophagitis (EoE) by detecting one or more biomarkers selected from the group consisting of eosinophil peroxidase, periostin, Eotaxin-3, stem cell factor, or CCL26, KITLG, and POSTN.

Disclosed herein are methods of detecting the cause of an eosinophilic esophagitis (EoE) symptom, wherein the EoE symptom is caused by an immune response to an antigen in a patient diagnosed with or suffering from EOE, the method comprises: obtaining or having obtained an esophageal mucosal sample from a subject, wherein the esophageal mucosal sample obtained from the subject is from the site of the immune response, wherein the esophageal mucosal sample comprise one or more immunoglobulin (Ig) antibodies;

contacting the sample with one or more antigens; and detecting the binding of the one or more specific Ig antibodies to the one or more antigens.

BRIEF DESCRIPTION OF THE DRAWINGS

FIGS. 4A-D shows Immunoglobulin A and Immunoglobulin G4 antibodies in esophageal secretions of EoE patients: comparison of trigger and non-trigger foods. FIG. 4A shows the Immunoglobulin A responses to trigger and non-trigger foods. FIG. 4B shows a heatmap depicting Immunoglobulin A responses in each individual to trigger foods as compared to non-trigger foods. Red depicts the higher response levels detected. Most trigger foods resulted in response values in the higher ranges. FIG. 4C shows Immunoglobulin G4 responses to trigger and non-trigger foods. FIG. 4D shows a heatmap of Immunoglobulin G4 responses to trigger and non-trigger foods in each individual. IgA=Immunoglobulin A. IgG4=Immunoglobulin G4

FIG. 6A shows food specific antibody (FSA)-IgA diffuse panesophageal sampling—132 eos/HPF as the peak count and pan esophagitis (i.e., involvement of the entire esophagus with inflammation). FIG. 6B shows FSA-IgG4 pansampling of esophagus with 95 eosinophils and disease throughout. FIG. 6C shows FSA-IgA pan-esophageal sampling of esophagus with 95 eosinophils and disease throughout. FIG. 6D shows FSA-IgA pan-sampling of esophagus 25-30 eosinophils throughout.

FIG. 7A shows separate sampling of FSA-IgA distal disease (25 eos) and proximal (6 eos). FIG. 7B shows separate sampling of FSA-IgG4 in disease (25) and areas without disease (4). FIG. 7C shows separate sampling of FSA-IgG4 in disease and areas with less disease (22 and 1). FIG. 7D shows separate sampling of FSA-IgA in disease and less disease (22 vs 1).

FIG. 8A shows eotaxin. FIG. 8B shows SCF. FIG. 8C shows periostin.

FIG. 9A depicts one patient who could not complete diet elimination but was symptomatic on dairy. FIG. 9B depicts a patient who opted for topical steroids. FIG. 9C was performed on a patient who ultimately underwent food elimination diet (six food elimination). With food reintroduction, wheat was identified as his trigger food. In FIG. 9C, the patient's EoE was found to be triggered by wheat. As seen in the diagrams, esophageal secretions demonstrated high response values to gluten while serum and saliva had elevated responses to other food antigens, indicating that this participant likely had a local response from his diseased tissues. Contamination from serum or saliva should create similar patterns of response in the esophageal collections—which is not seen here.

DETAILED DESCRIPTION

Figure 1:
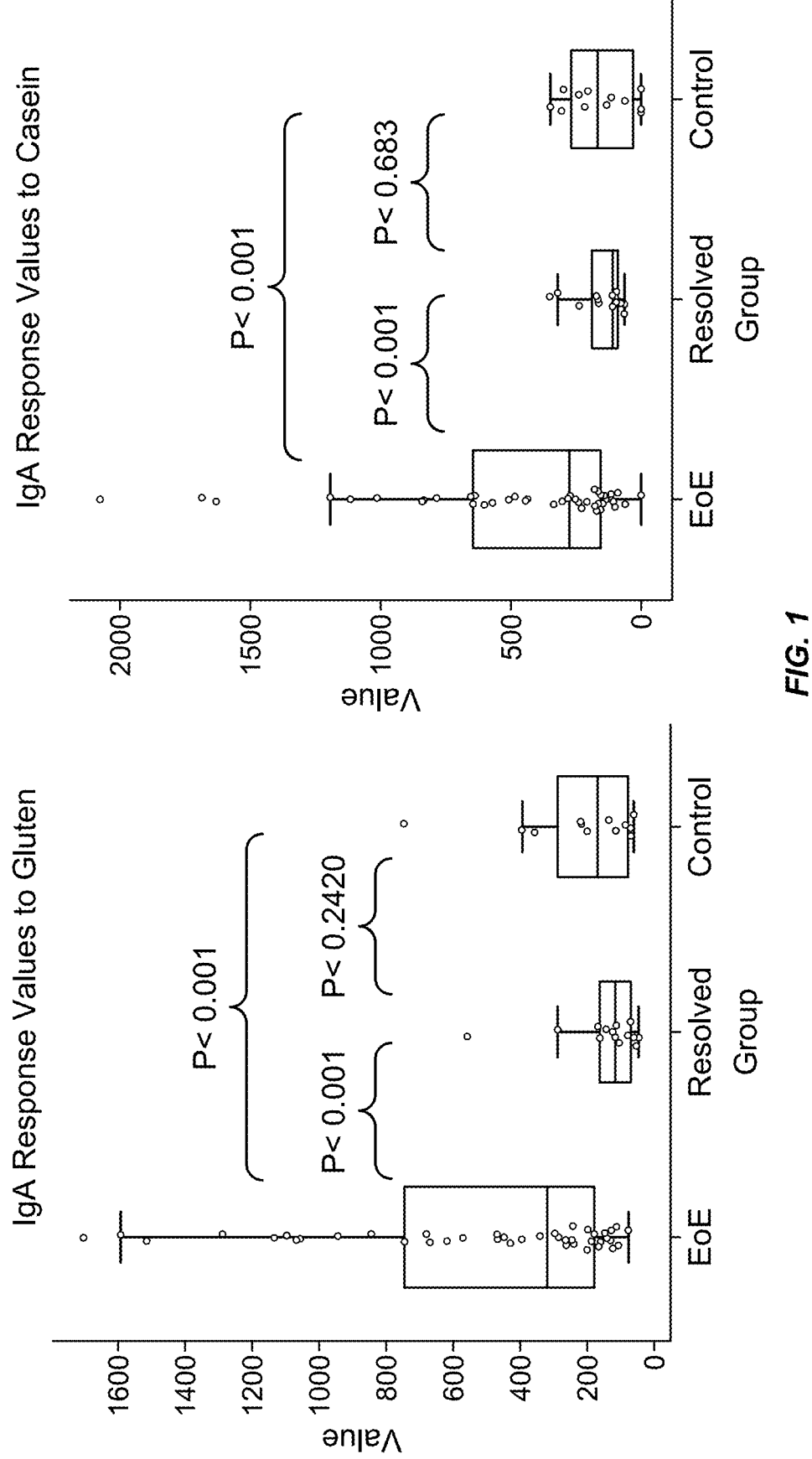
FIG. 1 shows the Immunoglobulin A response values for gluten, casein, soy, and egg in cohorts: EoE (n=43), resolved EoE (n=13) and controls (n=12). Resolved patients were not significantly different from controls on any paired testing. Active EoE had significantly increased antibody values to gluten, casein, and egg compared to the other two groups and differed from resolved patients for the antibody response levels. IgA=Immunoglobulin A.
Figure 1:
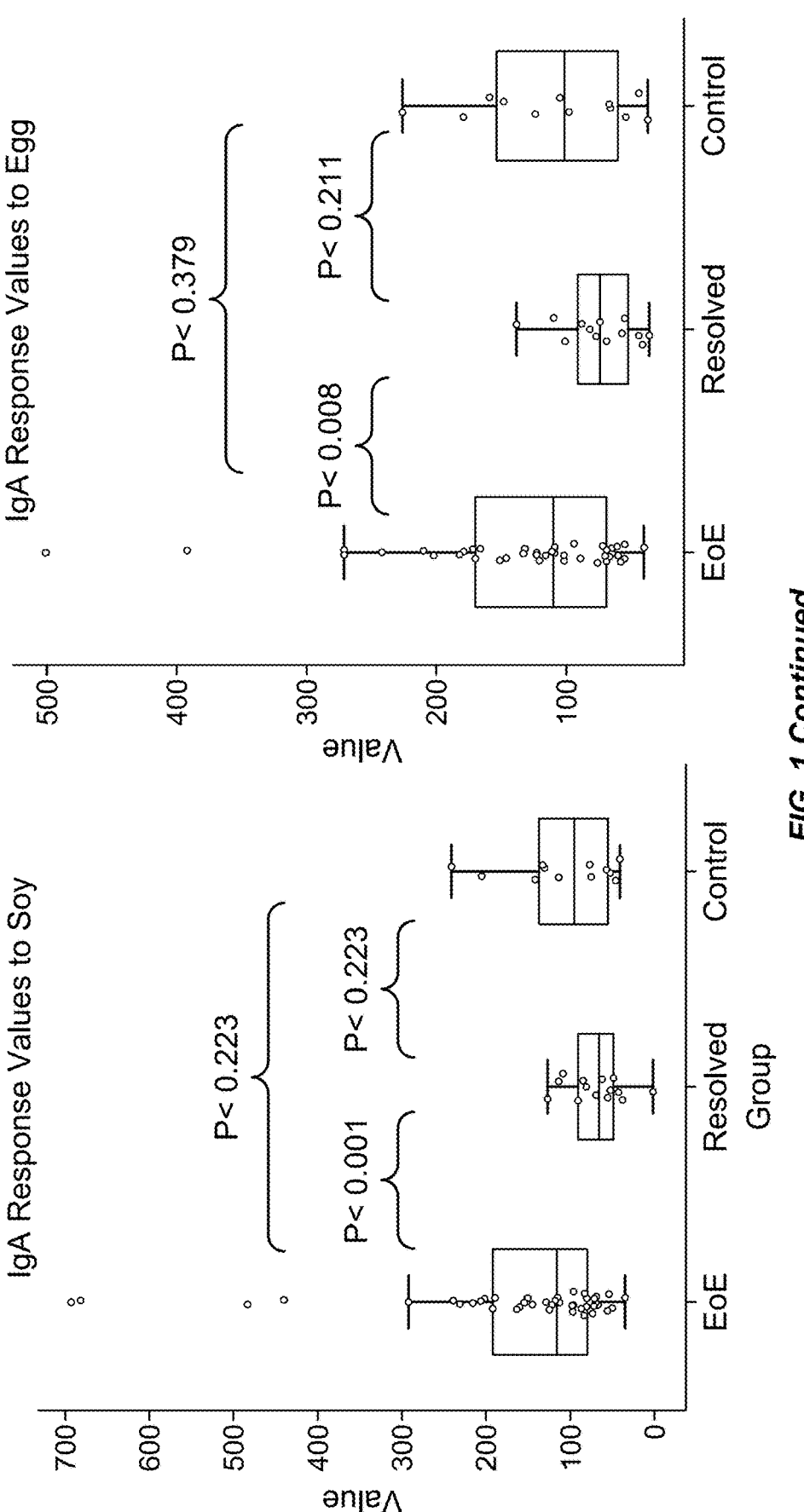

The present invention may be understood more readily by reference to the following detailed description of various aspects of the invention and the Examples included therein and to the Figures and their previous and following description.

Before the present compounds, compositions, articles, devices, and/or methods are disclosed and described, it is to be understood that this invention is not limited to specific synthetic methods or specific radiolabeled contrast agents, as such may, of course, vary. It is also to be understood that the terminology used herein is for the purpose of describing particular aspects only and is not intended to be limiting.

Unless defined otherwise, all technical and scientific terms used herein have the same meanings as commonly understood by one of skill in the art to which the disclosed methods and compositions belong. Although any methods and materials similar or equivalent to those described herein can be used in the practice or testing of the disclosed methods and compositions, the particularly useful methods, devices, and materials are as described.

It is understood that the disclosed methods and compositions are not limited to the particular methodology, protocols, and reagents described, as these may vary. It is also to be understood that the terminology used herein is for the purpose of describing particular aspects only and is not intended to limit the scope of the present invention which will be limited only by the appended claims.

As used in the specification and the appended claims, the singular forms "a," "an," and "the" include plural referents unless the context clearly dictates otherwise.

The word "or" as used herein means any one member of a particular list and also includes any combination of members of that list.

As used herein, the terms "optional" or "optionally" mean that the subsequently described event or circumstance may or may not occur and that the description includes instances where said event or circumstance occurs and instances where it does not.

As used herein, the term "sample" is meant a tissue or organ from a subject; a cell (either within a subject, taken directly from a subject, or a cell maintained in culture or from a cultured cell line); a cell lysate (or lysate fraction) or cell extract; or a solution containing one or more molecules derived from a cell or cellular material (e.g., a polypeptide or nucleic acid). A sample may also be any body fluid or excretion (for example, but not limited to, blood, urine, stool, saliva, tears, bile) that contains cells or cell components. or effluent from a disease state (i.e., created by the disease itself).

Ranges may be expressed herein as from "about" one particular value and/or to "about" another particular value. When such a range is expressed, another aspect includes¬ from the one particular value and/or to the other particular value. Similarly, when values are expressed as approximations, by use of the antecedent "about," it will be understood that the particular value forms another aspect. It will be further understood that the endpoints of each of the ranges are significant, both in relation to the other endpoint and independently of the other endpoint.

As used herein, the word "comprise" and variations of the word, such as "comprising" and "comprises," means "including, but not limited to" and is not intended to exclude, for example, other additives, components, integers or steps.

As used herein, by "subject" is meant an individual. A subject can be a mammal such as a primate, for example, a human. The term "subject" includes domesticated animals such as cats, dogs, etc., livestock (e.g., cattle, horses, pigs, sheep, goats, etc.), and laboratory animals (e.g., mice, rabbits, rats, gerbils, guinea pigs, possums, etc.). As used herein, the terms "subject" and "patient" are interchangeable.

As used herein, the term "patient" refers to a subject afflicted with a disease or disorder. The term "patient" includes human and veterinary subjects. In some aspects of the disclosed methods, the "patient" has been diagnosed with a need for treatment, for example, prior to the administering step.

As used herein, a "mucosal tissue" is a tissue lining various cavities within the body. Examples of a mucosal tissue include, but are not limited to, mucosal tissue lining the nose, sinuses, bronchi, lungs, conjunctiva, oral cavity, tongue, esophagus, stomach, pylorus, duodenum, jejunum, ileum, ascending colon, caecum, appendix, transverse colon, descending colon, rectum, anus, urethra, dermis, small bowel (small intestine), large bowel (large intestine), biliary tree and biliary system, and urinary bladder. A mucosal tissue comprises an epithelial surface, glandular epithelium which secretes mucus, basement membrane, and submucosa with connective tissue. In some aspects, a mucosal tissue is from the esophagus of a subject. In some aspects, a mucosal tissue is from the intestines of a subject. In some aspects, the mucosal tissue is gastrointestinal mucosal tissue. In some aspects, the mucosal tissue is gastrointestinal mucosal tissue secretions. In some aspects, the mucosal tissue is small bowel fluid from the bowel lining. In some aspects the mucosal tissue is esophageal mucosal tissue secretions.

As used herein, an "eosinophil granule protein" is a protein that comprises the granules in eosinophils. When an eosinophil is activated, granule proteins are released from the cell into the surrounding tissue. The released granule proteins can cause pathologic allergenic inflammatory responses in the surrounding tissue, for example esophageal mucosal tissue. Examples of eosinophil granule proteins include, but are not limited to, major basic protein (MBP), major basic protein 1 (MBP-1), major basic protein 2 (MBP-2), eosinophil derived neurotoxin (EDN, also referred to as RNase2), eosinophil cationic protein (ECP, also referred to as RNase3), and eosinophil peroxidase (EPO). Other examples of eosinophil granule proteins are provided in Kita et al., Biology of Eosinophils, Chapter 19 of Immunology, which is hereby incorporated by reference for its teaching of examples of eosinophil granule proteins. In some aspects, an eosinophil granule protein can be MBP-1.

As used herein, the term "gene" refers to a region of DNA encoding a functional RNA or protein. "Functional RNA" refers to an RNA molecule that is not translated into a protein. Generally, the gene symbol is indicated by using italicized styling while the protein symbol is indicated by using non-italicized styling.

The phrase "nucleic acid" as used herein refers to a naturally occurring or synthetic oligonucleotide or polynucleotide, whether DNA or RNA or DNA-RNA hybrid, single-stranded or double-stranded, sense or antisense, which is capable of hybridization to a complementary nucleic acid by Watson-Crick base-pairing. Nucleic acids of the invention can also include nucleotide analogs, and non-phosphodiester internucleoside linkages (e.g., peptide nucleic acid (PNA) or thiodiester linkages). In particular, nucleic acids can include, without limitation, DNA, RNA, cDNA, gDNA, ssDNA, dsDNA or any combination thereof.

By "isolated nucleic acid" or "purified nucleic acid" is meant DNA that is free of the genes that, in the naturally-occurring genome of the organism from which the DNA of the invention is derived, flank the gene. The term therefore includes, for example, a recombinant DNA which is incorporated into a vector, such as an autonomously replicating plasmid or virus; or incorporated into the genomic DNA of a prokaryote or eukaryote (e.g., a transgene); or which exists as a separate molecule (for example, a cDNA or a genomic or cDNA fragment produced by PCR, restriction endonuclease digestion, or chemical or in vitro synthesis). It also includes a recombinant DNA which is part of a hybrid gene encoding additional polypeptide sequence. The term "isolated nucleic acid" also refers to RNA, e.g., an mRNA molecule that is encoded by an isolated DNA molecule, or that is chemically synthesized, or that is separated or substantially free from at least some cellular components, for example, other types of RNA molecules or polypeptide molecules.

By "specifically binds" is meant that an antibody recognizes and physically interacts with its cognate antigen and does not significantly recognize and interact with other antigens; such an antibody may be a polyclonal antibody or a monoclonal antibody, which are generated by techniques that are well known in the art.

By "probe," "primer," or oligonucleotide is meant a single-stranded DNA or RNA molecule of defined sequence that can base-pair to a second DNA or RNA molecule that contains a complementary sequence (the "target"). The stability of the resulting hybrid depends upon the extent of the base-pairing that occurs. The extent of base-pairing is affected by parameters such as the degree of complementarity between the probe and target molecules and the degree of stringency of the hybridization conditions. The degree of hybridization stringency is affected by parameters such as temperature, salt concentration, and the concentration of organic molecules such as formamide, and is determined by methods known to one skilled in the art. Probes or primers specific for nucleic acids (for example, genes and/or mRNAs) have at least 80%-90% sequence complementarity, preferably at least 91%-95% sequence complementarity, more preferably at least 96%-99% sequence complementarity, and most preferably 100% sequence complementarity to the region of the nucleic acid to which they hybridize. Probes, primers, and oligonucleotides may be detectably-labeled, either radioactively, or non-radioactively, by methods well-known to those skilled in the art. Probes, primers, and oligonucleotides are used for methods involving nucleic acid hybridization, such as: nucleic acid sequencing, reverse transcription and/or nucleic acid amplification by the polymerase chain reaction, single stranded conformational polymorphism (SSCP) analysis, restriction fragment polymorphism (RFLP) analysis, Southern hybridization, Northern hybridization, in situ hybridization, electrophoretic mobility shift assay (EMSA).

By "specifically hybridizes" is meant that a probe, primer, or oligonucleotide recognizes and physically interacts (that is, base-pairs) with a substantially complementary nucleic acid under high stringency conditions, and does not substantially base pair with other nucleic acids.

By "high stringency conditions" is meant conditions that allow hybridization comparable with that resulting from the use of a DNA probe of at least 40 nucleotides in length, in a buffer containing 0.5 M $NaHPO_4$, pH 7.2, 7% SDS, 1 mM EDTA, and 1% BSA (Fraction V), at a temperature of 65° C., or a buffer containing 48% formamide, 4.8×SSC, 0.2 M Tris-Cl, pH 7.6, 1×Denhardt's solution, 10% dextran sulfate, and 0.1% SDS, at a temperature of 42° C. Other conditions for high stringency hybridization, such as for PCR, Northern, Southern, or in situ hybridization, DNA sequencing, etc., are well-known by those skilled in the art of molecular biology. (See, for example, F. Ausubel et al., Current Protocols in Molecular Biology, John Wiley & Sons, New York, NY, 1998).

Eosinophilic esophagitis (EoE) is an immune-mediated disease of the esophagus that is commonly triggered by food antigens. EoE was uncharacterized prior to 1993, but is now the most common cause of dysphagia (difficulty swallowing) and food impaction requiring esophageal endoscopy. EoE causes acute food impaction that requires emergency endoscopic removal. Chronic EoE causes fibrostenotic stricture formation and esophageal remodeling, and patients require periodic esophageal dilatation in order to eat. The mechanism of fibrosis in EoE is poorly studied, and optimal prevention strategies are unknown. EoE is diagnosed by endoscopic biopsy, which is invasive and incurs significant costs for patients. Food antigens that trigger EoE are determined through diet elimination trials, which can span years and consist of routine, near-monthly biopsies.

The compositions and methods disclosed herein focus on the following clinical needs for EoE patients: to develop a non-invasive diagnostic modality, and to develop a method for rapid identification of trigger antigens. As disclosed herein, it was tested whether such antigenic footprints reflected recent consumption of foods and if the disease itself manifested the antigenic signals and determined whether removal of food triggers resulted in reduced food specific signals despite ongoing disease (i.e., whether signals were dependent upon antigen exposure). RNA-seq and histopathologic validation was used to show that a subepithelial immunoregulatory response is characteristic of EoE and can induce fibrosis. RNA-seq and quantitative protein assays were also used to identify diagnostic biomarkers in esophageal secretions collected by non-less-invasive brushing. Also described herein are methods to accurately predict and determine trigger foods using food-specific antibodies in esophageal secretions and the response to active exposure and removal of antigens.

Eosinophilic esophagitis (EoE) is a serious and increasingly common immunologic cause of esophageal dysphagia and dysmotility (E. S. Dellon; Updated international consensus diagnostic criteria for eosinophilic esophagitis: proceedings of the AGREE conference. Gastroenterology, 155 (4):1022-1033.e10, September 2018). It is becoming one of the most common causes of dysphagia in children and young adults (E. S. Dellon; Updated international consensus diagnostic criteria for eosinophilic esophagitis: proceedings of the AGREE conference. Gastroenterology, 155(4):1022-1033.e10, September 2018; J. M. Spergel, et al. Annals of Allergy, Asthma & Immunology, 121(3):281-284, July 2018; and E. Inage. American Journal of Physiology. Gastrointestinal and Liver Physiology, 315(5), September 2018). Twelve-23% of dysphagia cases that require endoscopy are caused by EoE (E S Dellon. Gastroenterology Clinics of North America, 43(2):201-218, June 2014). Recent literature has estimated the prevalence of EoE to be 0.5-1 per 1,000 and the incidence of EoE to be 5-10 per 100,000 persons (E. S. Dellon; Updated international consensus diagnostic criteria for eosinophilic esophagitis: proceedings of the AGREE conference. Gastroenterology, 155 (4):1022-1033.e10, September 2018). The increasing prevalence of EoE is due to the chronic nature of the disease, and due to increased diagnoses due to more widespread recognition of the disease (A. Arias and A J Lucendo. Digestive and Liver Disease, July 2018; S Hommeida, et al. Diseases of the Esophagus, 31(12), December 2018; and Jacob Robson, et al. Clinical Gastroenterology and Hepatology, 17(1), June 2018). Males are predisposed to EoE by a factor of 3:1 (E Mansoor and G S Cooper. Digestive Diseases and Sciences, 61(10):2928-2934, June 2016; and C A Liacouras et al. The Journal of Allergy and Clinical Immunology, 128(1):3-20.e6; quiz 21, July 2011). Caucasians are 3 times more likely to develop EoE compared to African- or Asian-Americans (E Mansoor and G S Cooper. Digestive Diseases and Sciences, 61(10):2928-2934, June 2016; and C A Liacouras et al. The Journal of Allergy and Clinical Immunology, 128(1):3-20.e6; quiz 21, July 2011). EoE patients are more likely to present with atopic disorders (e.g. asthma, allergic rhinitis, and atopic dermatitis) (E Mansoor and G S Cooper. Digestive Diseases and Sciences, 61(10):2928-2934, June 2016; and C A Liacouras et al. The Journal of Allergy and Clinical Immunology, 128(1):3-20.e6; quiz 21, July 2011).

EoE is an immune-mediated disease, and symptoms are triggered by antigen exposure (E. S. Dellon; Updated international consensus diagnostic criteria for eosinophilic esophagitis: proceedings of the AGREE conference. Gastroenterology, 155(4):1022-1033.e10, September 2018; J. M. Spergel, et al. Annals of Allergy, Asthma & Immunology, 121(3):281-284, July 2018; and E. Inage. American Journal of Physiology. Gastrointestinal and Liver Physiology, 315 (5), September 2018). It is most commonly triggered by food antigens, and six foods trigger about 70% of cases: wheat, dairy, eggs, soy, seafood, and nuts (E. S. Dellon; Updated international consensus diagnostic criteria for eosinophilic esophagitis: proceedings of the AGREE conference. Gastroenterology, 155(4):1022-1033.e10, September 2018; J. M. Spergel, et al. Annals of Allergy, Asthma & Immunology, 121(3):281-284, July 2018; and E. Inage. American Journal of Physiology. Gastrointestinal and Liver Physiology, 315(5), September 2018). Aeroallergens also cause EoE, and symptom severity can vary by season, pollution, or geography (Matthew I Fogg, et al. The Journal of Allergy and Clinical Immunology, 112(4):796-797, October 2003; and Craig C Reed, et al. Annals of Allergy, Asthma & Immunology, 122(3):296-301, March 2019).

EoE has strong heritable and environmental components. Monozygotic twin studies show that EoE has 14.5% genetic inheritability, but 81.0% of variability is attributable to shared environment (E S Alexander et al. The Journal of Allergy and Clinical Immunology, 134(5):1084-1092.e1, November 2014). Familial recurrence risk ratios for EoE range from 10-64-fold, and is highest among male relatives (E S Alexander et al. The Journal of Allergy and Clinical Immunology, 134(5):1084-1092.e1, November 2014). GWAS studies have identified variants several genes involved in T-helper 2 (Th2) cell signaling that increase the risk of developing EoE (L C Kottyan et al. Nature Genetics, 46(8):895-900, August 2014). RNA-seq studies have also shown increased expression of genes induced by IL-13, a Th2 cytokine, in esophageal biopsies from EoE patients (J D Sherrill. Genes and Immunity, 15(6):361-369, September 2014).

The downstream effects of Th2 cytokine signaling give rise to several pathogenic features of EoE, in particular IL-5 and IL-13 signaling (K M O'Shea, et al., 154(2):333-345, 2018). In mouse studies, IL-5 was shown to be important for eosinophil maturation and mucosal eosinophilia (F Roufosse. Frontiers in medicine, 5:49, April 2018). In humans, IL-13 expression is increased in patients with EoE and induces epithelial expression of eotaxin-3, encoded by CCL26 (C Blanchard, et al. The Journal of Allergy and Clinical Immunology, 120(6):1292-1300, December 2007). In mouse studies, IL-13 expression overexpression was sufficient to cause esophageal eosinophilia (C Blanchard, et al. Clinical and Experimental Allergy, 35(8):1096-1103, August 2005), and could induce fibrosis independent of eosinophils (L Zuo, et al. Journal of Immunology, 185(1): 660-669, July 2010).

Acute symptoms in EoE include, but are not limited to, dysphagia, odynophagia, and edema leading to food bolus impaction (H Philpott, et al. Asia Pacific allergy, 7(1):3-9, January 2017). Chronically untreated EoE is associated with esophageal remodeling, stiffening, and dysmotility (K M O'Shea, et al. Gastroenterology, 154(2):333-345, 2018). These changes cause esophageal narrowing and impair the movement of food boli due to the lack of coordinated contractions (K M O'Shea, et al. Gastroenterology, 154(2): 333-345, 2018). Ultimately, esophageal dilatation is sometimes necessary to alleviate dysphagia induced by fibrotic remodeling (A M Schoepfer, et al. The American Journal of Gastroenterology, 105(5):1062-1070, May 2010). Fibrostenotic strictures do not develop in all EoE patients, and has been estimated using ICD-9 codes for dysphagia and food impaction at 57-90% (Evan S Dellon. Gastroenterology Clinics of North America, 43(2):201-218, June 2014; C A Liacouras et al. The Journal of Allergy and Clinical Immunology, 128(1):3-20.e6; quiz 21, July 2011; and Jean P Li-Kim-Moy, et al. Journal of Pediatric Gastroenterology and Nutrition, 52(2):147-153, February 2011).

The precise mechanism of subepithelial fibrosis in EoE is unknown (Jennifer Armbruster-Lee, et al. Journal of Leukocyte Biology, 104(1):31-40, July 2018).

EoE is currently diagnosed by endoscopic biopsy. Current consensus criteria for diagnosing EoE is #15 eosinophils per high power microscopic field in at least one biopsy (E S Dellon et al. Updated international consensus diagnostic criteria for eosinophilic esophagitis: proceedings of the AGREE conference. Gastroenterology, 155(4):1022-1033.e10, September 2018). The patchiness of eosinophilic infiltrates in EoE means that more than one biopsy is required in order to avoid false negatives (A J Lucendo et al. United European gastroenterology journal, 5(3):335-358, April 2017). Endoscopic biopsies are also used in order to assess treatment response (A J Lucendo et al. United European gastroenterology journal, 5(3):335-358, April 2017). A treatment is considered successful if, upon follow-up, histologic resolution is observed by biopsy (A J Lucendo et al. United European gastroenterology journal, 5(3):335-358, April 2017).

In order to identify causative food triggers for a patient's EoE, diet elimination trials are performed (A J Lucendo et al. United European gastroenterology journal, 5(3):335-358, April 2017). In these trials, a causative food is identified if histologic resolution occurs after elimination from a patient's diet, and the disease recurs after reintroduction of the food to a patient's diet (J B Wechsler, et al. Journal of asthma and allergy, 7:85-94, May 2014). Some guidelines recommend the elimination of six foods that, by empiric frequency, trigger the majority of EoE cases (J B Wechsler, et al. Journal of asthma and allergy, 7:85-94, May 2014). In practice, there is substantial variability in the choice and sequence of diet elimination due to socioeconomic factors, lifestyle choices, and health literacy of a patient (J B Wechsler, et al. Journal of asthma and allergy, 7:85-94, May 2014). Non-compliance with diet elimination is frequently observed, and patient adherence can be difficult to assess (J B Wechsler, et al. Journal of asthma and allergy, 7:85-94, May 2014). The difficulty of assessing patient adherence is further complicated by the ubiquity and non-obvious use of common EoE antigens in consumer products, such as medication capsules that are made from wheat gluten (A R King and August 2012 University of Kansas Drug Information Center Experiential Rotation Students. Gluten content of the top 200 medications: Follow-up to the influence of gluten on a patient's medication choices. Hospital pharmacy, 48(9): 736-743, October 2013).

Multiple treatments are used in the treatment of EoE. Common first-line therapies include diet elimination, proton-pump inhibitors (PPIs), and topical corticosteroids (TCS) (A J Lucendo et al. United European gastroenterology journal, 5(3):335-358, April 2017). Biologics and targeted therapies are also being explored in clinical trials (K M O'Shea, et al. Gastroenterology, 154(2):333-345, 2018), none of which are fully effective for treating EoE, thus, alternative treatments are still needed.

Elimination of trigger foods is a highly effective treatment for EoE, and 74% of patients resolve after elimination of the six most common food triggers (A J Lucendo et al. United European gastroenterology journal, 5(3):335-358, April 2017). However, a therapeutic diet is not always feasible and is dependent on patient adherence, socioeconomic factors, or budgetary constraints (W A Wolf, et al. Dysphagia, 31(6):

765-770, August 2016). Diet elimination is also ineffective for patients with EoE triggered by aeroallergens (J B Wechsler, et al. Journal of asthma and allergy, 7:85-94, May 2014).

Proton pump inhibitor therapy results in clinical and histologic remission of EoE in about one third of EoE patients (J Molina-Infante, et al. Alimentary Pharmacology & Therapeutics, 37(12):1157-1164, June 2013). Previous guidelines required patients to be non-responsive to PPIs before a diagnosis of EoE could be made, while patients who resolved on PPIs were classified as PPI-responsive EoE (PPI-REE). Current guidelines do not distinguish PPI-REE from EoE (E S Dellon et al. Updated international consensus diagnostic criteria for eosinophilic esophagitis: proceedings of the AGREE conference. Gastroenterology, 155(4):1022-1033.e10, September 2018). PPIs have relatively mild adverse effects and are generally well-tolerated (A Pilotto, et al. World Journal of Gastroenterology, 13(33):4467-4472, September 2007). However, in many patients PPI treatment is not effective for long term remission of EoE (A J Lucendo et al. United European gastroenterology journal, 5(3):335-358, April 2017). The mechanism of action of PPIs in EoE is still poorly understood (W Asher Wolf and Evan S Dellon. Gastroenterology & hepatology, 10(7):427-432, July 2014).

Topical corticosteroids (TCS) induce clinical and histologic resolution of EoE in a pro- portion of patients (B K Butz, et al. Gastroenterology, 147(2):324-33.e5, August 2014). TCS are also effective in maintaining long term remission for a proportion of patients (A Straumann, et al. Clinical Gastroenterology and Hepatology, 9(5):400-9.e1, May 2011). However, in 10% of patients, TCS causes esophageal candidiasis due to immunosuppression (A Straumann, et al. Clinical Gastroenterology and Hepatology, 9(5):400-9.e1, May 2011; and D A Andreae et al. The American Journal of Gastroenterology, 111(8):1187-1197, June 2016).

Clinical trials for biologics and targeted therapeutics have focused on inhibiting Th2-related signaling in EoE. Anti-IL5 monoclonal antibodies (i.e., mepolizumab, reslizumab) have demonstrated moderate efficacy in reducing esophageal eosinophilia but have no effect on clinical symptoms (A Straumann, et al. Gut, 59(1):21-30, January 2010; A H Assa'ad, et al. Gastroenterology, 141(5):1593-1604, November 2011; and J M Spergel, et al. The Journal of Allergy and Clinical Immunology, 129(2):456-63, 463.e1, February 2012). Anti-IL13 monoclonal antibodies also reduced esophageal eosinophilia but did not improve clinical symptoms (M E Rothenberg, et al. The Journal of Allergy and Clinical Immunology, 135(2):500-507, February 2015). Clinical trials for monoclonal antibodies targeting the IL-4 receptor are currently being tested in clinical trials for EoE (K M O'Shea, et al. Gastroenterology, 154(2):333-345, 2018). CRTH2 inhibitors, which interfere with eosinophil chemotaxis, reduced but did not completely resolve esophageal eosinophilia (K M O'Shea, et al. Gastroenterology, 154(2):333-345, 2018).

Currently, diet elimination trials are the established method to identify food antigens that trigger EoE (N Gonsalves, et al. Gastroenterology, 142(7):1451-9.e1; quiz e14, June 2012; K A Peterson, et al. The American Journal of Gastroenterology, 108(5):759-766, May 2013; A J Lucendo, et al. The Journal of Allergy and Clinical Immunology, 131(3):797-804, March 2013; and J Molina-Infante, et al. The Journal of Allergy and Clinical Immunology, 134(5):1093-9.e1, November 2014). However, diet elimination trials often span years, and consist of endoscopic biopsies that must be repeated on a periodic basis, often monthly, to assess clinical response (N Gonsalves, et al. Gastroenterology, 142(7):1451-9.e1; quiz e14, June 2012; K A Peterson, et al. The American Journal of Gastroenterology, 108(5):759-766, may 2013; A J Lucendo, et al. The Journal of Allergy and Clinical Immunology, 131(3):797-804, March 2013; and J Molina-Infante, et al. The Journal of Allergy and Clinical Immunology, 134(5):1093-9.e1, November 2014). These trials compound the financial burden and decreased quality of life imposed by endoscopic biopsies, which can cause poor patient compliance (J B Wechsler, et al. Journal of asthma and allergy, 7:85-94, May 2014; and W A Wolf, et al. Dysphagia, 31(6):765-770, August 2016). Furthermore, diet elimination trials are not effective for EoE patients with aeroallergen triggers (J B Wechsler, et al. Journal of asthma and allergy, 7:85-94, May 2014). An improved method to identify antigen triggers in EoE is needed.

Described herein are methods that can be used to identify antibodies in esophageal IgG and IgA obtained by brushing. The methods can predict accurately food-specific antibodies for determining EoE food triggers. The methods can also be used for monitoring treatment responses. The methods directly address the need for improved methods to identify causative antigens for EoE.

Methods

Disclosed herein are methods that can be used to identify a food sensitivity and/or a food allergy in a subject.

Disclosed herein are methods of detecting the binding of one or more food specific immunoglobulin (Ig) antibodies to one or more food antigens in a sample. In some aspects, the methods can comprise: contacting a sample obtained from a subject with one or more food antigens and detecting the binding of the one or more food specific Ig antibodies to the one or more food antigens. In some aspects, the methods can further comprise comparing the binding of the one or more food specific Ig antibodies to the one or more food antigens in the sample obtained prior to the subject consuming the food comprising the one or more of the food antigens to the sample obtained after the subject consumed the food comprising the one or more of the food antigens. In some aspects, the methods further comprise, diagnosing the subject with EoE. In some aspects, the methods further comprise, diagnosing the subject with EoE using the methods disclosed herein.

Disclosed herein are methods of detecting a food specific immune response in a sample. In some aspects, the method can comprise: a) contacting the sample with one or more food antigens; b) determining the presence of or level of one or more immunoglobulin (Ig) antibodies bound to the one or more food antigens; and c) comparing the level of the one or more Ig antibodies in the sample bound to the one or more food antigens in b) to the level of one or more Ig antibodies bound to the one or more food antigens in a reference sample; thereby detecting the food specific immune response in the sample when the level of the one or more Ig antibodies in the sample bound to the one or more food antigens is higher than the level of one or more Ig antibodies in a reference sample. In some aspects, the methods further comprise, diagnosing the subject with EoE. In some aspects, the methods further comprise, diagnosing the subject with EoE using the methods disclosed herein.

Disclosed herein are methods of identifying a food allergy in a subject with active or inactive eosinophilic esophagitis (EoE) in a subject suffering from EoE. In some aspects, the methods can comprise: a) detecting the presence of or level of one or more immunoglobulin (Ig) antibodies bound to the one or more food antigens in a sample; and b) comparing the level of the one or more Ig antibodies bound to the one or more food antigens in the sample to the level of one or more Ig antibodies bound to the one or more food antigens in a reference sample; wherein the level of the one or more Ig antibodies in the sample bound to the one or more food antigens is higher than the level of one or more Ig antibodies bound to the one or more food antigens in a reference sample identifies a food allergy in the subject. In some aspects, the methods further comprise, diagnosing the subject with EoE. In some aspects, the methods further comprise, diagnosing the subject with EoE using the methods disclosed herein.

Disclosed herein are methods of identifying a food sensitivity or hypersensitivity in a subject with active or inactive eosinophilic esophagitis (EoE) in a subject suffering from EoE. In some aspects, the methods can comprise: a) detecting the presence of or level of one or more immunoglobulin (Ig) antibodies bound to the one or more food antigens in a sample; and b) comparing the level of the one or more Ig antibodies bound to the one or more food antigens in the sample to the level of one or more Ig antibodies bound to the one or more food antigens in a reference sample; wherein the level of the one or more Ig antibodies in the sample bound to the one or more food antigens is higher than the level of one or more Ig antibodies bound to the one or more food antigens in a reference sample identifies a food sensitivity or hypersensitivity in the subject. In some aspects, the methods further comprise, diagnosing the subject with EoE. In some aspects, the methods further comprise, diagnosing the subject with EoE using the methods disclosed herein.

Disclosed herein are methods of identifying a sensitivity or hypersensitivity to an antigen in a subject with active or inactive eosinophilic esophagitis (EoE) in a subject suffering from EoE. In some aspects, the methods can comprise: a) detecting the presence of or level of one or more immunoglobulin (Ig) antibodies bound to the one or more antigens in a sample; and b) comparing the level of the one or more Ig antibodies bound to the one or more antigens in the sample to the level of one or more Ig antibodies bound to the one or more antigens in a reference sample; wherein the level of the one or more Ig antibodies in the sample bound to the one or more antigens is higher than the level of one or more Ig antibodies bound to the one or more antigens in a reference sample identifies a sensitivity or hypersensitivity to the one or more antigens in the subject. In some aspects, the methods further comprise, diagnosing the subject with EoE. In some aspects, the methods further comprise, diagnosing the subject with EoE using the methods disclosed herein.

Disclosed herein are methods of identifying a food allergy in a subject with irritable bowel syndrome. In some aspects, the methods can comprise: a) detecting the presence of or level of one or more immunoglobulin (Ig) antibodies bound to the one or more food antigens in a sample; and b) comparing the level of the one or more Ig antibodies bound to the one or more food antigens in the sample to the level of one or more Ig antibodies bound to the one or more food antigens in a reference sample; wherein the level of the one or more Ig antibodies in the sample bound to the one or more food antigens is higher than the level of one or more Ig antibodies bound to the one or more food antigens in a reference sample identifies a food allergy in the subject. In some aspects, the methods further comprise, diagnosing the subject with EoE. In some aspects, the methods further comprise, diagnosing the subject with EoE using the methods disclosed herein.

Disclosed herein are methods of treating a subject with active or inactive eosinophilic esophagitis (EoE) in a subject suffering from EoE. In some aspects, the methods can comprise: a) detecting the presence of or level of one or more immunoglobulin (Ig) antibodies bound to the one or more food antigens in a sample; b) comparing the level of the one or more Ig antibodies bound to the one or more food antigens in the sample to the level of one or more Ig antibodies bound to the one or more food antigens in a reference sample; and c) treating the subject. In some aspects, the methods further comprise, diagnosing the subject with EoE. In some aspects, the methods further comprise, diagnosing the subject with EoE using the methods disclosed herein.

Disclosed herein are methods of treating a subject with active eosinophilic esophagitis (EoE) in a subject suffering from EoE, the methods comprising: a) detecting the presence of or level of one or more immunoglobulin (Ig) antibodies bound to the one or more food antigens in a sample; b) comparing the level of the one or more Ig antibodies bound to the one or more food antigens in the sample to the level of one or more Ig antibodies bound to the one or more food antigens in a reference sample; and c) treating the subject. In some aspects, the methods further comprise, diagnosing the subject with EoE. In some aspects, the methods further comprise, diagnosing the subject with EoE using the methods disclosed herein.

Disclosed herein are methods of detecting the cause of an eosinophilic esophagitis (EoE) symptom. In some aspects, the EoE symptom can be caused by an immune response to an antigen in a patient diagnosed with or suffering from EOE. In some aspects, the methods can comprise obtaining or having obtained an esophageal mucosal sample from a subject. In some aspsects, the esophageal mucosal sample can be obtained from the subject is from the site of the immune response. In some aspects, the esophageal mucosal sample can comprise one or more immunoglobulin (Ig) antibodies. In some aspects, the methods can comprise contacting the sample with one or more antigens. In some aspects, the methods can comprise detecting the binding of the one or more specific Ig antibodies to the one or more antigens. In some aspects, the methods further comprise, diagnosing the subject with EoE using the methods disclosed herein. Examples of symptoms of EoE can include but is not limited to difficulty swallowing (dysphagia), food getting stuck in the esophagus after swalling (impaction), chest pain (often centrally located and does not respond to antacids), backflow of undigested food (regurgitation), vomiting, abdominal pain.

Disclosed herein are methods of diagnosing a subject with active or inactive EoE. Disclosed herein are methods of diagnosing a subject with active or inactive eosinophilic esophagitis (EoE) in a subject suffering from EoE. Disclosed herein are methods of diagnosing and treating subjects with active or inactive EoE. Disclosed herein are methods of diagnosing and treating a subject with active or inactive eosinophilic esophagitis (EoE) in a subject suffering from EoE. In some aspects, the methods can comprise detecting whether a level of IgA, IgE, IgM, IgD, IgG1, IgG2, IgG3 and/or IgG4 antibodies (or any combination thereof) is elevated in an esophageal secretion sample obtained from a subject. In some aspects, the methods can comprise diagnosing the subject with active EoE when the level of IgA, IgE, IgM, IgD, IgG1, IgG2, IgG3 and/or IgG4 antibodies in the sample is elevated above a pre-determined cut-off vale and diagnosing the subject with inactive EoE when the level of IgA, IgE, IgM, IgD, IgG1, IgG2, IgG3 and/or IgG4 antibodies in the sample are below a pre-determined cut-off value. In some aspects, the methods can comprise treating the subject diagnosed with active EoE, wherein when said level of IgA, IgE, IgM, IgD, IgG1, IgG2, IgG3 and/or IgG4 antibodies is below a pre-determined cut-off value, the subject is diagnosed with inactive EoE, and wherein the level IgA, IgE, IgM, IgD, IgG1, IgG2, IgG3 and/or IgG4 antibodies is above a pre-determined cut-off value, the subject is diagnosed with active EoE.

In some aspects, in any of the methods disclosed herein, the levels or amount of IgA, IgE, IgM, IgD, IgG1, IgG2, IgG3 and/or IgG4 antibodies (or any combination thereof) can be used to determine or diagnose active EoE. In some aspects, the methods can comprise comparing the levels or amount of IgA, IgE, IgM, IgD, IgG1, IgG2, IgG3 and/or IgG4 antibodies (or any combination thereof) from a sample from a subject to a reference sample or control to determine or diagnose active EoE. In some aspects, the methods can comprise comparing the levels or amount of IgA, IgE, IgM, IgD, IgG1, IgG2, IgG3 and/or IgG4 antibodies from a sample from a subject with active EoE to a sample from a subject with inactive EoE. In some aspects, the Ig antibodies can be IgG, IgA or a combination thereof. In some aspects, the Ig antibodies can be IgG4, IgA or a combination thereof. In some aspects, the methods can detect whether a level of any of IgA, IgE, IgM, IgD, IgG1, IgG2, IgG3 and/or IgG4 antibodies is elevated (increased) in an esophageal secretion sample obtained from the subject. In some aspects, the subject can be diagnosed with EoE or active EoE when the measured IgA, IgE, IgM, IgD, IgG1, IgG2, IgG3 and/or IgG4 antibody level is elevated above a pre-determined cut-off value or diagnosed with inactive EoE when the IgA, IgE, IgM, IgD, IgG1, IgG2, IgG3 and/or IgG4 antibody level in the sample is below a pre-determined cut-off value. In some aspects, the pre-determined cut-off value can be about 25 ng/ml for IgE. In some aspects, when the IgE antibody level is below about 25 ng/ml, the subject is diagnosed with inactive EoE. In some aspects, the pre-determined cut-off value can be about 5000 ng/ml for IgA. In some aspects, when the IgA antibody level is below about 5000 ng/ml, the subject is diagnosed with inactive EoE. In some aspects, the pre-determined cut-off value can be about 1000 ng/ml for IgM. In some aspects, when the IgM antibody level is below about 1000 ng/ml, the subject is diagnosed with inactive EoE. In some aspects, the pre-determined cut-off value can be about 200 ng/ml for IgG1. In some aspects, when the IgG1 antibody level is below about 200 ng/ml, the subject is diagnosed with inactive EoE. In some aspects, the pre-determined cut-off value can be about 50 ng/ml for IgG2. In some aspects, when the IgG2 antibody level is below about 50 ng/ml, the subject is diagnosed with inactive EoE. In some aspects, the pre-determined cut-off value can be about 4000 ng/ml for IgG3. In some aspects, when the IgG3 antibody level is below about 4000 ng/ml, the subject is diagnosed with inactive EoE. In some aspects, the pre-determined cut-off value can be about 6000 ng/ml for IgG4. In some aspects, when the IgG4 antibody level is below about 6000 ng/ml, the subject is diagnosed with inactive EoE.

For example, IgA found along esophageal mucosal surface can be easily collected and demonstrates reactivity towards common trigger foods in EoE. In fact, IgA was significantly elevated to causative foods in EoE patients. Trigger foods were commonly elevated 1.5 times non trigger foods for IgA and routinely demonstrated response values greater than 340 response units (a concentration of 0.01mg/l in a 1:50 dilution). Specific foods such as gluten and dairy demonstrated similar results in their respective categories. In fact, a positive cutoff of 340 RV (response values, 0.01 mg/l), was over 91% accurate in predicting trigger foods with both high sensitivity (86%) and specificity (98%).

Disclosed herein are methods of treating a subject with irritable bowel syndrome. In some aspects, the methods can comprise: a) detecting the presence of or level of one or more immunoglobulin (Ig) antibodies bound to the one or more food antigens in a sample; b) comparing the level of the one or more Ig antibodies bound to the one or more food antigens in the sample to the level of one or more Ig antibodies bound to the one or more food antigens in a reference sample; and c) treating the subject. In some aspects, the methods further comprise, diagnosing the subject with EoE. In some aspects, the methods further comprise, diagnosing the subject with EoE using the methods disclosed herein.

Disclosed herein are methods of diagnosing and treating a subject with active or inactive eosinophilic esophagitis (EoE) in a subject suffering from EoE. In some aspects, the methods can comprise: a) detecting the presence of or level of one or more one or more immunoglobulin (Ig) antibodies bound to the one or more food antigens in a sample; b) comparing the level of the one or more Ig antibodies bound to the one or more food antigens in the sample to the level of one or more Ig antibodies bound to the one or more food antigens in a reference sample; c) diagnosing the subject with active EoE when the level of the one or more Ig antibodies in the sample bound to the one or more food antigens is higher than the level of one or more Ig antibodies bound to the one or more food antigens in a reference sample and diagnosing the subject with inactive EoE when the level of the one or more Ig antibodies in the sample bound to the one or more food antigens is lower than the level of one or more Ig antibodies bound to the one or more food antigens in a reference sample level; and d) treating the subject diagnosed with active EoE, wherein the level of the one or more Ig antibodies in the sample bound to the one or more food antigens is higher than the level of one or more Ig antibodies bound to the one or more food antigens in a reference sample.

Also disclosed herein are methods of detecting the binding of one or more specific immunoglobulin (Ig) antibodies to one or more antigens in a sample. In some aspects, the methods can comprise: contacting a sample obtained from a subject with one or more antigens and detecting the binding of the one or more specific Ig antibodies to the one or more food antigens. In some aspects, the one or more antigens can be immobilized on a solid support. In some aspects, the sample can be obtained before the subject is exposed to one or more of the antigens. In some aspects, the methods further comprise, diagnosing the subject with EoE. In some aspects, the methods further comprise, diagnosing the subject with EoE using the methods disclosed herein.

Disclosed herein are methods for diagnosing and/or treating eosinophilic esophagitis in a subject in need thereof. In some aspects, the methods can comprise: (i) measuring the gene expression level for at least one gene in an esophageal biopsy sample from the patient, wherein the at least one protein or at least one gene selected from the group consisting of: eosinophil peroxidase, periostin, Eotaxin-3, stem cell factor, or CCL26, KITLG, and POSTN, wherein the measuring the protein or gene expression level is performed by a method comprising DNA microarray analysis, polymerase chain reaction analysis, or both; (ii) comparing the protein or gene expression level for the at least one protein or the at least one gene to its expression level in an esophageal biopsy sample from a normal individual defined as having zero eosinophils per high power field and no basal layer expansion; (iii) diagnosing eosinophilic esophagitis in the subject where the expression level of the at least one protein or the at least one gene is increased more than 10-fold compared to its expression level in the esophageal biopsy sample from a normal individual, and (iv) treating the eosinophilic esophagitis in the subject diagnosed according to step (iii) with one or more therapies selected from an anti-inflammatory therapy, allergen elimination, a cytokine inhibitor, a corticosteroid, an immunosuppressant, and a complement inhibitor.

Disclosed herein are methods of diagnosing eosinophilic esophagitis (EoE) by detecting one or more biomarkers selected from the group consisting of eosinophil peroxidase, periostin, Eotaxin-3, stem cell factor, or CCL26, KITLG, and POSTN.

In some aspects, the treatment step can comprise administering to the subject one or more monoclonal agglutinating anti-IgA antibodies, anti-inflammatory therapy, allergen elimination, a cytokine inhibitor, an immunosuppressant, bovine Ig, a complement inhibitor, one or more steroids (e.g., corticosteroids), or a combination thereof.

In some aspects, the treatment step can comprise modifation of intake (e.g. a change in diet) or withdrawal of one or more food types or food components from the subject's diet. In some aspects, the one or more food types or food components can be any food or food components the subject might consume that may correlate with the one or more food allergens detected using the methods disclosed herein. In some aspects, a dietary change or withdrawal of one or more more food types or food components can be based on the detection of the one or more Ig antibodies. In some aspects, the food types can be milk, wheat, soy, and eggs. In some aspects, the one or more food antigens can be wheat f1, soybean f14, casein f78, eggf245, or a combination thereof. In some aspects, the treatment step can comprise withdrawal of one or more food components from the subject's intake. In some aspects, the one or more food components can be any food component found in any food type the subject might consume. In some aspects, the food component can be casein, whey, emulsfifiers, species, pollutants, aerollergens, dust mites and the like.

In some aspects, the methods disclosed herein can further comprise detecting EoE in the subject prior to the detecting step. In some aspects, EoE can be detected in the subject by detecting an eosinophil granule protein in the mucosal tissue of the esophagus in the subject. In some aspects, the methods can comprise administering to the subject radiolabeled heparin under conditions wherein the radiolabeled heparin binds to an eosinophil granule protein to form a radiolabeled heparin/eosinophil granule protein complex, and detecting the radiolabeled heparin/eosinophil granule protein complex in the mucosal tissue of the esophagus, whereby detecting the radiolabeled heparin/eosinophil granule protein complex in the mucosal tissue of the esophagus detects eosinophilic esophagitis in the subject.

In some aspects, the methods can be specific for a single antigen or a single food (e.g., cow's milk) or food component. A single food is an antigenically complex mixture (e.g., cow's milk contains many antigens). In some aspects, the methods can detect or identify a specific single antigen or a specific single food antigen on the bead (or other carrier) or detect or identify two or more (or a plurality of) antigens or food antigens on one bead or detect or identify one or more (or a plurality of) antigens or food antigens on two or more beads. For example, the Luminex device can analyze 100 or antigens in a single test. In some aspects, the methods can be specific for two or more single antigens or single food antigens. In some aspects, the single antigens can be a combination of food antigens and environmental antigens.

In some aspects, the antigen can be a food antigen. In some aspects, the antigen can be an environmental antigen. In some aspects, the environmental antigen can be pollen, fungi, dander (e.g., cat dander), dust mites, animal emanations, insect emanations, and the like. In some aspects, the antigen can be an aeroallergen. In some aspects, the aeroallergen can be pollen, spores, mold, animal dander or an insect-derived antigen. In some aspects, the antigen can be an antigen component. For example, the antigen can be a component of milk (e.g., casein can be detected as the protein in dairy that is the cause of the increase in immunoglobulins detected, and not whey). In some aspects, the antigen can be a causative antigen. In some aspects, the causative antigen can be a food antigen, an environmental antigen, an aerollergen, or an antigen component.

In some aspects, the level of the one or more specific Ig antibodies bound to the one or more antigens can be higher in the sample compared to the level of the one or more specific Ig antibodies bound to the one or more antigens in a reference sample, indicating a specific immune response to the antigen.

In some aspects, the level of the one or more food specific Ig antibodies bound to the one or more food antigens can be higher in the sample compared to the level of the one or more food specific Ig antibodies bound to the one or more food antigens in a reference sample, indicating a food specific immune response.

In some aspects, the one or more antigens can be immobilized on a solid support. In some aspects, the one or more food antigens can be immobilized on a solid support. In some aspects, the one or more environmental antigens can be immobilized on a solid support.

An array is a form of solid support. An array detector is also a form of solid support to which multiple different capture compounds or detection compounds have been coupled in an array, grid, or other organized pattern.

Solid-state substrates for use in solid supports can include, for instance, any solid material to which molecules can be coupled. Examples of such materials include acrylamide, agarose, cellulose, nitrocellulose, glass, polystyrene, polyethylene vinyl acetate, polypropylene, polymethacrylate, polyethylene, polyethylene oxide, polysilicates, polycarbonates, teflon, fluorocarbons, nylon, silicon rubber, polyanhydrides, polyglycolic acid, poly lactic acid, polyorthoesters, polypropylfumerate, collagen, glycosaminoglycans, and polyamino acids. Solid-state substrates can have any useful form including thin film, membrane, bottles, dishes, fibers, woven fibers, shaped polymers, particles, beads, microparticles, or any combination thereof. Solidstate substrates and solid supports can be porous or nonporous. An example of a solid-state substrate is a microtiter dish (e.g., a standard 96-well type). A multiwell glass slide can also be used. For example, such as one containing one array per well can be used, allowing for greater control of assay reproducibility, increased throughput and sample handling, and ease of automation.

The different compounds and components disclosed herein can be used together as a set. The set can be used as a mixture of all or subsets of the compounds used separately in separate reactions, or immobilized in an array. Compounds used separately or as mixtures can be physically separable through, for example, association with or immobilization on a solid support. An array can include a plurality of compounds immobilized at identified or predefined locations on the array. Each predefined location on the array can generally have one type of component (that is, all the components at that location are the same). Each location can have multiple copies of the component. The spatial separation of different components in the array allows separate detection and identification of the polynucleotides or polypeptides disclosed herein.

It is not required that a given array be a single unit or structure. The set of compounds can be distributed over any number of solid supports. For example, each compound can be immobilized in a separate reaction tube or container, or on separate beads or microparticles. Different aspects of the disclosed method and use of the gene expression panel or array or diagnostic device can be performed with different components (e.g., different compounds specific for different proteins) immobilized on a solid support.

Some solid supports can have capture compounds, such as antibodies, attached to a solid-state substrate. Such capture compounds can be specific for calcifying nanoparticles or a protein on calcifying nanoparticles. Captured calcified nanoparticles or proteins can then be detected by binding of a second detection compound, such as an antibody. The detection compound can be specific for the same or a different protein on the calcifying nanoparticle.

Methods for immobilizing nucleic acids, peptides or antibodies (and other proteins) to solid-state substrates are well established. Immobilization can be accomplished by attachment, for example, to aminated surfaces, carboxylated surfaces or hydroxylated surfaces using standard immobilization chemistries. Examples of attachment agents are cyanogen bromide, succinimide, aldehydes, tosyl chloride, avidinbiotin, photocrosslinkable agents, epoxides, maleimides and N[y-Maleimidobutyryloxy] succinimide ester (GMBS), and a heterobifunctional crosslinker. Antibodies can be attached to a substrate by chemically cross-linking a free amino group on the antibody to reactive side groups present within the solid-state substrate. Antibodies can be, for example, chemically cross-linked to a substrate that contains free amino, carboxyl, or sulfur groups using glutaraldehyde, carbodiimides, or GMBS, respectively, as cross-linker agents. In this method, aqueous solutions containing free antibodies can be incubated with the solid-state substrate in the presence of glutaraldehyde or carbodiimide.

A method for attaching antibodies or other proteins to a solid-state substrate is to functionalize the substrate with an amino- or thiol-silane, and then to activate the functionalized substrate with a homobifunctional cross-linker agent such as (Bis-sulfo-succinimidyl suberate (BS3) or a heterobifunctional cross-linker agent such as GMBS. For cross-linking with GMBS, glass substrates can be chemically functionalized by immersing in a solution of mercaptopropyltrimethoxysilane (1% vol/vol in 95% ethanol pH 5.5) for 1 hour, rinsing in 95% ethanol and heating at 120° C. for 4 hrs. Thiol-derivatized slides can be activated by immersing in a 0.5 mg/ml solution of GMBS in 1% dimethylformamide, 99% ethanol for 1 hour at room temperature. Antibodies or proteins can be added directly to the activated substrate, which can be blocked with solutions containing agents such as 2% bovine serum albumin, and air-dried. Other standard immobilization chemistries are known by those of ordinary skill in the art.

Each of the components (e.g., compounds) immobilized on the solid support can be located in a different predefined region of the solid support. Each of the different predefined regions can be physically separated from each other. The distance between the different predefined regions of the solid support can be either fixed or variable. For example, in an array, each of the components can be arranged at fixed distances from each other, while components associated with beads will not be in a fixed spatial relationship. The use of multiple solid support units (e.g., multiple beads) can result in variable distances.

Components can be associated or immobilized on a solid support at any density. Components can be immobilized to the solid support at a density exceeding 400 different components per cubic centimeter. Arrays of components can have any number of components. For example, an array can have at least 1,000 different components immobilized on the solid support, at least 10,000 different components immobilized on the solid support, at least 100,000 different components immobilized on the solid support, or at least 1,000,000 different components immobilized on the solid support.

In some aspects, the sample can be obtained before the subject is exposed to a particular antigen (e.g., food antigen or environmental antigen). In some aspects, the sample can comprise one or more one or more antigen specific Ig antibodies. In some aspects, the sample can be obtained before the subject consumes a food comprising one or more of the food antigens. In some aspects, the methods can further comprise obtaining or have obtained the sample from a subject. In some aspects, the sample can comprise one or more one or more food specific Ig antibodies. In some aspects, the Ig antibodies can be IgA, IgD, IgE, IgG, IgM or a combination thereof. In some aspect, the IgA antibody can be IgA1, IgA2 or a combination thereof. In some aspects, the IgG antibody can be IgG1, IgG2, IgG3, IgG4 or a combination thereof. In some aspects, the sample can be a mucosal sample. In some aspects, the mucosal sample can be an esophageal secretion. In some aspects, the sample can be a mucosal fluid. In some aspects, the sample can be the effluent from the esophageal disease. In some aspects, the sample can be the effluent from the small bowel.

In some aspects, the subject has active eosinophilic esophagitis. In some aspects, the subject has resolved eosinophilic esophagitis. In some aspects, the subject has at least one symptom of eosinophilic esophagitis. In some aspects, the subject has irritable bowel syndrome. In some aspects, the subject has at least one symptom of irritable bowel syndrome.

In some aspects, the one or more food specific Ig antibodies can be IgG, IgA, IgD, IgE, IgM or a combination thereof. In some aspects, the one or more food-specific Ig antibodies can be IgG, IgA, IgE, or a combination thereof. In some aspects, the one or more food-specific Ig antibodies can be IgG, IgA, or a combination thereof. In some aspects, the one or more food-specific Ig antibodies can be IgG4, IgA, or a combination thereof As used herein, the term "expression," when used in the context of determining or detecting the expression or expression level of one or more genes, can refer to determining or detecting transcription of the gene (i.e., determining mRNA levels) and/or determining or detecting translation of the gene (e.g., determining or detecting the protein produced). To determine the expression level of a gene means to determine whether or not a gene is expressed, and if expressed, to what relative degree.

The expression level of one or more genes disclosed herein can be determined directly (e.g., immunoassays, mass spectrometry) or indirectly (e.g., determining the mRNA expression of a protein or peptide). Examples of mass spectrometry include ionization sources such as EI, CI, MALDI, ESI, and analysis such as Quad, ion trap, TOF, FT or combinations thereof, spectrometry, isotope ratio mass spectrometry (IRMS), thermal ionization mass spectrometry (TIMS), spark source mass spectrometry, Multiple Reaction Monitoring (MRM) or SRM. Any of these techniques can be carried out in combination with prefractionation or enrichment methods. Examples of immunoassays include immunoblots, Western blots, Enzyme linked Immunosorbant Assay (ELISA), Enzyme immunoassay (EIA), radioimmune assay.

Immunoassay methods use antibodies for detection and determination of levels of an antigen are known in the art. The antibody or antigen can be immobilized on a solid support such as a stick, plate, bead, microbead or array.

Expression levels of one or more of the genes described herein can be also be determined indirectly by determining the mRNA expression for the one or more genes in a tissue sample. RNA expression methods include but are not limited to extraction of cellular mRNA and Northern blotting using labeled probes that hybridize to transcripts encoding all or part of the gene, amplification of mRNA using gene-specific primers, polymerase chain reaction (PCR), and reverse transcriptase-polymerase chain reaction (RT-PCR), followed by quantitative detection of the gene product by a variety of methods; extraction of RNA from cells, followed by labeling, and then used to probe cDNA or olignonucleotides encoding the gene, in situ hybridization; and detection of a reporter gene.

Methods to measure protein expression levels include but are not limited to Western blot, immunoblot, ELISA, radioimmunoassay, immunoprecipitation, surface plasmon resonance, chemiluminescence, fluorescent polarization, phosphorescence, immunohistochemical analysis, microcytometry, microarray, microscopy, fluorescence activated cell sorting (FACS), and flow cytometry. The method can also include specific protein property-based assays based including but not limited to enzymatic activity or interaction with other protein partners. Binding assays can also be used, and are well known in the art. For instance, a BIAcore machine can be used to determine the binding constant of a complex between two proteins. Other suitable assays for determining or detecting the binding of one protein to another include, immunoassays, such as ELISA and radioimmunoassays. Determining binding by monitoring the change in the spectroscopic can be used or optical properties of the proteins can be determined via fluorescence, UV absorption, circular dichroism, or nuclear magnetic resonance (NMR). Alternatively, immunoassays using specific antibody can be used to detect the expression of a particular protein in sample.

Reference mRNA expression level. As used herein, the term "reference," "reference expression," "reference sample," "reference value," "control," "control sample" and the like, when used in the context of a sample or expression level of one or more genes or proteins refers to a reference standard wherein the reference is expressed at a constant level among different (i.e., not the same tissue, but multiple tissues) tissues, and is unaffected by the experimental conditions, and is indicative of the level in a sample of a predetermined disease status (e.g., not suffering from EoE or active EoE, IBS or an immune response after exposure to a specific antigen). The reference value can be a predetermined standard value or a range of predetermined standard values, representing no illness, or a predetermined type or severity of illness.

Reference expression can be the level of the one or more genes described herein in a reference sample from a subject, or a pool of subjects, not suffering from suffering from EoE or active EoE, IBS or an immune response after exposure to a specific antigen or from a predetermined severity or type of EoE, IBS or an immune response after exposure to a specific antigen. In some aspects, the reference value is the level of one or more genes disclosed herein in the tissue of (or sample from) a subject, or subjects, wherein the subject or subjects is not suffering from EoE or active EoE, IBS or an immune response after exposure to a specific antigen.

Comparing the expression level of one or more genes disclosed herein. By comparing the expression level for one or more of, for example, CCL26, KITLG, and POSTN with the reference expression level for, for example, CCL26, KITLG, and POSTN, it is possible to determine active EoE in a subject.

Determining the expression level of one or more genes disclosed herein can include determining whether the gene is upregulated or increased as compared to a control or reference sample, downregulated or decreased compared to a control or reference sample, or unchanged compared to a control or reference sample. As used herein, the terms, "upregulated" and "increased expression level" or "increased level of expression" refers to a sequence corresponding to one or more genes disclosed herein that is expressed wherein the measure of the quantity of the sequence exhibits an increased level of expression when compared to a reference sample or "normal" control. In some aspects, the normal control can refer to subjects that do not have EoE. In some aspects, the normal control can refer to subjects with resolved EoE. For example, the terms, "upregulated" and "increased expression level" or "increased level of expression" refers to a sequence corresponding to one or more genes disclosed herein that is expressed wherein the measure of the quantity of the sequence exhibits an increased level of expression of one or more of eosinophil peroxidase, periostin, Eotaxin-3, and stem cell factor protein(s) and/or mRNA when compared to the expression of the same mRNA(s) from a reference sample or "normal" control. An "increased expression level" refers to an increase in expression of at least 1%, 2%, 3%, 4%, 5%, 6%, 7%, 8%, 9%, 10% or more, for example, 20%, 30%, 40%, or 50%, 60%, 70%, 80%, 90% or more, or greater than 1-fold, up to 2-fold, 3-fold, 4-fold, 5-fold, 10-fold, 50-fold, 100-fold or more. As used herein, the terms "downregulated," "decreased level of expression," or "decreased expression level" refers to a sequence corresponding to one or more genes disclosed herein that is expressed wherein the measure of the quantity of the sequence exhibits a decreased level of expression when compared to a reference sample or "normal" control For example, the terms "downregulated," "decreased level of expression," or "decreased expression level" refers to a sequence corresponding to one or more genes disclosed herein that is expressed wherein the measure of the quantity of the sequence exhibits a decreased level of expression of one or more of eosinophil peroxidase, periostin, Eotaxin-3, and stem cell factor protein(s) and/or mRNA when compared to the expression of the same mRNA(s) from a reference sample or "normal" control. A "decreased level of expression" refers to a decrease in expression of at least 1%, 2%, 3%, 4%, 5%, 6%, 7%, 8%, 9%, 10% or more, for example, 20%, 30%, 40%, or 50%, 60%, 70%, 80%, 90% or more, or greater than 1-fold, up to 2-fold, 3-fold, 4-fold, 5-fold, 10-fold, 50-fold, 100-fold or more.

Determining active EoE. As described herein, samples from a subject can be compared with reference samples to determine the expression ratio to determine whether a subject has active EoE. The reference samples can be from subjects having "normal" levels of one or more of the following genes, CCL26, KITLG, and POSTN. Suitable statistical and other analysis can be carried out to confirm a change (e.g., an increase or a higher level of expression) in one or more of CCL26, KITLG, and POSTN when compared with a reference sample, wherein a ratio of the sample expression level of one or more of CCL26, KITLG, and POSTN to the reference expression level of one or more of CCL26, KITLG, and POSTN indicates higher expression level of one or more of CCL26, KITLG, and POSTN in the sample. In some aspects, the ratio of the sample expression level of two or more, of CCL26, KITLG, and POSTN to the reference expression level of two or more of CCL26, KITLG, and POSTN indicates higher expression level of two or more of CCL26, KITLG, and POSTN in the sample, indicating that the subject has an active EoE.

A higher or increased expression level of one or more of CCL26, KITLG, and POSTN when compared to the reference expression level of CCL26, KITLG, and POSTN can indicate active EoE. Signature pattern(s) of increased (higher) or decreased (lower) sample expression levels of one or more of CCL26, KITLG, and POSTN when compared to the reference expression levels of one or more of CCL26, KITLG, and POSTN can be observed and indicate the active EoE in a subject.

The expression level of one or more genes described herein can be a measure of one or more genes, for example, per unit weight or volume. In some aspects, the expression level can be a ratio (e.g., the amount of one or more genes in a sample relative to the amount of the one or more markers of a reference value).

In some aspects, samples from a subject can be compared with reference samples to determine the percent change to determine whether a subject has active EoE. In other words, the expression level can be expressed as a percent. For example, the percent change in the expression levels of one or more genes, wherein the expression level of one (or two) or more of CCL26, KITLG, and POSTN is increased (or is higher) by 10%, 15%, 20%, 25%, 30%, 35%, 40%, 45%, 50%, 55%, 60%, 65%, 70%, 75%, 80%, 85%, 90%, 95%, or 100% when compared to the reference expression level of CCL26, KITLG, and POSTN, indicating active EoE. Alternatively, the percent change in the expression levels of one or more genes can be decreased (or lower) by 10%, 15%, 20%, 25%, 30%, 35%, 40%, 45%, 50%, 55%, 60%, 65%, 70%, 75%, 80%, 85%, 90%, 95%, or 100% when compared to a reference expression level.

In some aspects, an increase or decrease or some combination thereof in the expression level of genes or proteins other than those disclosed herein can indicate active or resolved EoE or a diagnosis of EoE or active EoE in a subject. In some aspects, a signature pattern of increased or decreased expression levels of one or more of the genes or proteins disclosed herein is indicative.

Diagnostic Device

Disclosed herein, is a diagnostic device for diagnosing eosinophilic esophagitis in a subject (e.g., human). In some aspects, a sample of mucosa or esophageal secretions can be obtained from the subject and the level or expression level in the sample can be compared with a reference value.

The diagnostic device can include one or more biomarkers. In some aspects, the biomarker can be an antigen or antibody. In some aspects, biomarkers can bind to or hybridize with one or more genes, RNA products or peptides disclosed herein. As used herein, the terms "marker" or "biomarker" refers to detectable or measurable substance (e.g., antigen, antibody, gene, gene product, protein, etc.) in a sample that can indicate a biological state, disease, condition, predict a clinical outcome, etc. In some aspects, biomarkers can be eosinophil peroxidase, periostin, Eotaxin-3, stem cell factor, or CCL26, KITLG, and POSTN or a fragment thereof, or an antibody or fragment thereof which binds one or more of the biomarkers. The diagnostic device can be incorporated into a kit for diagnosing EoE or active EoE in a subject.

Protein Array

Disclosed herein are polypeptide or protein arrays. In some aspects, the protein arrays can comprise probes including antigens, antibodies, aptamers, and other cognate binding ligands specific to a component of the gene panels disclosed herein. Protein arrays and methods of constructing the protein arrays are well known to one of ordinary skill in the art.

One type of protein array that can be suitable uses an immobilized "capture antibody." The polypeptides are bound to a solid substrate (e.g., glass) with a treated surface (e.g., aminosilane) or through a biotin-streptavidin conjugation. The arrays are then incubated with a solution containing probe that can bind to the capture antibodies in a manner dependent upon time, buffer components, and recognition specificity. The probes can then be visualized directly if they have been previously labeled, or can be bound to a secondary labeled reagent (e.g., another antibody). The amount of probe bound to the capture antibody that is visualized can depend upon the labeling method utilized; generally, a CCD imager or laser scanner that uses filter sets that are appropriate to excite and detect the emissions of the label can be used. The imager converts the amount of detected photons into an electronic signal (often an 8-bit or 16-bit scale) that can be analyzed using commercially available software packages.

The substrate of the array can be organic or inorganic, biological or non-biological or any combination of these materials. The substrate can be transparent or translucent. Examples of materials suitable for use as a substrate in the array include silicon, silica, quartz, glass, controlled pore glass, carbon, alumina, titanium dioxide, germanium, silicon nitride, zeolites, and gallium arsenide; and metals including gold, platinum, aluminum, copper, titanium, and their alloys. Ceramics and polymers can also be used as substrates. Suitable polymers include, but are not limited to polystyrene; poly(tetra)fluorethylene; (poly)vinylidenedifluoride; polycarbonate; polymethylmethacrylate; polyvinylethylene; polyethyleneimine; poly(etherether)ketone; polyoxymethylene (POM); polyvinylphenol; polylactides; polymethacrylimide (PM I); polyalkenesulfone (PAS); polyhydroxyethylmethacrylate; polydimethylsiloxane; polyacrylamide; polyimide; co-block-polymers; and Eupergit®. Photoresists, polymerized Langmuir-Blodgett films, and LIGA structures can also serve as substrates.

The array can further comprise a coating that can be formed on the substrate or applied to the substrate. The substrate can be modified with a coating by using thin-film technology based on either physical vapor deposition (PVD) or plasma-enhanced chemical vapor deposition (PECVD).

Alternatively, plasma exposure can be used to directly activate the substrate. For instance, plasma etch procedures can be used to oxidize a polymeric surface (i.e. polystyrene or polyethylene to expose polar functionalities such as hydroxyls, carboxylic acids, aldehydes and the like).

The coating can comprise a metal film. Examples of metal films include aluminum, chromium, titanium, nickel stainless steel zinc, lead, iron, magnesium, manganese, cadmium, tungsten, cobalt, and alloys or oxides thereof. In some aspects, the metal film can be a noble metal film. Examples of noble metals that can be used for a coating include, but are not limited to, gold, platinum, silver, copper, and palladium. In some aspects, the coating comprises gold or a gold alloy. Electron-beam evaporation can be used to provide a thin coating of gold on the surface. In some aspects, the metal film can from about 50 nm to about 500 nm in thickness.

Alternatively, the coating can be silicon, silicon oxide, silicon nitride, silicon hydride, indium tin oxide, magnesium oxide, alumina, glass, hydroxylated surfaces, and a polymer.

The arrays described herein can comprise a collection of addressable elements. Such elements can be spatially addressable, such as arrays contained within microtiter plates or printed on planar surfaces wherein each element can be present at distinct X and Y coordinates. Alternatively, elements can be addressable based on tags, beads, nanoparticles, or physical properties. The microarrays can be prepared according to the methods known to one of ordinary skill in the art. The term "arrays" as used herein can refer to any biologic assay with multiple addressable elements. In some aspects, the addressable elements can be polypeptides (e.g., antibodies or fragments thereof) or nucleic acid probes. As used herein, "elements" refer to any probe (polypeptide or nucleic acid based) that can be bound by an organ-specific polypeptide, polypeptide fragment or transcript encoding such polypeptides, as related or associated with any of the gene or proteins disclosed herein. Molecules can be, but are not limited to, proteins, polypeptides, peptides, RNA, DNA, lipids, glycosylated molecules, carbohydrates, polypeptides with phosphorylation modifications, and polypeptides with citrulline modifications, aptamers, oxidated molecules, and other molecules.

For the elements described herein, "addressability" refers to the location, position, tags, cleavable tags or markers, identifiers, spectral properties, electrophoretic properties, or other physical properties that enable identification of the element. An example of addressability, also known as coding, is spatial addressability, where the position of the molecule is fixed, and that position is correlated with the identity. This type of spatial array can generally be synthesized or spotted onto a planar substrate, producing, for example, microarrays, where a large number of different molecules are densely laid out in a small area (e.g. comprising at least about 400 different sequences per cm$^2$, and can be 1000 sequences per cm$^2$ or as many as 5000 sequences per cm$^2$, or more). Less dense arrays (e.g., ELISA or RIA plates) where wells in a plate each contain a distinct probe can comprise from about 96 sequences per plate, up to about 100 sequences per cm2, up to the density of a microarray. Other spatial arrays utilize fiber optics, where distinct probes can be bound to fibers, which can be formed into a bundle for binding and analysis. Methods for the manufacture and use of spatial arrays of polypeptides are known in the art.

An alternative to this type of spatial coding array is the use of molecular "tags," where the target probes can be attached to a detectable label, or tag, which can provide coded information about the sequence of the probe. These tags can be cleaved from the element, and subsequently detected to identify the element. In some aspects, a set of probes can be synthesized or attached to a set of coded beads, wherein each bead can be linked to a distinct probe, and wherein the beads can be coded in a manner that allows identification of the attached probe. In this type of "tag array," flow cytometry can be used for detection of binding. For example, microspheres having fluorescence coding and can identify a particular microsphere. The probe can be covalently bound to a "color coded" object. A labeled target polypeptide can be detected by flow cytometry, and the coding on the microsphere can be used to identify the bound probe (e.g., immunoglobulin, antigen binding fragments of immunoglobulins, or ligands).

In some aspects, the array can be an array comprising one or more antigens (e.g. environmental or food antigens or allergens). In some aspects, the array can be an immunoglobulin array (e.g., an array comprising antibody or antigen-binding fragment thereof). As used herein, an "immunoglobulin array" refers to a spatially separated set of discrete molecular entities capable of binding to target polypeptides arranged in a manner that allows identification of the polypeptides contained within the sample. In some aspects, the array can comprise one or more of proteins, polypeptides, peptides, RNA, DNA, lipid, glycosylated molecules, polypeptides with phosphorylation modifications, and polypeptides with citrulline modifications, aptamers, and other molecules.

Kits

In some aspects, kits are provided for measuring one or more immunoglobulins in a sample. In some aspects, kits are provided for measuring the RNA (e.g., a RNA product) of one or more biomarkers disclosed herein. The kits can comprise materials and reagents that can be used for measuring the expression of the RNA of one or more biomarkers. Examples of suitable kits include RT-PCR or microarray. These kits can include the reagents needed to carry out the measurements of the RNA expression levels. Alternatively, the kits can further comprise additional materials and reagents. For example, the kits can comprise materials and reagents required to measure RNA expression levels of any number of genes up to 1, 2, 3, 4, 5, 10, or more genes that are not biomarkers disclosed herein.

Gene Expression Panel

Disclosed herein are gene expression panels and arrays for diagnosing EoE or active EoE in a subject (e.g., human) consisting of primers or probes capable of detecting one or more genes disclosed herein. The disclosed gene expression panels or arrays can comprise any of the genes disclosed herein. For example, the gene expression panel or array can be used to detect one or more of CCL26, KITLG, and POSTN. In some aspects, the gene expression panels or arrays can comprise CCL26, KITLG, and POSTN.

In some aspects, the sample can be an esophageal biopsy, mucosal sample or an esophageal secretion.

The gene expression panels or arrays disclosed herein can consist of primers or probes capable of detecting or amplifying any number of the genes disclosed herein. The gene expression panels or arrays disclosed herein can further comprise primers or probes capable of detecting or amplifying any number of genes not disclosed herein. For example, the primers or probes can detect or amplify between 1 and 5, 5 and 10, 10 and 100, or more, or any variation in between.

The gene expression panels or arrays disclosed herein can be used as a standalone method for assessing EoE in a subject or in combination with one or more other gene expression panels or arrays not disclosed herein. They can be used along with one or more diagnostic test. In some aspects, the gene expression panels or arrays can further comprise a second diagnostic test. The gene expression panels or arrays disclosed herein can also be used in methods to generate a specific profile. The profile can be provided in the form of a heatmap or boxplot.

The profile of the gene expression levels can be used to compute a statistically significant value based on differential expression of the one or more genes disclosed herein, wherein the computed value correlates to a diagnosis for a subtype of EoE. The variance in the obtained profile of expression levels of the said selected genes or gene expression products can be either upregulated or downregulated in subjects with an increased susceptibility compared to a reference subject or control. The Examples section provides additional detail. For instance, when the expression level of one or more of CCL26, KITLG, and POSTN are upregulated, indicating EoE or active EoE. As described herein, one of ordinary skill in the art can use a combination of any of genes disclosed herein to form a profile that can then be used to assess EoE or active EoE, or to determine (and diagnose) whether a subject has EoE or active EoE.

Disclosed herein are methods of diagnosing EoE using the gene expression panel or array described herein.

In some aspects, the gene expression panel or array disclosed herein can be used to determine or assess EoE or active EoE in a subject, wherein the expression level for CCL26, KITLG, or POSTN in the sample is compared to a reference expression level for CCL26, KITLG, or POSTN. In some aspects, the gene expression panel or array disclosed herein can be used to determine or assess EoE or active EoE in a subject, wherein a ratio (or percent change) of the sample expression level of one or more of CCL26, KITLG, or POSTN to the reference expression level of one or more of CCL26, KITLG, or POSTN indicates higher expression level of one or more of CCL26, KITLG, or POSTN in the sample. In some aspects, the ratio (or percent change) of the sample expression level of two or more of CCL26, KITLG, or POSTN to the reference expression level of two or more of CCL26, KITLG, or POSTN indicates higher expression level of two or more of CCL26, KITLG, or POSTN in the sample, indicating that the subject has an EoE or active EoE. Suitable statistical and other analysis can be carried out to confirm a change (e.g., an increase or a higher level of expression) in one or more of CCL26, KITLG, or POSTN when compared with a reference sample.

The gene expression panel or array can consist of primers or probes capable of detecting, amplifying or otherwise measuring the presence or expression of one or more genes disclosed herein. For example, specific primers that can be used in the methods disclosed herein include, but are not limited to the primers suitable for use in the standard exon array from the Affymetrix website listed at: http://www.affymetrix.com. In some aspects, the gene expression panel or array disclosed herein for can be used to determine or assess EoE or active EoE in a subject, wherein CCL26, KITLG, or POSTN RNA expression levels are detected in the sample.

In some aspects, a diagnostics kit is disclosed comprising one or more probes or primers capable of detecting, amplifying or measuring the presence or expression of one or more genes disclosed herein.

Disclosed herein, are solid supports comprising one or more primers, probes, polypeptides, or antibodies capable of hybridizing or binding to one or more of the genes disclosed herein. Solid supports are solid state substrates or supports that molecules, such as analytes and analyte binding molecules, can be associated. Analytes (e.g., calcifying nanoparticles and proteins) can be associated with solid supports directly or indirectly. For example, analytes can be directly immobilized on solid supports. Analyte capture agents (e.g., capture compounds) can also be immobilized on solid supports.

As mentioned herein, one of ordinary skill in the art can determine the expression level of one or more genes (or proteins) disclosed herein any number of ways. To detect or quantify the level of RNA products of the biomarkers within a sample, arrays, such as microarrays, RT-PCR (including quantitative RT-PCR), nuclease protection assays and Northern blot analyses can be used. Accordingly, in some aspects, the biomarker expression levels can be determined using arrays, microarrays, RT-PCR, quantitative RT-PCR, nuclease protection assays or Northern blot analyses.

In addition, the genes described herein can also be used as markers (i.e., biomarkers) for susceptibility to or presence or progression of EoE or active EoE. The methods and assays described herein can be performed over time, and the change in the level of the markers assessed. For example, the assays can be performed every 24-72 hours for a period of 6 months to 1 year, and thereafter carried out as needed. Assays can also be completed prior to, during, or after a treatment protocol. Together, the genes disclosed herein can be used to profile an individual's status of EoE. As used within this context, the terms "differentially expressed" or "differential expression" refers to difference in the level of expression of the biomarkers disclosed herein that can be assayed by measuring the level of expression of the products (e.g., RNA or gene product) of the biomarkers, such as the difference in level of messenger RNA transcript or a portion thereof expressed or of proteins expressed of the biomarkers. In some aspects, this difference is significantly different.

To improve sensitivity, more than one gene disclosed herein can be assayed within a given sample. Binding agents specific for different proteins, antibodies, nucleic acids provided herein can be combined within a single assay. Further, multiple primers or probes can be used concurrently. To assist with such assays, specific biomarkers can assist in the specificity of such tests.

Levels of expression can be measured at the transcriptional and/or translational levels. At the translational level, expression of any of the genes described herein can be measured using immunoassays including immunohistochemical staining, western blotting, ELISA and the like with an antibody that selectively binds to the corresponding gene or a fragment thereof. Detection of the protein using protein-specific antibodies in immunoassays is known in the art. At the transcriptional level, mRNA can be detected by, for example, amplification (e.g., PCR, LCR), or hybridization assays (e.g., northern hybridization, RNAse protection, or dot blotting). The level of protein or mRNA can be detected, for example, by using directly or indirectly labeled detection agents (e.g., fluorescently or radioactively labeled nucleic acids, radioactively or enzymatically labeled antibodies). Changes (e.g., increase or decrease) in the transcriptional levels can also be measured using promoter-reporter gene fusion constructs. For example, the promoter region of a gene encoding any of the genes disclosed herein can be fused (i.e., operably linked) to the coding sequence of a polypeptide that produces a detectable signal. Reporter constructs are well known in the art. Examples of reporter sequences include fluorescent proteins (e.g., green, red, yellow), phosphorescent proteins (e.g., luciferase), antibiotic resistance proteins (e.g., beta lactamase), enzymes (e.g., alkaline phosphatase).

EXAMPLES

Example 1: Food Specific Antibodies in Esophageal Secretions: Association with Trigger Foods in Eosinophilic Esophagitis (EoE)

Aims: To test whether antibodies against foods that trigger eosinophilic oesophagitis are secreted into the esophageal lumen where they can be collected by esophageal brushings.

Methods: Food specific immune responses were evaluated within brushings in 68 patients undergoing endoscopy (12 controls, 13 resolved eosinophilic oesophagitis, and 43 active eosinophilic oesophagitis). Seventeen participants identified their trigger foods via food elimination diets. Immunoglobulin A and Immunoglobulin G4 antibodies against the four most common eosinophilic oesophagitis food triggers were measured using the ImmunoCAP assay in the esophageal brushings. Food-specific antibody values were compared between active eosinophilic oesophagitis, resolved eosinophilic oesophagitis, and controls.

Results: Patients with active eosinophilic oesophagitis (>15 eosinophils/hpf) demonstrated increased Immunoglobulin A and Immunoglobulin G4 levels to common eosinophilic oesophagitis triggers compared to controls ($327\pm380$ v $150\pm130$ for Immunoglobulin A, and $1534\pm3346$ v $178\pm123$ for Immunoglobulin G4, $p<0.003$). Specific trigger foods were associated with elevated Immunoglobulin A and Immunoglobulin G4 responses compared to foods that did not trigger esophageal eosinophilia ($733\pm469$ v $142\pm64$, $p<0.001$ Immunoglobulin A and $2620\pm3228$ versus $526\pm1050$, $p<0.001$ Immunoglobulin G4).

Conclusions: Food specific antibodies are collected along the esophageal lumen of eosinophilic oesophagitis patients.

Introduction: Eosinophilic esophagitis (EoE) is increasingly recognized as a common cause of poor quality of life, dysphagia and food impactions in every age group (Holbreich M. Allergy Asthma Proc 2019; 40:198-203; Peiris C D, Tarbox J A. JAMA 2019; 321:1418; Reed C C, Dellon E S. Med Clin North Am 2019; 103:29-42; and Lucendo A J, et al. Aliment Pharmacol Ther 2017; 46:401-409). Immunologic reactions to foods are implicated, but allergy testing (skin prick testing, Immunoglobulin E antibody testing, or atopy patch testing) does not identify foods responsible for disease (Aceves S S. Allergy Testing in Patients with Eosinophilic Esophagitis. Gastroenterol Hepatol (N Y) 2016; 12:516-518; Anyane-Yeboa A, Wang W, Kavitt R T. The Role of Allergy Testing in Eosinophilic Esophagitis. Gastroenterol Hepatol (N Y) 2018; 14:463-469; and Philpott H, et al. Aliment Pharmacol Ther 2016; 44:223-33). Nonetheless, food antigens have been implicated in the etiology and exacerbations of EoE in both pediatric and adult populations as evidenced by resolution of disease after elimination diets (Philpott H, et al. Aliment Pharmacol Ther 2016; 44:223-33; Chehade M, Sher E. Allergy Asthma Proc 2017; 38:170-176; Fahey L M, et al. Clin Transl Gastroenterol 2018; 9:139; de Bortoli N, Penagini R, Savarino E, et al. Dig Liver Dis 2017; 49:254-260; and Philpott H, Thien F. The Role of Allergy Testing in Eosinophilic Esophagitis: an Update of the Evidence. Curr Treat Options Gastroenterol 2017; 15:26-34). Immunoglobulin E is elevated in the mucosa of EoE patients, but clinical trials evaluating the accuracy of Immunoglobulin E based skin prick testing to identify causative foods have failed to demonstrate satisfactory results (Philpott H, Thien F. Curr Treat Options Gastroenterol 2017; 15:26-34; Kamdar T A, et al. Clin Mol Allergy 2010; 8:16; Gottlieb S J, et al. J Allergy Clin Immunol 2013; 131:242-3; Aceves S S. Clin Gastroenterol Hepatol 2014; 12:1216-23; Paquet B, Begin P, Paradis L, et al. J Allergy Clin Immunol 2013; 131:613; Erwin E A, et al. J Allergy Clin Immunol Pract 2015; 3:896-904 e3; and Turnbull J L, et al. Aliment Pharmacol Ther 2015; 41:3-25). Similarly, a clinical trial of omalizumab failed to reduce eosinophil infiltration in the oesophagus of EoE patients (Clayton F, et al. Gastroenterology 2014; 147:602-9). Hypothesizing that cell-mediated reactions to foods leads to esophageal eosinophilia, others have evaluated sensitivity and specificity of atopy patch testing but with poor results (Aceves S S. Allergy Testing in Patients with Eosinophilic Esophagitis. Gastroenterol Hepatol (N Y) 2016; 12:516-518; Anyane-Yeboa A, et al. The Role of Allergy Testing in Eosinophilic Esophagitis. Gastroenterol Hepatol (N Y) 2018; 14:463-469; Bahna S L. Allergy Asthma Proc 2008; 29:447-52; and Blanchard C, et al. J Intern Med 2017; 281:448-457). Because, in EoE, the inflammation is localized to the oesophagus, one can characterize the disease as the consequence of localized, esophageal specific immune reactions. For example, Clayton, et al identified increased levels of total Immunoglobulin G4 in tissue homogenates from EoE, suggesting that local immune responses occur (Clayton F, et al. Gastroenterology 2014; 147:602-9). Forceps and brush biopsies have revealed that immunoglobulins (Immunoglobulin G4 and Immunoglobulin E) are increased in EoE tissues (Ramaswamy A T, et al. Int Forum Allergy Rhinol 2019; 9:870-875). Although not studied specifically in EoE, Immunoglobulin A is a known mucosal exclusion antibody secreted on the gastrointestinal surface to protect the body from potential threats, such as bacteria and viruses (Carlier F M, et al. Clin Exp Allergy 2016; 46:1372-1388). Local reactions within diseased tissues may also involve either secretory or immune mediated Immunoglobulin A production as seen in celiac disease (Koninckx C R, et al. J Pediatr Gastroenterol Nutr 1984; 3:676-82; and Lamm M E, et al. APMIS 1995; 103:241-6). Immunoglobulin A level and responses are increasingly studied in food allergy (Ahrens N, et al. Clin Exp Immunol 2008; 151:455-8; and Andre C. Letter: Allergy, tolerance, and immunoglobulin A. Lancet 1974; 2:782). It is plausible that Immunoglobulin A may be secreted in response to foods that are mediating antigenic responses in the oesophagus. It was tested whether Immunoglobulin G4 and Immunoglobulin A are produced in the oesophagus of EoE and discover foods responsible for eosinophilic esophageal inflammation.

Methods: Study design. The study was designed to test if foods triggering EoE also stimulated Immunoglobulin A and Immunoglobulin G4 antibody production. Patients consented to one-time sampling of their oesophagus as they presented for upper endoscopy for dysphagia or monitoring of their known EoE. Patients were offered enrollment if they met either of two criteria: 1) no prior diagnosis of EoE but dysphagia requiring endoscopic evaluation, or 2) previously diagnosed EoE presenting for a follow-up endoscopic biopsy to assess disease status. Patients consented to allow investigators to follow their clinical course and biopsy results during their follow up routine clinical care. Patients diagnosed with co-existing immunologic disorders, including autoimmune oesophagitis (i.e., lichen planus), Crohn's disease, systemic scleroderma, or those requiring systemic immunosuppression, were excluded from further analysis. In 68 patients, both Immunoglobulin A and Immunoglobulin G4 food specific antibodies were measured in esophageal brushings and were included in the final analysis. Three cohorts analyzed were: active EoE, resolved EoE, and controls. Patients were diagnosed with EoE by standard criteria (Dellon E S, et al. Updated International Consensus Diagnostic Criteria for Eosinophilic Esophagitis: Proceedings of the AGREE Conference. Gastroenterology 2018; 155:1022-1033 e10), 15 eosinophils per high powered field (HPF) on at least one esophageal biopsy and accompanying esophageal symptoms. Patients with a history of EoE whose current biopsies had less than 15 eosinophils/HPF (and in whom symptoms were resolved) were considered resolved EoE patients. Patients who presented with dysphagia without any prior esophageal diagnosis who had normal histopathology on esophageal biopsies were considered controls.

Collection of Esophageal Secretions. The esophageal brushing was obtained prior to esophageal biopsies during upper endoscopy. A Cook medical cytobrush (Cook Medical, Indianapolis, IN) was passed through the endoscope and applied to the lumen of the oesophagus and withdrawn from the distal 5 cm of the oesophagus to the upper oesophagus (approximately 15-20 cm from teeth). The brush was then removed, and flash frozen at −70° C. until further evaluation.

Clinical course for patients on Elimination Diets. EoE patients who chose food elimination diets as part of clinical care were monitored to record their food triggers. Food triggers were recorded as those whose removal either reduced eosinophilia to less than 15 eosinophils/HPF (for those undergoing single food elimination) or those whose reintroduction resulted in esophageal eosinophilia >15 eosinophils/HPF after resolution (multiple food elimination). Standard of care includes 4 weeks of specific food reintroduction prior to repeat endoscopy to identify trigger foods (Gonsalves N. Gastrointest Endosc Clin N Am 2018; 28:89-96; and Gonsalves N, et al. Gastroenterology 2012; 142:1451-9 e1). Symptoms alone were not adequate to categorize a patient as reactive to a particular food. For those who eliminated multiple foods, once resolved, foods that did not increase eosinophil counts to greater than 15 eosinophils/HPF after re-introduction were identified as true negatives. Patients who completed the reintroductions were included in the final analyses.

Food-specific antibody testing. Brushes were thawed and equilibrated with 1 ml of Phadia diluent solution (Product No. 10-9498-01, Kalamazoo, MI) by immersion for ~30 minutes with occasional shaking. In separate experiments, the quantity of secretion per brush was measured by centrifugation for 1 minute at 10,000 RPM yielding approximately 21-23 microliters of fluid per brush. The extracted esophageal fluids in the Phadia diluent at an approximately 1:50 dilution were analyzed for Immunoglobulin G4 and Immunoglobulin A antibodies to four food allergens: wheat f1, soybean f14, casein f78, and egg f245 employing Phadia ImmunoCap reagents. Casein and gluten were chosen to study as they are specific food proteins thought to be the primarily reactive ones for dairy and wheat, respectively. Briefly, 40 µL of diluted secretions was added to the food specific solid phase antigens, referred to as CAPs, followed by washing and addition of Immunoglobulin A/Immunoglobulin G4 antibody conjugates, repeat washing and, lastly, by addition of development solution per protocol. Stop solution was added, and the resulting fluorescence signal was measured (response value). Due to the limitations of measuring concentrations from the 1:50 dilution, response values were measured and reported. Results are listed as response values. For assay validation, low and high range control samples were included in each analysis. The participants underwent both Immunoglobulin G4 and Immunoglobulin A analyses for food specific antibodies for gluten, casein, soy, egg, and the response values detected using the Immunocap system are reported.

Statistical analyses. Comparisons between groups for response values was performed via ANOVA and Mann Whitney U testing depending upon the groups assessed. For assessment of food triggers, foods that trigger EoE (true positives) and foods that did not trigger EoE (true negatives) were determined for patients who underwent food elimination trials. Immunoglobulin G4 and Immunoglobulin A response values were standardized (rescaled to have a mean of zero and a standard deviation of one) within individuals to account for different volumes collected between individuals and maintain valid comparison thereafter. To identify food triggers for each individual, heat maps were used on the standardized Immunoglobulin G4 and Immunoglobulin A response values for gluten, soy, casein, and egg, and results were confirmed by post-hoc probabilistic logistic regression models. Fisher's exact test and the Mann-Whitney U test were used to assess the statistical significance of differences in categorical and quantitative variables between groups, respectively.

Results: Patient Characteristics. Sixty eight patients were enrolled at the time of endoscopy and successfully underwent esophageal brushings prior to esophageal biopsies. Demographics are given in Table 1. The 12 control participants had dysphagia but no concurrent systemic autoimmune or allergic disease and normal histopathology on biopsy. The 13 resolved EoE patients had fewer than 15 eosinophils/HPF whereas prior biopsies had demonstrated >15 eosinophils/HPF); resolved patients had been treated with topical steroids (n=3), proton pump inhibitor (n=3), or food elimination diets (n=7). The remainder of enrolled patients met criteria for active EoE.

TABLE 1

Demographics of total cohort. Forty-three patients with active eosinophilic esophagitis (EoE: >15 eos/HPF and esophageal symptoms) were enrolled, and 17 completed food elimination and reintroduction diets. Thirteen patients had been treated and had eos <15/HPF with resolution of symptoms and are resolved eosinophilic Oesophagitis (resolved EoE) patients. Twelve patients had dysphagia but normal esophageal biopsies and are controls.

|  | Active EoE (n = 43) | Resolved EoE (n = 13) | Controls (n = 12) |
|---|---|---|---|
| Age years (std) | 37.0 (11.9) | 32.2 (10.7) | 46.8 (18.2) |
| % Male | 51.1% | 30.8% | 25% |
| Eosinophils/ HPF (std) | 62.7 (31.1) | 4.5 (4.3) | 0 |

Figure 2:
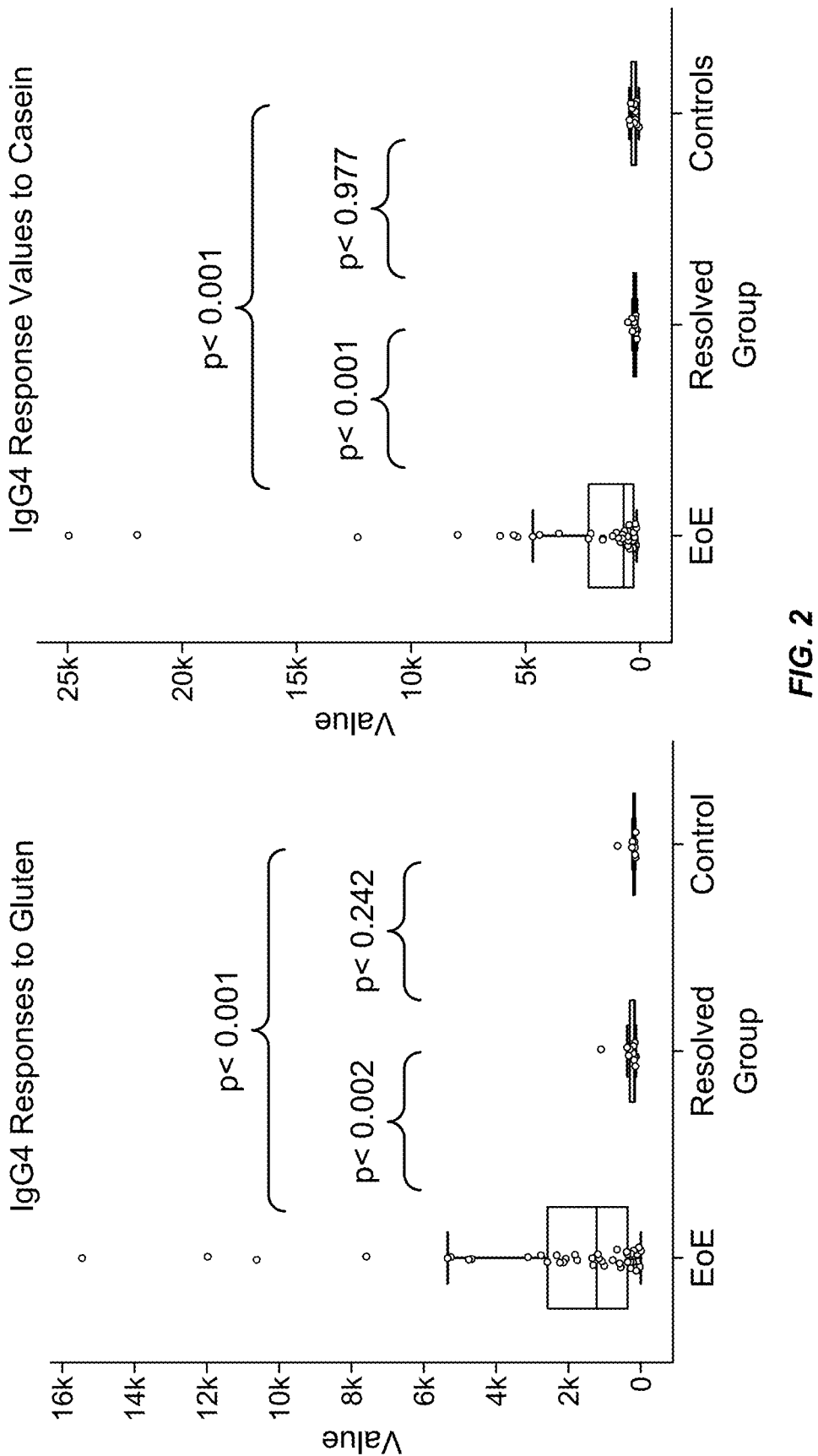
FIG. 2 shows the Immunoglobulin G4 response values to gluten, casein, soy, and egg cohorts (active EoE, resolved EoE, and controls). Active EoE showed significantly higher Immunoglobulin G4 antibody levels to the four food antigens compared to resolved EoE and controls. IgG4=Immunoglobulin G4.
Figure 2:
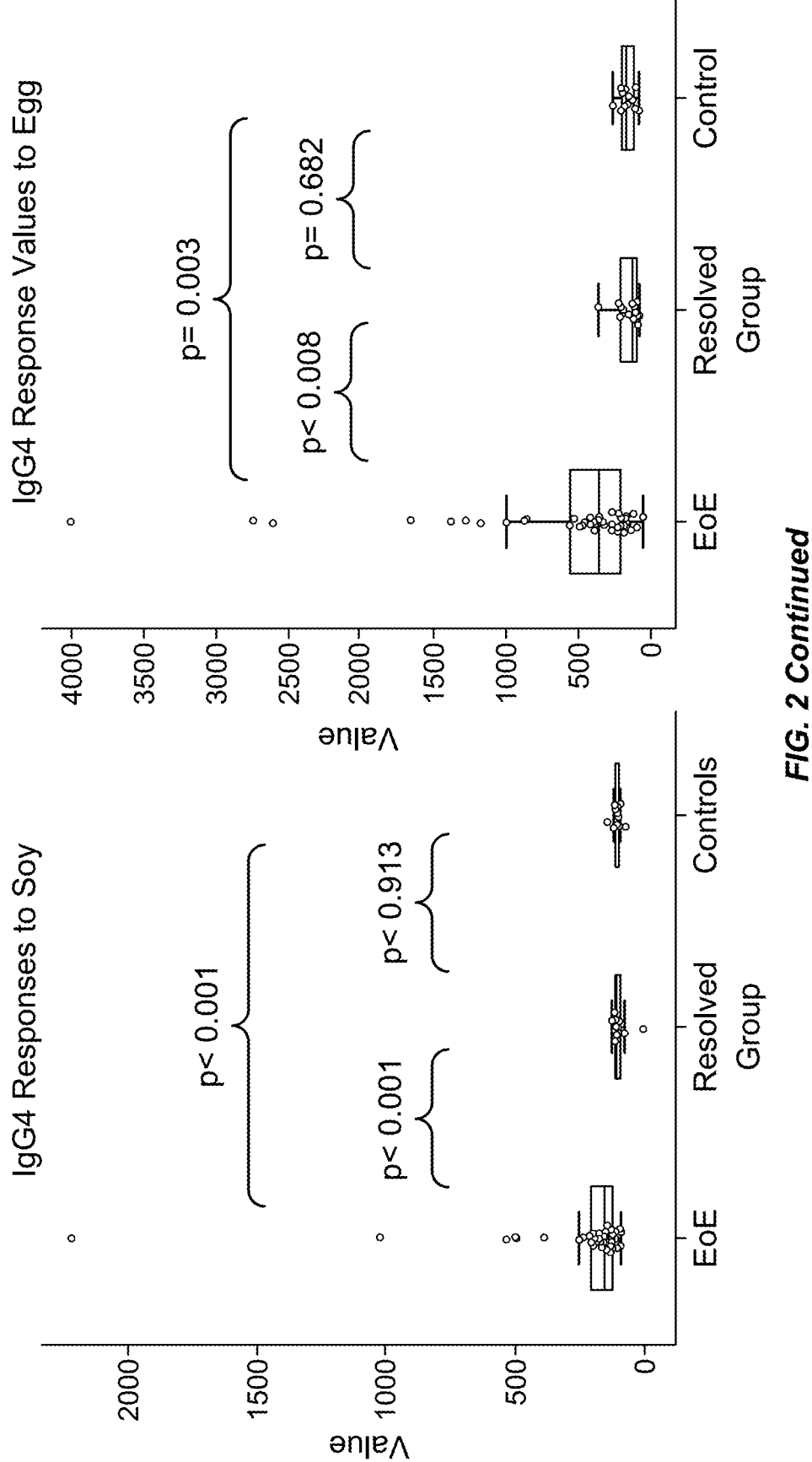
Figure 3:
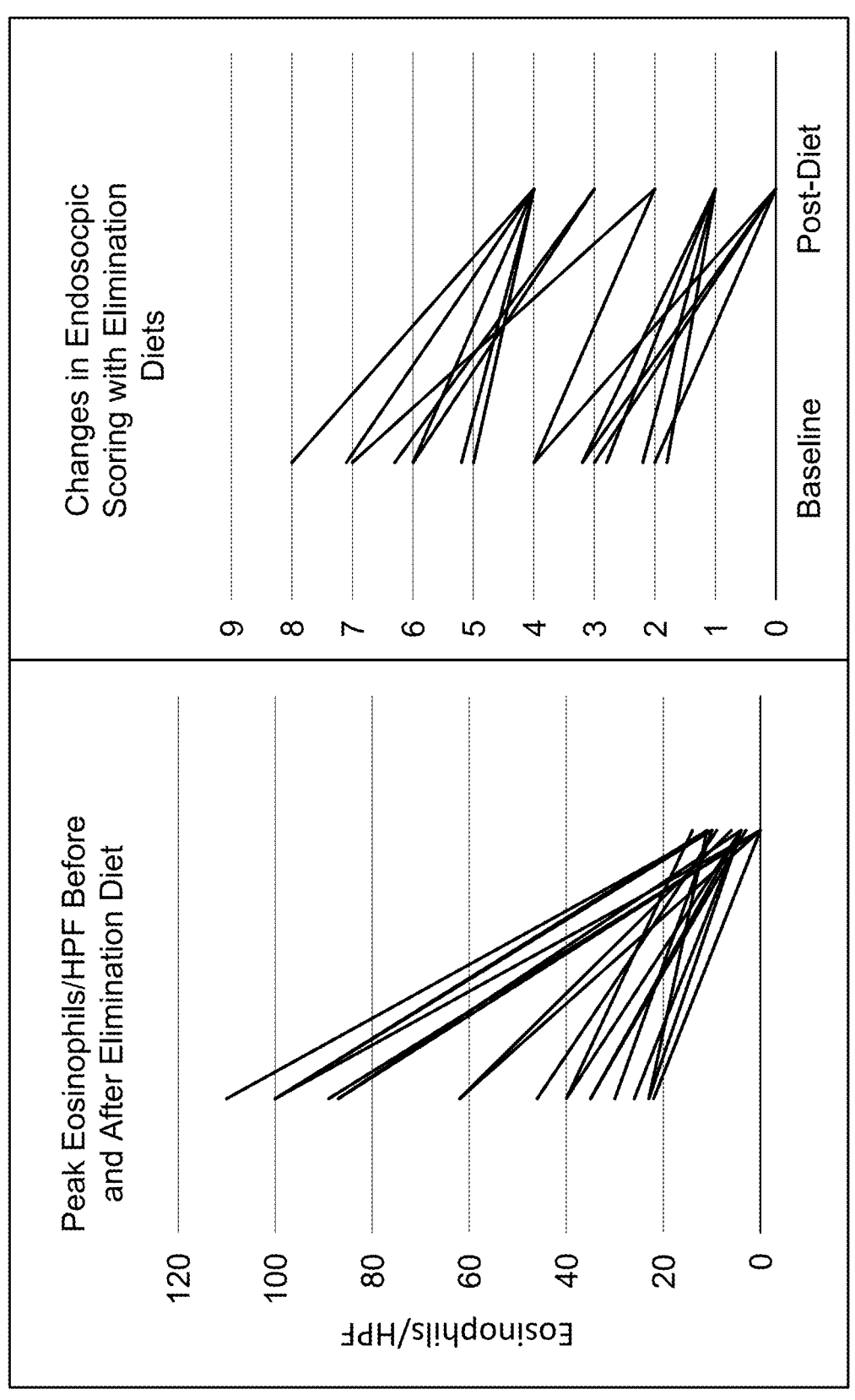
FIG. 3 shows the esophageal eosinophil infiltration and endoscopic scoring before and after institution of elimination diets in the 17 patients.

Active EoE Patients Demonstrate Food Specific Immunoglobulin A and Immunoglobulin G4. Analyses of esophageal secretions revealed the presence of Immunoglobulin A and Immunoglobulin G4 responses as shown in FIGS. 1 and 2, respectively. Overall, EoE patients had increased levels of Immunoglobulin A and Immunoglobulin G4 responses averaged over the tests when compared to controls (327±380 v 150±130 for Immunoglobulin A, and 1534±3346 versus 178±123 for Immunoglobulin G4, p<0.003 for both). Upon comparison between each individual group, active EoE patients, on average, had greater values of Immunoglobulin A responses to casein (p<0.001), gluten (p<0.001), soy (p<0.001) and egg (p<0.008) compared to resolved EoE patients. Active EoE participants had greater Immunoglobulin A response values to gluten (p<0.001), casein (p<0.001) compared to controls, but did not have significantly different response values from controls for soy (p=0.223) and egg (p=0.379). Active EoE participants demonstrated higher levels of Immunoglobulin G4 responses to all of the foods when compared to resolved EoE and controls Table 2).

counts averaged 6.2 eosinophils/HPF (std4.1) (p<0.001) (FIG. 3). Additionally, food elimination diets resulted in endoscopic improvement with endoscopic reference scores evaluating oedema, rings, exudates, furrows and strictures as high as 4.5 (std 1.9) prior to diet changing to 2 (std 1.6) after diet (p<0.001). Strictures were less likely to resolve with diet. The food triggers were either wheat (n=9), dairy (n=4), or both (n=4). One patient had removed pork and beef prior to testing due to "reactions." Another patient reacted to reintroduction of chicken and rice with esophageal eosinophilia >15 eosinophils/HPF. Finally, an additional patient

TABLE 2

Mean response values with standard deviations for the food antigens in each group.
IgA demonstrates less variability within EOE patients compared to IgG4.

| IgA Response Values | | | | IgG4 Response Values | | |
|---|---|---|---|---|---|---|
| Active Eoe | Resolved EoE | Control | | Active EoE | Resolved EoE | Control |
| 522 ± 450 | 150 ± 138 | 233 ± 197 | Gluten | 2419 ± 3392 | 290 ± 258 | 220 ± 137 |
| 484 ± 478 | 155 ± 94 | 160 ± 127 | Casein | 2824 ± 5322 | 245 ± 115 | 264 ± 131 |
| 166 ± 151 | 67 ± 33 | 110 ± 64 | Soy | 255 ± 353 | 97 ± 30 | 105 ± 17 |
| 136 ± 92 | 75 ± 30 | 109± | Egg | 638 ± 806 | 159 ± 79 | 163 ± 52 |

Elimination Diets Identify Trigger Foods in 17 Patients. A total of 27 patients attempted a food elimination diet. Seven patients failed elimination diets of choice and did not pursue additional food elimination (3 failed 6 food—or greater—elimination diet, 2 failed two food elimination, and 2 failed one food elimination). Three patients responded to a six-food elimination diet but failed to reintroduce all foods.

A total of 17 patients completed their chosen dietary trials in totality. Five patients underwent removal of a single food with resolution of esophageal eosinophilia implicating the single eliminated food as the trigger food. The remaining 12 patients elected to remove multiple foods from their diet. Trigger foods were identified when symptoms and esophageal eosinophilia returned after reintroduction of that one specific food group after initial resolution of disease. Eosinophil counts averaged 60.5 eosinophils/HPF (std 32.1) before food eliminations whereas afterward, eosinophil felt poorly on eggs reintroduction but did not develop esophageal eosinophilia (8 eosinophils/HPF).

Figure 4A:
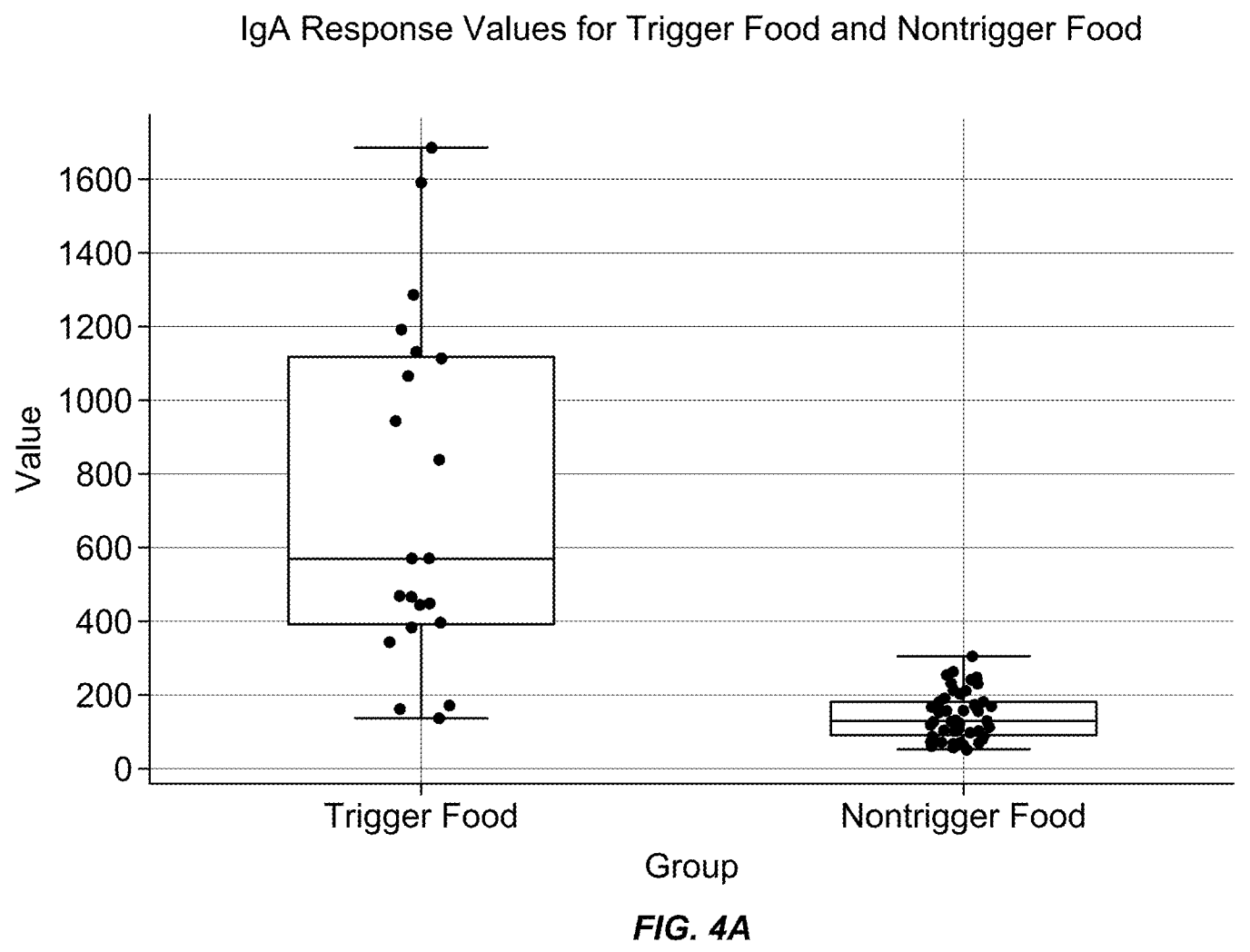
Figure 4B:
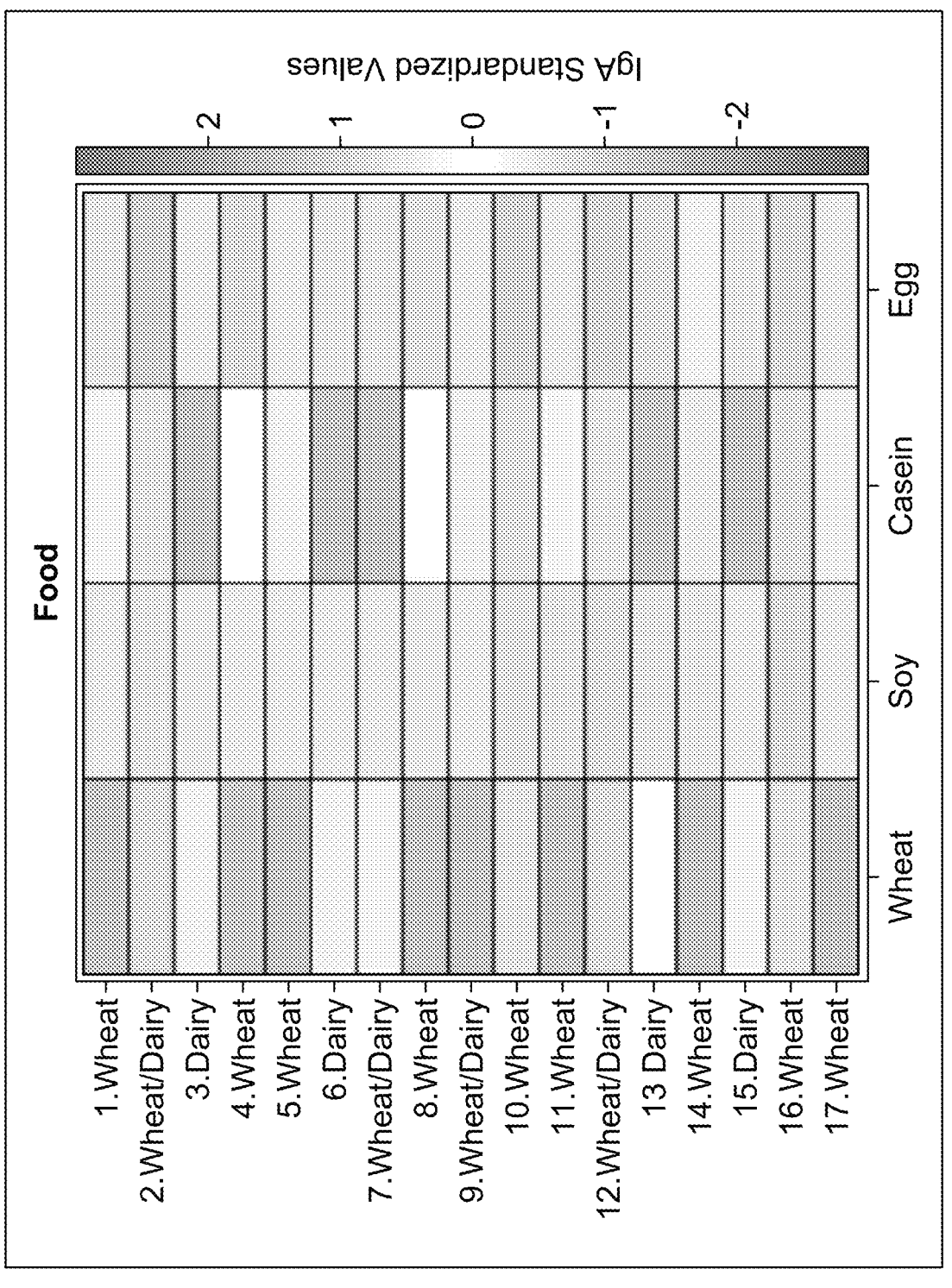
Figure 4C:
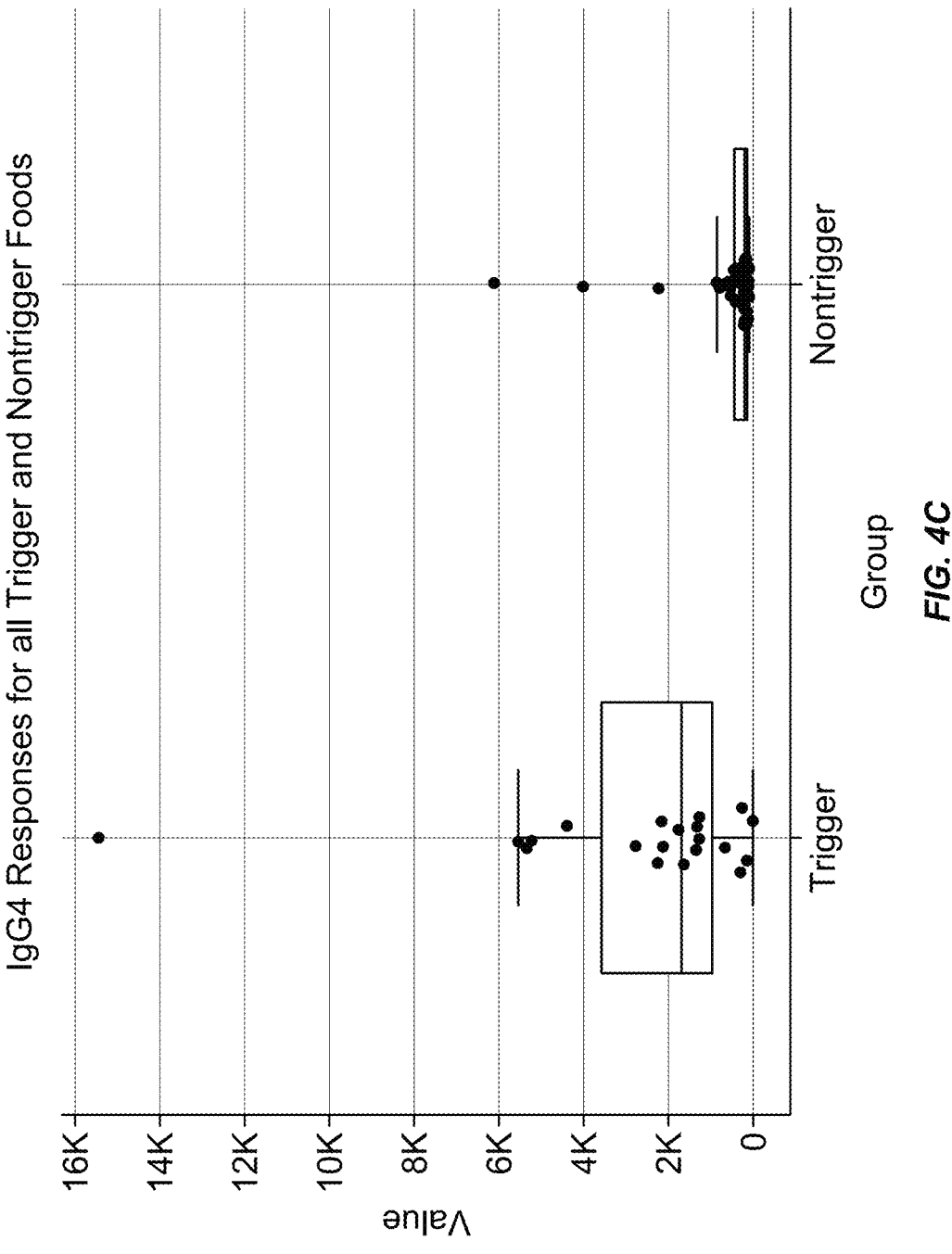
Figure 4D:
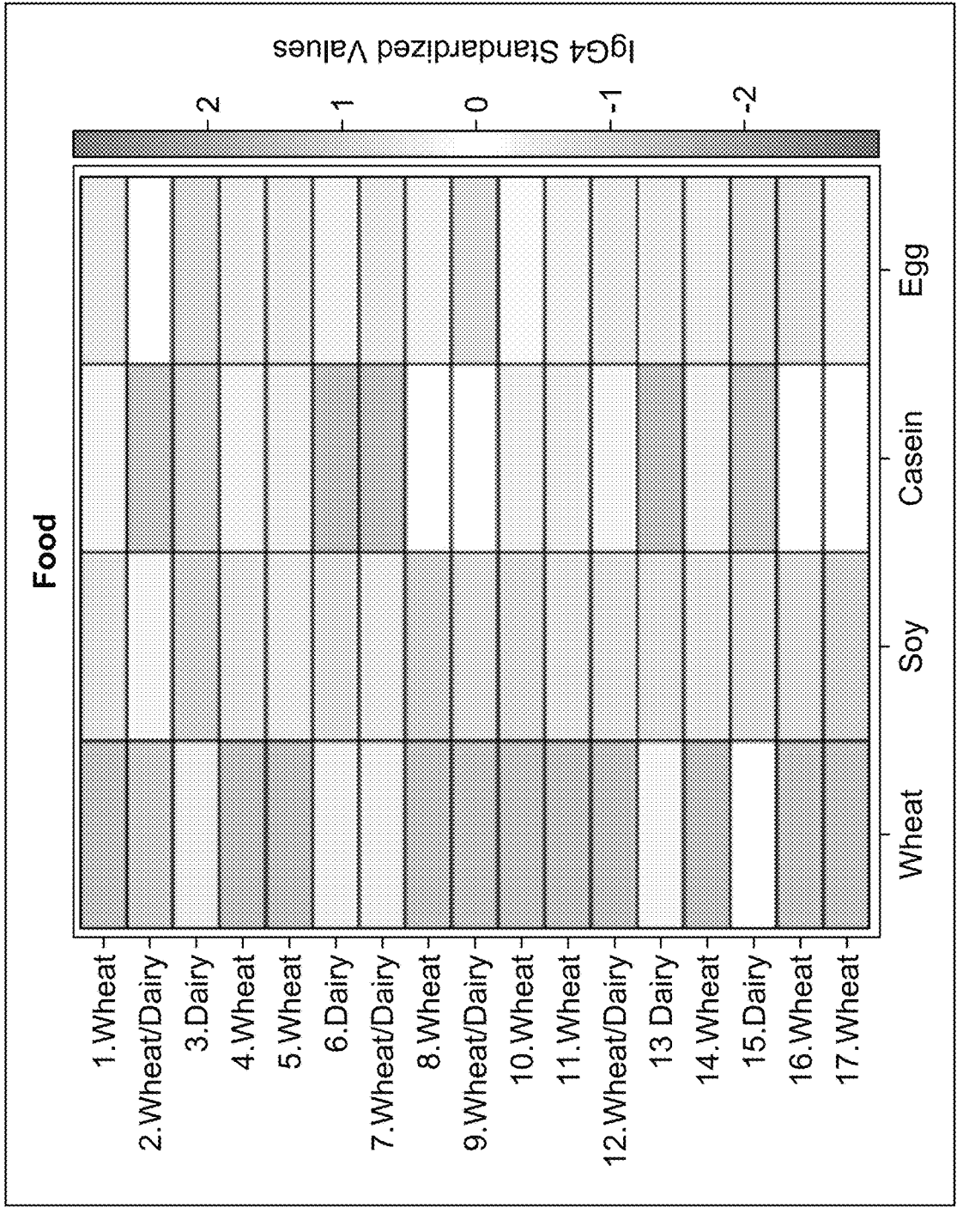
Figure 5:
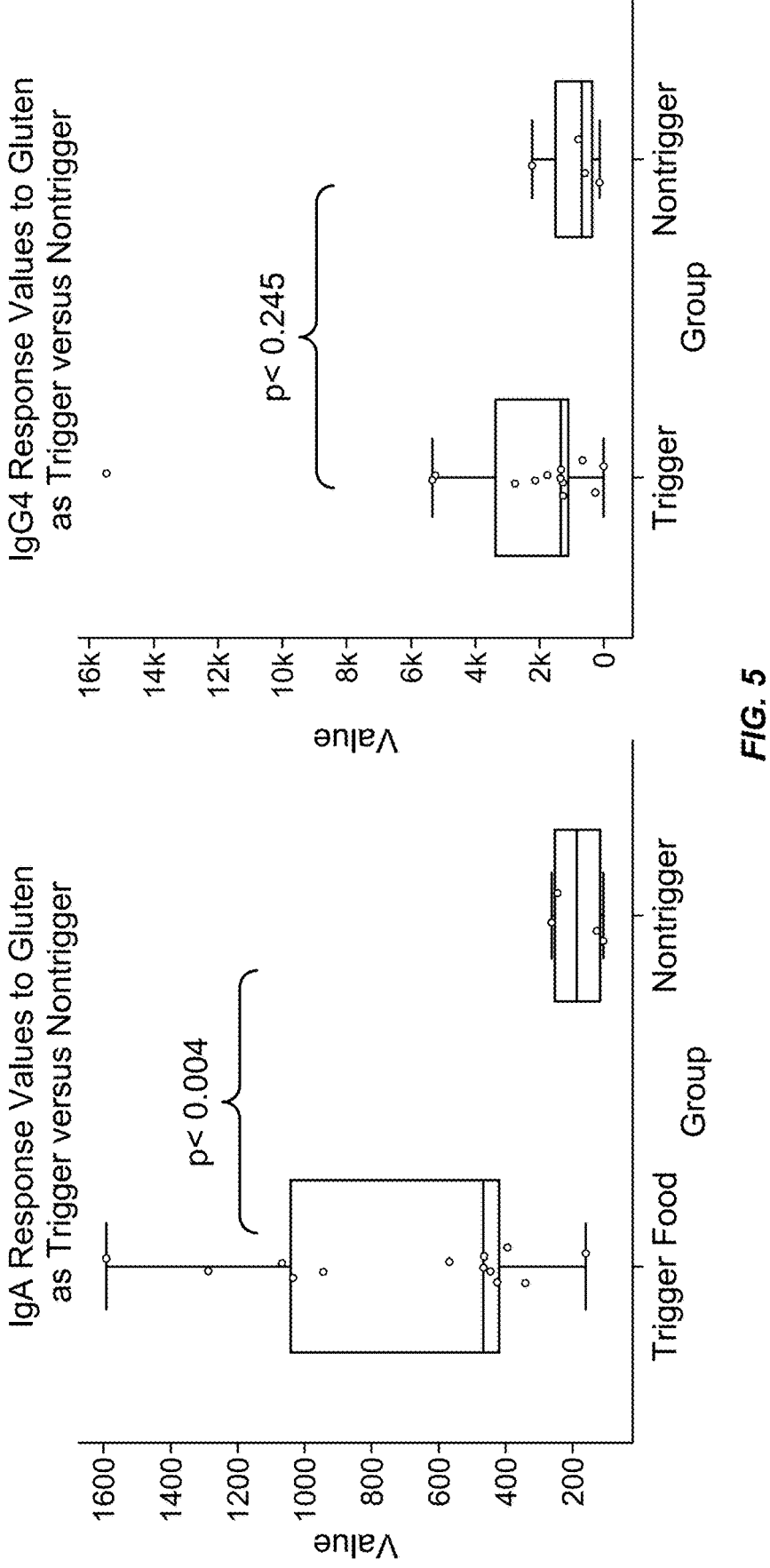
FIG. 5 shows Immunoglobulin A and Immunoglobulin G4 antibody levels to gluten and casein as trigger and non-trigger foods. Casein Immunoglobulin A responses are significantly elevated in those who had dairy as a trigger as opposed to those without dairy. There was no significant difference in Immunoglobulin G4 response values between those found to have diary as a trigger and those who did not. However, this was likely due to one large outlier in the non-trigger group. Wheat response values for Immunoglobulin A were elevated significantly in those who had wheat trigger for their EoE. Immunoglobulin G4 response values again did not reliably differentiate whether wheat was a trigger food or not in this limited cohort. IgA=Immunoglobulin A. IgG4=Immunoglobulin G4.
Figure 5:
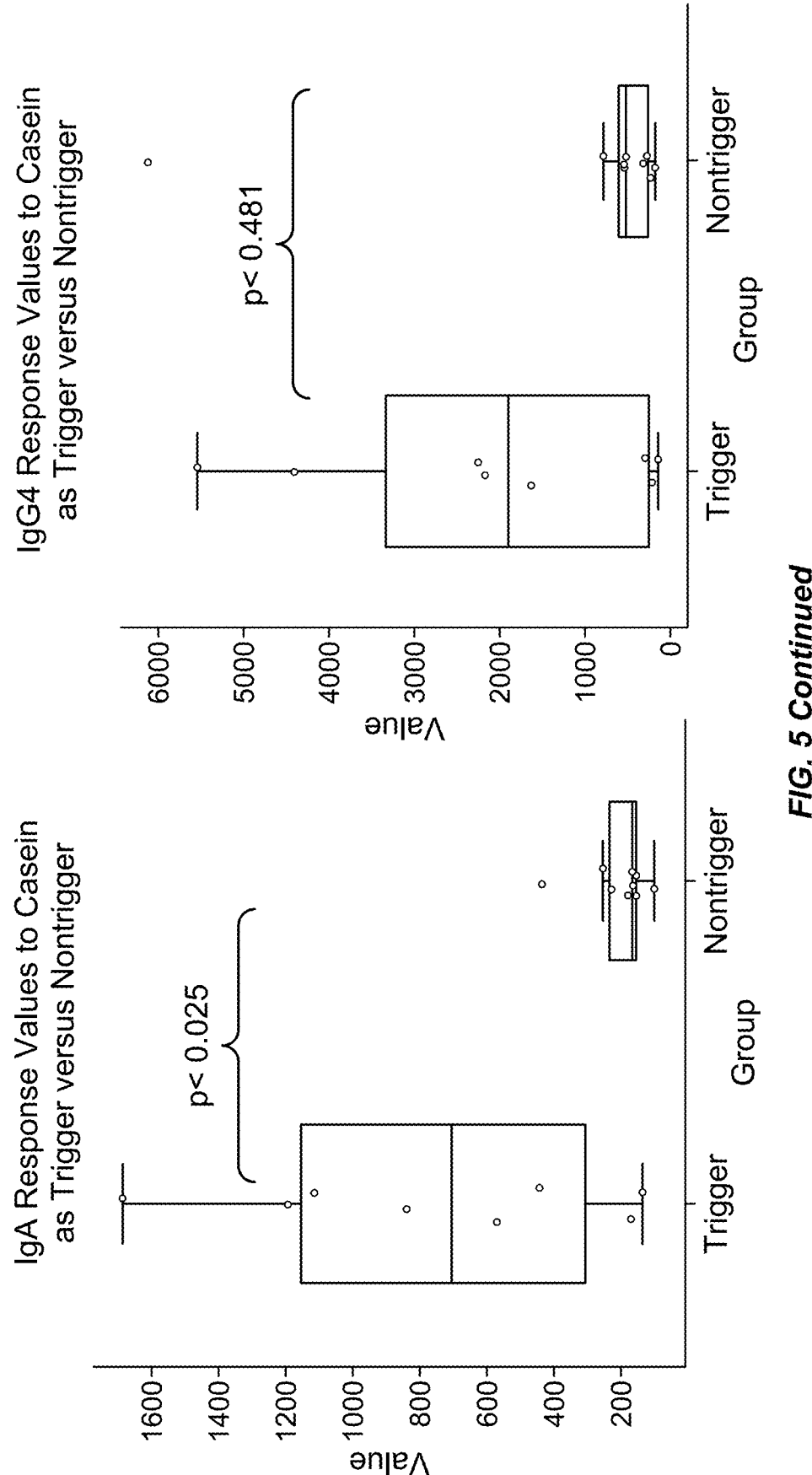

Immunoglobulin A and Immunoglobulin G4 Food Specific Antibody Reactivity is Increased to Trigger Foods. The levels of Immunoglobulin A and Immunoglobulin G4 antibodies for the 17 patients undergoing successful food elimination testing are shown in Table 3 and FIGS. 4 and 5. The foods that were found to be the triggers for the EoE (trigger foods) demonstrated greater Immunoglobulin A antibody values than non-trigger foods (733±469 versus 142±64, p<0.001). Participants with wheat as a trigger food demonstrated higher Immunoglobulin A antibody values to gluten than those patients who did not have wheat as a trigger food (707±430 versus 185±80, p<0.004). Participants with dairy as the trigger showed greater Immunoglobulin A antibody values to casein than those without dairy triggers (859±515 versus 197±94, p<0.021).

TABLE 3

Immunoglobulin A and Immunoglobulin G4 antibody levels to gluten, soy, casein, and egg in 17
patients who completed food elimination and reintroduction diets. Most trigger foods showed
high levels for Immunoglobulin A and Immunoglobulin G4. Variability in Immunoglobulin G4 within
and between patients resulted in difficult interpretation for overall cohort. Immunoglobulin
A and Immunoglobulin G4 antibody levels to trigger foods are bolded in the table.

| Age | Gender | Trigger Foods (s)* | ImmunoglobulinA Response Values | | | | Immunoglobulin G4 Response Values | | | |
|---|---|---|---|---|---|---|---|---|---|---|
| | | | Gluten | Soy | Casein | Egg | Gluten | Soy | Casein | Egg |
| 41 | M | Wheat | 1066 | 129 | 253 | 121 | 2766 | 147 | 526 | 221 |
| 55 | M | Wheat/Dairy | 465 | 231 | 442 | 172 | 0 | 95 | 302 | 121 |
| 30 | F | Dairy | 128 | 87 | 569 | 102 | 134 | 91 | 149 | 95 |
| 39 | M | Wheat | 341 | 122 | 179 | 89 | 5250 | 146 | 786 | 458 |
| 39 | M | Wheat | 467 | 67 | 100 | 58 | 2130 | 129 | 184 | 160 |
| 19 | F | Dairy | 245 | 163 | 1192 | 132 | 782 | 206 | 4403 | 857 |
| 29 | F | Wheat/Dairy | 395 | 239 | 1686 | 179 | 262 | 176 | 1629 | 229 |
| 29 | M | Wheat | 569 | 125 | 228 | 102 | 1271 | 128 | 543 | 418 |
| 67 | M | Wheat/Dairy | 1287 | 80 | 136 | 69 | 5347 | 252 | 2168 | 229 |
| 33 | M | Wheat | 428 | 206 | 435 | 166 | 1273 | 144 | 322 | 418 |
| 63 | F | Wheat | 446 | 96 | 155 | 109 | 1763 | 152 | 279 | 324 |
| 34 | M | Wheat/Dairy | 943 | 189 | 838 | 151 | 662 | 132 | 217 | 171 |
| 27 | F | Dairy | 106 | 70 | 170 | 65 | 592 | 198 | 2251 | 357 |

TABLE 3-continued

Immunoglobulin A and Immunoglobulin G4 antibody levels to gluten, soy, casein, and egg in 17
patients who completed food elimination and reintroduction diets. Most trigger foods showed
high levels for Immunoglobulin A and Immunoglobulin G4. Variability in Immunoglobulin G4 within
and between patients resulted in difficult interpretation for overall cohort. Immunoglobulin
A and Immunoglobulin G4 antibody levels to trigger foods are bolded in the table.

| Age | Gender | Trigger Foods (s)* | ImmunoglobulinA Response Values | | | | Immunoglobulin G4 Response Values | | | |
|---|---|---|---|---|---|---|---|---|---|---|
| | | | Gluten | Soy | Casein | Egg | Gluten | Soy | Casein | Egg |
| 34 | F | Wheat | 1133 | 115 | 165 | 210 | 1329 | 147 | 237 | 211 |
| 32 | M | Dairy | 262 | 155 | 1114 | 123 | 2235 | 213 | 5542 | 168 |
| 40 | F | Wheat | 160 | 71 | 166 | 70 | 1345 | 113 | 548 | 173 |
| 36 | M | Wheat | 1591 | 50 | 154 | 55 | 15454 | 534 | 6123 | 4008 |

*Measurements are based upon immunofluorescence reactivity (i.e., response values).

Trigger foods also resulted in greater Immunoglobulin G4 response values than non-trigger foods (2620±3228 versus 526±1050, p<0.001). However, specifically comparing Immunoglobulin G4 antibody levels to gluten, participants with wheat triggers were not significantly different than those who did not have wheat as a trigger food (2988±4097 versus 936±908, p<0.25). Participants with dairy triggers did not have significantly different response to casein than those without dairy triggers (2349±2000 versus 976±1818, p<0.49) likely due to the high variability seen in the Immunoglobulin G4 responses.

Foods Implicated as Triggers by Elevated Immunoglobulin A and Immunoglobulin G4 Responses. A total of 21 food triggers were identified in the 17 patients (Table 2). Although significant variability occurred in the response values among patients, food triggers were almost always identified by higher antibody responses for Immunoglobulin A and Immunoglobulin G4. For Immunoglobulin A responses, in 19/21 instances the food trigger(s) showed the greatest response values (or the top two greatest response values in the case of two food triggers). For Immunoglobulin most accurately in the identification of foods responsible for causing EoE. Heat-maps post-hoc logistic regression analysis (FIGS. 4b and 4d) confirmed one misclassification out of 17 (i.e. 94.1% correct classification) was found for wheat as the trigger food, two for dairy (i.e. 88.2% correct classification) and two for wheat/dairy (i.e. 88.2% correct classification) according to the Immunoglobulin A results, indicating high classification power.

Figures 9A, 9B:
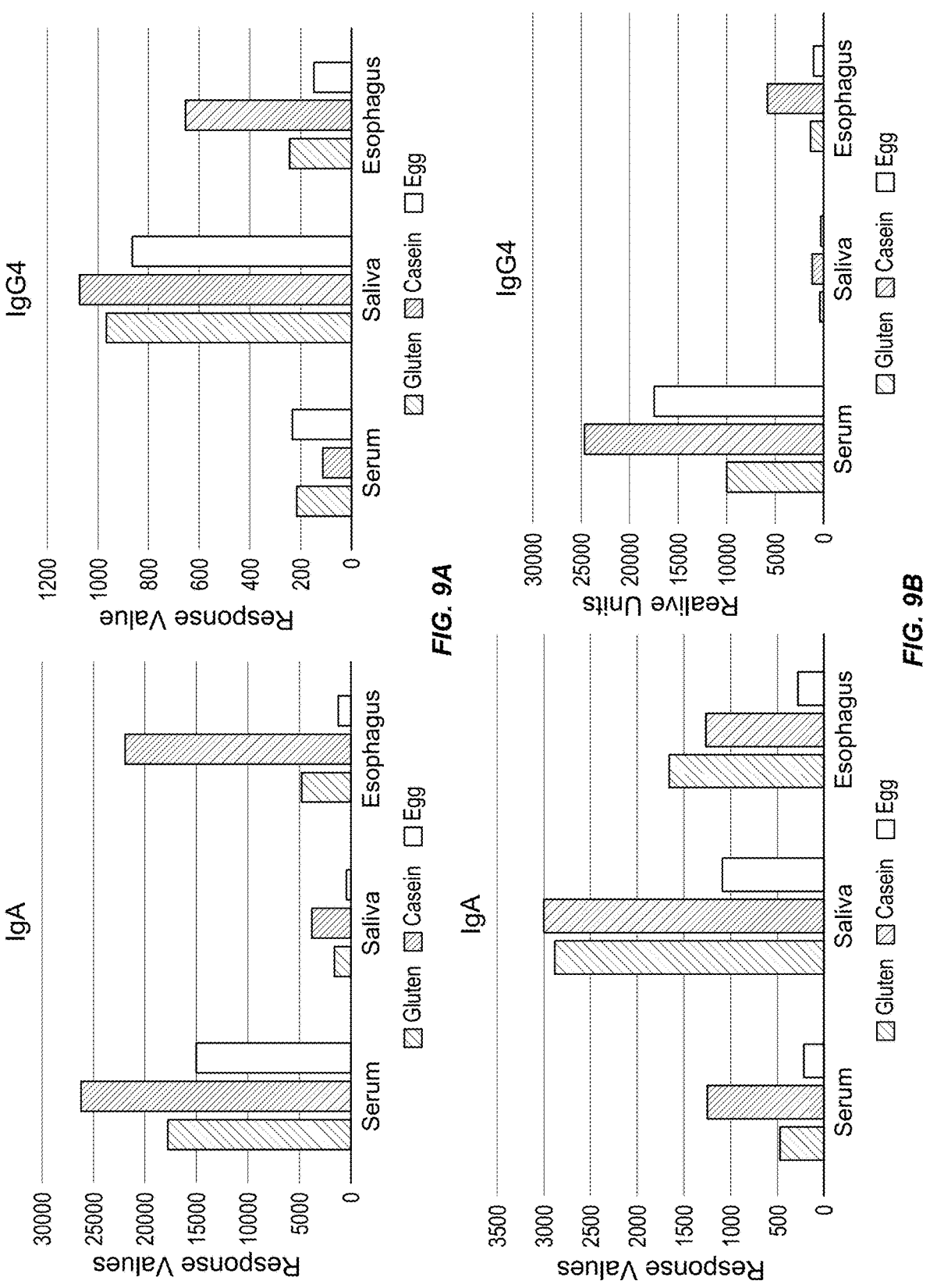
FIGS. 9A-C show food-specific antibodies in esophageal secretions, but not saliva nor serum, are diagnostic for EoE. Ratios of wheat:casein:egg responses differed in three patients who underwent simultaneous sampling of saliva (whole), serum, and esophageal secretions at the time of endoscopy.
Figure 9C:
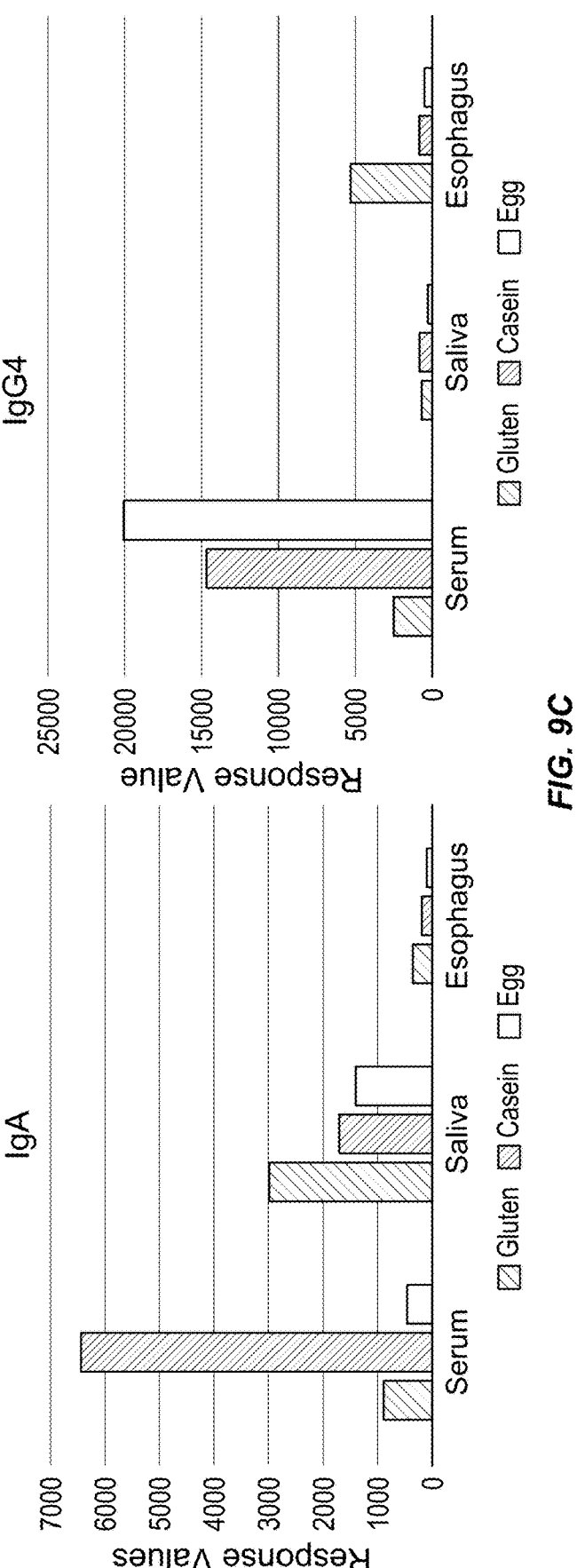

Saliva, serum, and esophageal secretions collected from three patients at the time of upper endoscopy and tested. Immunoglobulin response ratios differed among the three different sources indicating that the esophageal collections were not highly influenced by blood or saliva contamination (FIG. 9).

Patients in the active EoE group had a follow up recorded when they presented for a follow up endoscopy on diet and had both Immunoglobulin A and Immunoglobulin G4 testing performed on their brushings. In the 3 cases tested, the food specific antibodies appeared to reduce in parallel to the resolution of disease (Table 4).

TABLE 4

Three patients underwent esophageal sampling before and after food elimination
diets when eosinophilia was resolved (less than 15 eos/HPF). Food antibody
response values appeared to decrease with resolution of disease and/or removal
of foods. Patient one was sampled after undergoing wheat and dairy elimination.
Patient two underwent repeat sampling after dairy, peas, beans, fruit, vegetable
elimination (based upon skin IgE testing). Patient three underwent dairy
elimination prior to the second sample. Patient four was on topical steroids
for the esophagus at the time of the second sample.

| | Gluten IgA | Soy IgA | Casein IgA | Egg IgA | Gluten IgG4 | Soy IgG4 | Casein IgG4 | Egg IgG4 |
|---|---|---|---|---|---|---|---|---|
| Pre-Diet (1) | 395 | 239 | 1686 | 179 | 262 | 176 | 1629 | 229 |
| Pos-Diet (1) | 114 | 85 | 350 | 350 | 296 | 126 | 338 | 158 |
| Pre-Diet (2) | 106 | 70 | 170 | 170 | 592 | 198 | 2251 | 357 |
| Post-Diet (2) | 79 | 56 | 113 | 113 | 342 | 109 | 354 | 208 |
| Pre-Diet (3) | 245 | 163 | 1192 | 132 | 782 | 206 | 4406 | 857 |
| Post-Diet (3) | 104 | 63 | 95 | 95 | 227 | 101 | 532 | 189 |
| Pre-TCS (4) | 128 | 89 | 569 | 569 | 134 | 91 | 149 | 95 |
| Post-TCS (4) | 124 | 49 | 320 | 320 | 160 | 92 | 187 | 95 |

*TCS—topical corticosteroids for esophagus
IgA = Immunoglobulin A
IgG4 = Immunoglobulin G4

G4 responses, 20/21 food triggers resulted in the top response values although considerable variability existed among and between patients. Thus, most food triggers were identified by positive responses for both Immunoglobulin A and Immunoglobulin G4. Immunoglobulin A performed the Discussion: Presently, accurate testing for food triggers in eosinophilic oesophagitis is not available, leading to frustration for patients and practitioners (Anyane-Yeboa A, et al. The Role of Allergy Testing in Eosinophilic Esophagitis. Gastroenterol Hepatol (N Y) 2018; 14:463-469; Philpott H, et al. Aliment Pharmacol Ther 2016; 44:223-33; Aceves S S. Clin Gastroenterol Hepatol 2014; 12:1216-23; and Assa'ad A. Ann Allergy Asthma Immunol 2005; 95:309-11). Skin prick testing was found to be less than 20% accurate in a well performed dietary elimination trial (Gonsalves N. Gastrointest Endosc Clin N Am 2018; 28:89-96; and Gonsalves N, et al. Gastroenterology 2012; 142:1451-9). It has been postulated that the oesophagus may develop local immune reactions with B cell switching (Turnbull J L, et al. Aliment Pharmacol Ther 2015; 41:3-25). This theory would explain why skin prick testing may not reflect triggers for the oesophagus. Warners et al tested this hypothesis by performing prick testing to foods in the oesophagi of patients with EoE during endoscopy. This study demonstrated that the oesophagus was capable of immediate type reactions to specific antigens (Warners M J, et al. Gastroenterology 2018; 154:57-60 e2; and Warners MJ, et al. Am J Physiol Gastrointest Liver Physiol 2017; 313:G230-G238). Such esophageal reactions, possibly related to Immunoglobulin E, were different than those identified by skin prick testing. However, it remains unclear whether this localized testing is capable of identifying causative triggers (Blanchard C, et al. J Intern Med 2017; 281:448-457). A prior study in which EoE patients were treated with omalizumab (Xolair) failed to reduce esophageal eosinophilia in EoE, discouraging the belief that Immunoglobulin E reactivity is important in the pathophysiology of EoE (Philpott H, et al. Aliment Pharmacol Ther 2016; 44:223-33). Immunoglobulin G4 is highly unregulated in the esophageal mucosa of EoE and could reflect causal responses to antigens triggering disease (Clayton F, et al. Gastroenterology 2014; 147:602-9). However, several studies found that esophageal tissue homogenates and serum tested for food specific Immunoglobulin G4 did not accurately predict causative antigens (Wright B L, et al. J Allergy Clin Immunol 2016; 138:1190-1192; Bjorksten B, et al. Allergy 1983; 38:119-24; Guhsl E E, et al. Allergy 2015; 70:59-66; McGowan E C, et al. Ann Allergy Asthma Immunol 2019; Pope A E, et al. J Pediatr Gastroenterol Nutr 2019; 68:689-694; and Schuyler A J, et al. J Allergy Clin Immunol 2018; 142:139-148). A recent study combined peripheral CD4+T cell proliferation in combination with esophageal tissue Immunoglobulin G4 food specific detection to direct food elimination. The results led to improvement in patients but few with resolution (McGowan E C, et al. Ann Allergy Asthma Immunol 2019). These results may be influenced by the patchy nature of Immunoglobulin G4 in the mucosa of EoE. Immunoglobulin G4 presence is variable throughout the esophageal mucosa and may not be accurately reflected in the homogenate from a single biopsy. However, immunoglobulin testing may provide answers to food triggers in EoE, especially in light of recent data that has identified food allergens within the mucosa of EoE (Philpott H, Dellon E S. Gastroenterology 2017; 153:605-606).

To perform more extensive surface sampling, the brushings obtained from the diseased oesophagus in patients with EoE were analyzed, and the results suggest that elevated levels of Immunoglobulin A and Immunoglobulin G4 to specific foods are present in esophageal secretions obtained along the esophageal surface. Further, these food specific immunoglobulins identified food triggers in EoE patients with high classification power ranging from 88.2% to 94.1%. In addition, the results show that Immunoglobulin A and Immunoglobulin G4 antibodies are not substantially elevated in normal mucosal secretions in patients with resolved EoE and controls, but, rather, appear to be associated closely with active eosinophilic disease itself. Food specific antibodies are not readily detected once the disease resolves (with topical steroids or diet); note the results in FIGS. 1 and 2 between active and resolved EoE indicating minimal Immunoglobulin A and Immunoglobulin G4 antibody levels for food antigens in the resolved patients. Additionally, it is believed that the locally produced food specific antibodies are not significantly contaminated by plasma or saliva. Thus, esophageal brushings from the diseased oesophagus in EoE contain valuable information and may be useful in identifying the causal antigens. Although 3 patients were followed before and after diet therapy, these data suggest that food specific antibodies appear to decrease when the disease is controlled on diet. However, it remains unclear whether development of food specific antibodies is dependent on active food consumption and/or active disease.

Immunoglobulin A food specific antibodies found along the diseased esophageal lumen appear to differentiate trigger foods (those that cause esophageal inflammation) from non-trigger foods better than Immunoglobulin G4 responses; this may be due to high variability of Immunoglobulin G4 responses in a relatively small cohort. Additionally, Immunoglobulin G4 to foods (especially dairy) is commonly increased in the serum of cohorts both with and without food allergy (Schuyler A J, et al. J Allergy Clin Immunol 2018; 142:139-148). Thus, it is plausible that Immunoglobulin G4 responses may occur without indicating trigger foods. However, interestingly, the Immunoglobulin G4 food specific antibody responses were most strikingly elevated to trigger foods compared to other foods. Overall, Immunoglobulin A response values were less variable upon sampling and significantly higher to the foods implicated in causing EoE compared to foods that did not cause the EoE.

Contamination of the esophageal collections from plasma or saliva was also tested (FIG. 9). The inflamed esophageal lumen may contain proteins from plasma extravasation during inflammation as well as contamination from salivary secretions. Saliva contains abundant Immunoglobulin A and could interfere with the assay. Food specific immunoglobulin expression decreased in the esophageal lumen after resolution of disease regardless of the modality of therapy (proton pump inhibitor, topical steroids, elimination diet) arguing against salivary contamination.

While the study described herein is limited by its small sample size, the results show that patients who have EoE triggered by wheat and dairy are present in adequate numbers in this study for meaningful calculations of diagnostic sensitivity. Furthermore, this study is limited to food-specific Immunoglobulin A and Immunoglobulin G4 and other immunoglobulins were not tested. Total Immunoglobulin A was tested and Immunoglobulin A1 was not differentiated from Immunoglobulin A2. Nonetheless, the initial assay appears to differentiate and identify wheat and dairy triggers as important. EoE patients did appear in general to have more immunoreactivity than controls even for foods not causing the EoE. Immunoglobulin A response values for soy and egg (the non-trigger foods) in EoE patients were not significantly different from controls. However, the Immunoglobulin G4 reactions to these same non-trigger foods were increased in EoE compared to controls. This may relate to the high variability of Immunoglobulin G4 response seen in between EoE patients themselves. Immunoglobulin G4 testing was highly variable within and between patients which made global comparisons between patients difficult for Immunoglobulin G4 responses as compared to Immunoglobulin A.

Immunoglobulin G4 is a known antibody recently identified in EoE. Immunoglobulin G4 has been shown to correlated with histologic features in EoE (Pope A E, et al. J Pediatr Gastroenterol Nutr 2019; 68:689-694; and Rosenberg C E, et al. Allergy 2018; 73:1892-1901). Immunoglobulin A is the most abundant immunoglobulin in mucosa, where it acts as an active barrier through immune exclusion of ingested antigens. Its role in allergy remains unclear. Immunoglobulin A may act as a protective mechanism in EoE, binding allergen prior to infiltration into tissues (Turnbull J L, et al. Aliment Pharmacol Ther 2015; 41:3-25). However, Immunoglobulin A may also contribute to disease pathogenesis as it has been shown to activate eosinophils and induce degranulation (Motegi Y, et al. Int Arch Allergy Immunol 2000;122 Suppl 1:25-7; and Muraki M, et al. Int Arch Allergy Immunol 2011; 154:119-27).

In summary, these findings support the conclusion that measurement of antibodies to foods in brushings from eosinophilic esophagitis can be used to identify food triggers for eosinophilic esophagitis. Further, low antibody response values to foods may serve as a marker of successful EoE treatment. The results described herein suggest that the oesophagus secretes detectable local immunoglobulins to antigens related to disease processes, and the methods disclosed herein can be used as an immunological test for patients with EoE.

Example 2: Specific Production of Antibodies Against Antigens Develops from the Disease Itself Background. Eosinophilic oesophagitis (EoE) is increasingly recognized as a common cause of poor quality of life, dysphagia and food impactions in every age group. Food antigens have been implicated in the etiology and exacerbations of EoE in both pediatric and adult populations as evidenced by resolution of disease after elimination diets.

It has been shown that food specific antibodies are developed from diseased esophagi in eosinophilic esophagitis and can identify foods which are causing the inflammation in the esophagus. It remains unclear whether the food specific antibodies are easily reproducible in areas in disease. Additionally, it has not been determined whether the food specific antibodies differed between areas of disease and areas without disease, arguing a local production of antibodies by the disease itself. Testing was performed on samples twice along the diseased esophageal surface (to demonstrate that the results could be duplicated along the diseased surface). Other testing included comparing reactivities to foods and magnitude of reactions according to whether active disease was present in the tissue (>15 eos/HPF on biopsy).

Methods. The study was designed to test if food specific Immunoglobulin A and Immunoglobulin G4 antibody production (food specific antibody (FSA)-IgA and FSA-IgG4) differed between areas of active and inactive eosinophilic disease. Patients consented to one-time sampling of their oesophagus as they presented for upper endoscopy for dysphagia or monitoring of their known EoE. The esophageal brushing was obtained prior to esophageal biopsies during upper endoscopy. A Cook medical cytobrush (Cook Medical, Indianapolis, IN) was passed through the endoscope and applied to the lumen of the oesophagus and brushed over areas of endoscopically active disease and then over areas of inactive disease if there appeared to be a different expression of disease in the esophagus. Two brushes were applied to active disease if the entire esophagus was involved to determine whether food specific antibody measurements fluctuated within disease or yielded similar, reproducible results. The brush was then removed, and flash frozen at −70° C. until further evaluation. Histopathology (i.e., eosinophil counts) were recorded for each area sampled.

Collection of Esophageal Secretions. The esophageal brushing was obtained prior to esophageal biopsies during upper endoscopy. A Cook medical cytobrush (Cook Medical, Indianapolis, IN) was passed through the endoscope and applied to the lumen of the oesophagus and withdrawn from the distal 5 cm of the oesophagus to the upper oesophagus (approximately 15-20 cm from teeth). The brush was then removed, and flash frozen at −70° C. until further evaluation.

Food-specific antibody testing. Food specific antibody testing was performed as described herein. In brief, brushes were thawed and equilibrated with 1 ml of Phadia diluent solution (Product No. 10-9498-01, Kalamazoo, MI) by immersion for ~30 minutes with occasional shaking. Briefly, 40 μL of diluted secretions was added to the food specific solid phase antigens, referred to as CAPs, followed by washing and addition of Immunoglobulin A/Immunoglobulin G4 antibody conjugates, repeat washing and, lastly, by addition of development solution per protocol. Stop solution was added, and the resulting fluorescence signal was measured (response value). Due to the limitations of measuring concentrations from the 1:50 dilution, response values were measured and reported. Results are listed as response values. For assay validation, low and high range control samples were included in each analysis.

Figures 6A, 6B, 6C, 6D:
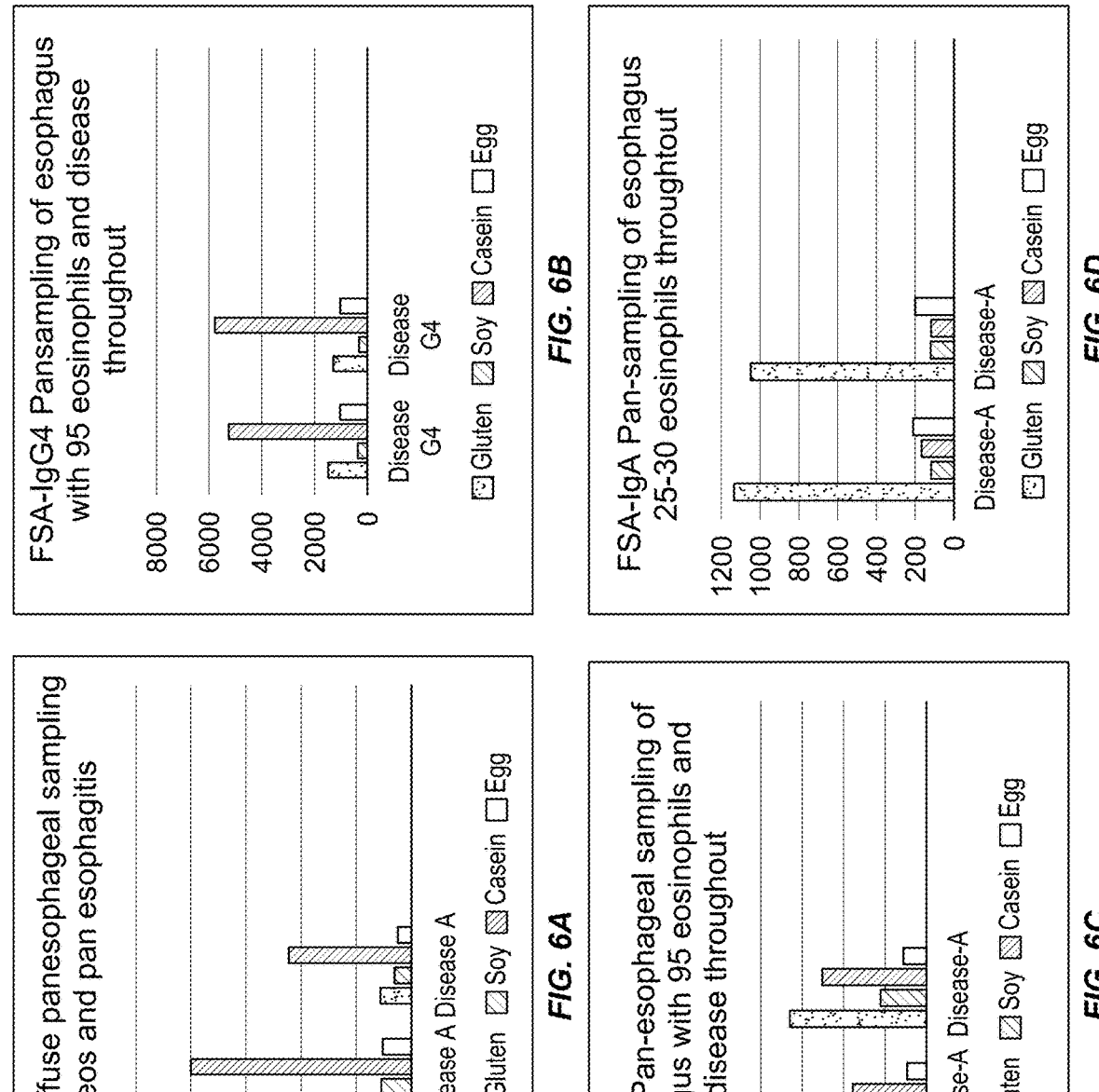
FIGS. 6A-D show uniform sampling performed over areas of esophageal eosinophilia demonstrate similar affinities to specific foods, and that sampling is easily replicated. This demonstrates that the sampling is uniform throughout the diseased areas with similar results on two different brushings.
Figures 7A, 7B, 7C, 7D:
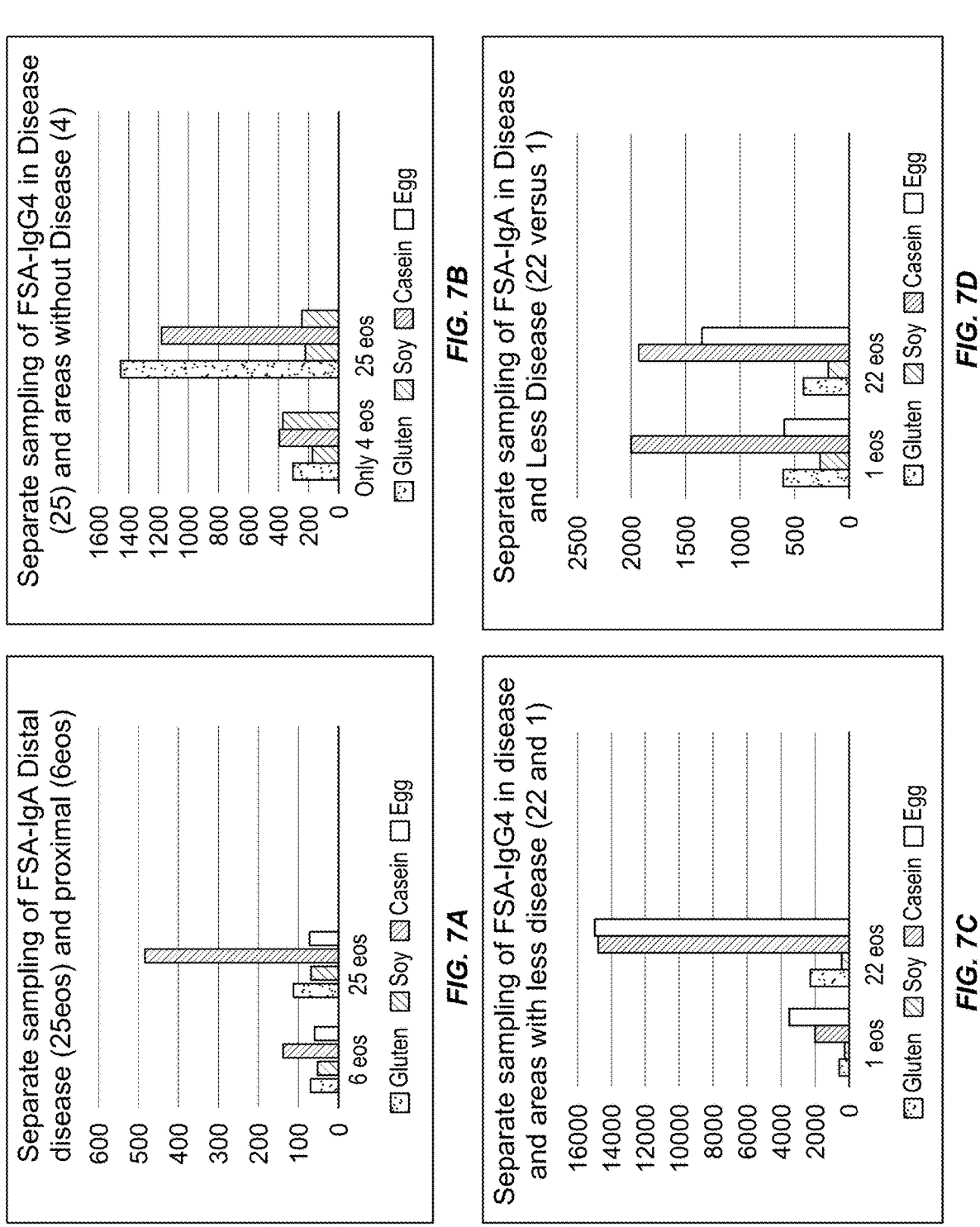
FIGS. 7A-D show the results of samples taken from different areas of the esophagus specifically sampled within an area of disease and then sampled in an area without significant disease. Alterations in the food specific antibody production was seen when the areas with disease are sampled as compared for areas without disease indicating that the active esophageal disease itself is the likely source of the food specific antibodies.

Results. The FIGS. 6 and 7 represent both food specific IgA and IgG4 taken along diseased areas in the esophagus. The graphs represent two different brushing results sampled in areas of active disease in the esophagus. As depicted in the graphs in FIG. 6, the food antibody ratios for food antigens appear similar between each brush per patient. The food specific antibody ratios are relatively stable when taken along areas of disease. In FIG. 7, the two brushes for each patient were taken at different areas: (1) an area of positive disease histologically (>15 eosinophils/HPF) and (2) an area of less disease (less than 7 eosinophils/HPF). In FIG. 7A, the ratio of food specific IgA (FSA-IgA) for casein to other foods is much greater in the area of disease (left) as compared to areas of less disease (right).

In FIG. 7B, IgG4 seems to vary in its affinity for food antigens between the diseased (25 eos) and non-diseased (4 eos) areas, suggesting that it may be directly produced by the disease itself FIG. 7B demonstrates dramatic increases in IgG4 for casein and egg in areas of disease (22 eos) as compared to those areas without disease (1 eos). FIG. 7D demonstrates some variability of immunoglobulin A egg between areas of disease (22 eos) and areas without disease (1 eos). IgA appears to be less variable in its affinity for food antigens but still varies in its presentation depending upon whether disease is present or absent.

These results suggest that IgA may be more indicative of food triggers even in areas without disease. IgG4 appears to change remarkably depending upon whether disease is present or absent. IgA fluctuates in the intensity of responses as well indicating that the immunoglobulin may be produced by the disease itself and not the mucosa.

In conclusion, food specific antibody testing is reproducible when sampled directly from areas of disease in patients with eosinophilic esophagitis. However, it appears that results from both immunoglobulin A and immunoglobulin G4 antigen testing vary according to whether the sampling occurs in diseased or healthy tissue. This suggests that the specific production of antibodies against antigens develops from the disease itself and is not a reflection of routine mucosal responses. To obtain accurate food antigen testing, one must ensure the food specific antibodies are collected from the diseased tissues.

Example 3: Protein Biomarkers in Diseased Esophageal Secretions are a Feasible Low-Cost and Non-Invasive Diagnostic Modality for Eosinophilic Esophagitis Non-invasive diagnostic biomarkers are needed for EoE.

Introduction. Eosinophilic esophagitis (EoE) is a chronic inflammatory condition governed by a form of non-IgE hypersensitivity. Recent literature shows rapidly rising EoE incidence among children and adults.(J Robson, et al. Clinical Gastroenterology and Hepatology, 17(1):107-114.e1, January 2019). While EoE symptoms often improve with treatment, disease activity may persist, and can contribute to esophageal fibrostenosis (E S Dellon, et al. Gastrointestinal Endoscopy, 79(4):577-585.e4, 2014).

Non-invasive biomarkers to track EoE activity in response to treatment are not currently applied in clinical practice. Therefore, patients are committed to frequent endoscopy with biopsy. Endoscopy requires sedation, carries a procedural risk, and is the driver of the estimated $1.4 billion in annual EoE-attributable healthcare costs in the US (E T Jensen, et al. The American journal of gastroenterology, 110(5):626-632, May 2015). The onus of endoscopy likely leads to substantial non-adherence with recommended EoE disease surveillance. Diagnostic and tracking modalities for EoE that are less expensive and less invasive are needed.

Recent studies have used RNA-sequence analysis and machine learning to create EoE diagnostic tools and identify specific EoE phenotypes (B F Sallis, et al. The Journal of allergy and clinical immunology, 141(4):1354-1364.e9, April 2018). Described herein are data identifying EoE genes using machine learning algorithms, which specifically targeted EoE genes with protein transcription products. Esophageal secretions can be reliably obtained with the patient awake, at substantially lower cost and risk to the patient compared to endoscopy (H Saffari, et al. The American journal of gastroenterology, 111(7):933-939, July 2016). It was assessed whether expressed proteins could be collected in esophageal luminal secretions and used to differentiate between patients with active EoE, treatment-resolved EoE, and controls.

Methods. Potential Biomarker Identification via Transcriptome Analysis. In order to discover candidate biomarkers for EoE in a high-throughput manner, RNA-sequence data was analyzed from 14 EoE patients and 14 controls.[6] Decision trees, a type of machine learning algorithm, were fitted to gene expression values, measured in transcripts-per-million reads (TPM). Five-fold cross validation was used to assess the diagnostic accuracy of each gene. Genes were designated as candidate biomarkers if the following criteria was met: diagnostic accuracy was 100% and the gene encodes a secreted protein product that can be measured using a commercially-available assay.

Biomarker Validation in Esophageal Secretions. The diagnostic accuracy of candidate biomarkers was assessed at the protein level in esophageal secretions. Esophageal secretions from 5 patients with active EoE (EoE), 6 with patients with treatment-resolved EoE (RES), and 6 controls (CTRL) were obtained using an endoscopic cytobrush. For each sample, protein expression was assayed using a Luminex 23-cytokine panel.

Figures 8A, 8B, 8C:
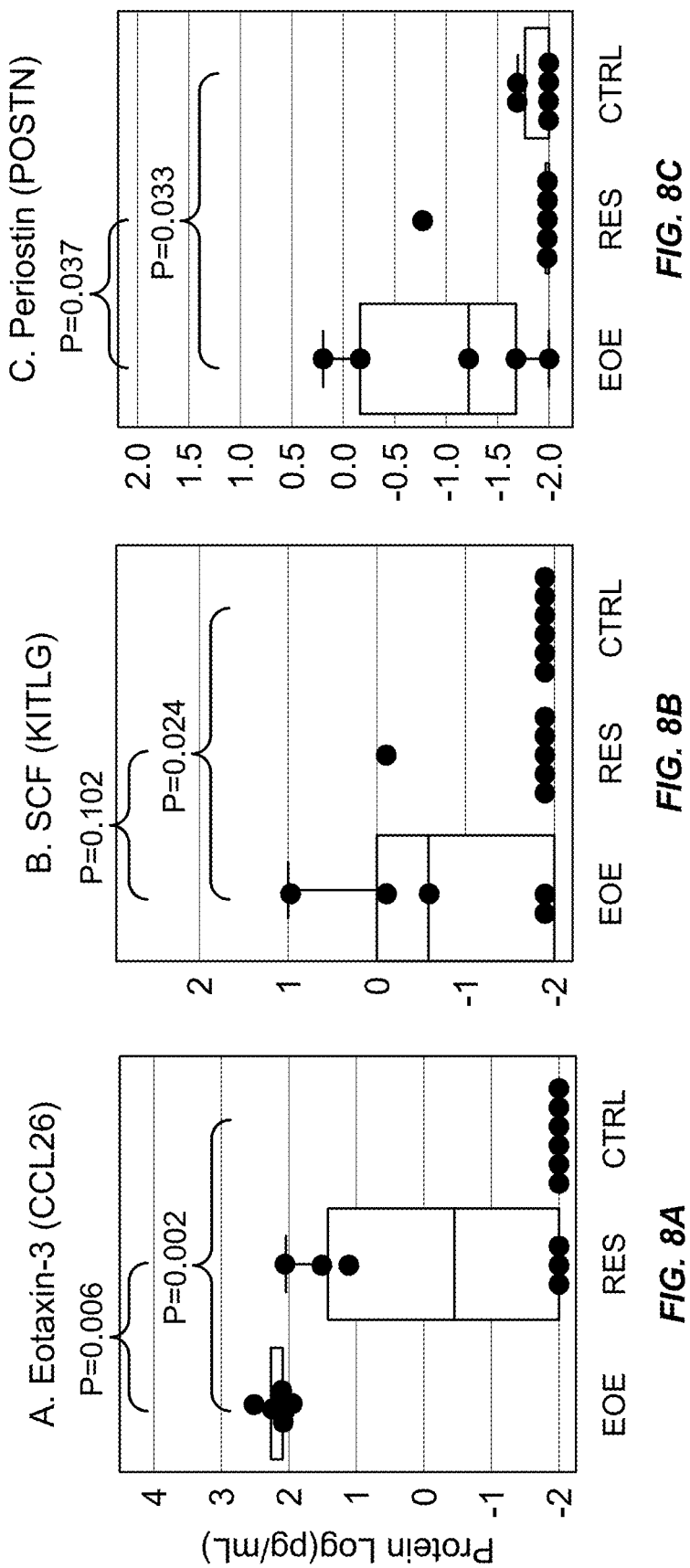
FIGS. 8A-C show protein expression of select biomarkers in esophageal secretions.

Results. Genes encoding protein biomarkers were identified via transcriptome analysis, including CCL26, which encodes eotaxin-3, KITLG, which encodes stem cell factor (SCF), and POSTN, which encodes periostin (FIGS. 8A-8C). Eotaxin-3 was highly expressed in the active EoE cases compared to controls and was more highly expressed in active EoE compared to treatment-resolved EoE.

Example 4: Food Specific Antibodies in the Small Bowel: Association with Trigger Foods in Eosinophilic Esophagitis (EoE)

Figure 10:
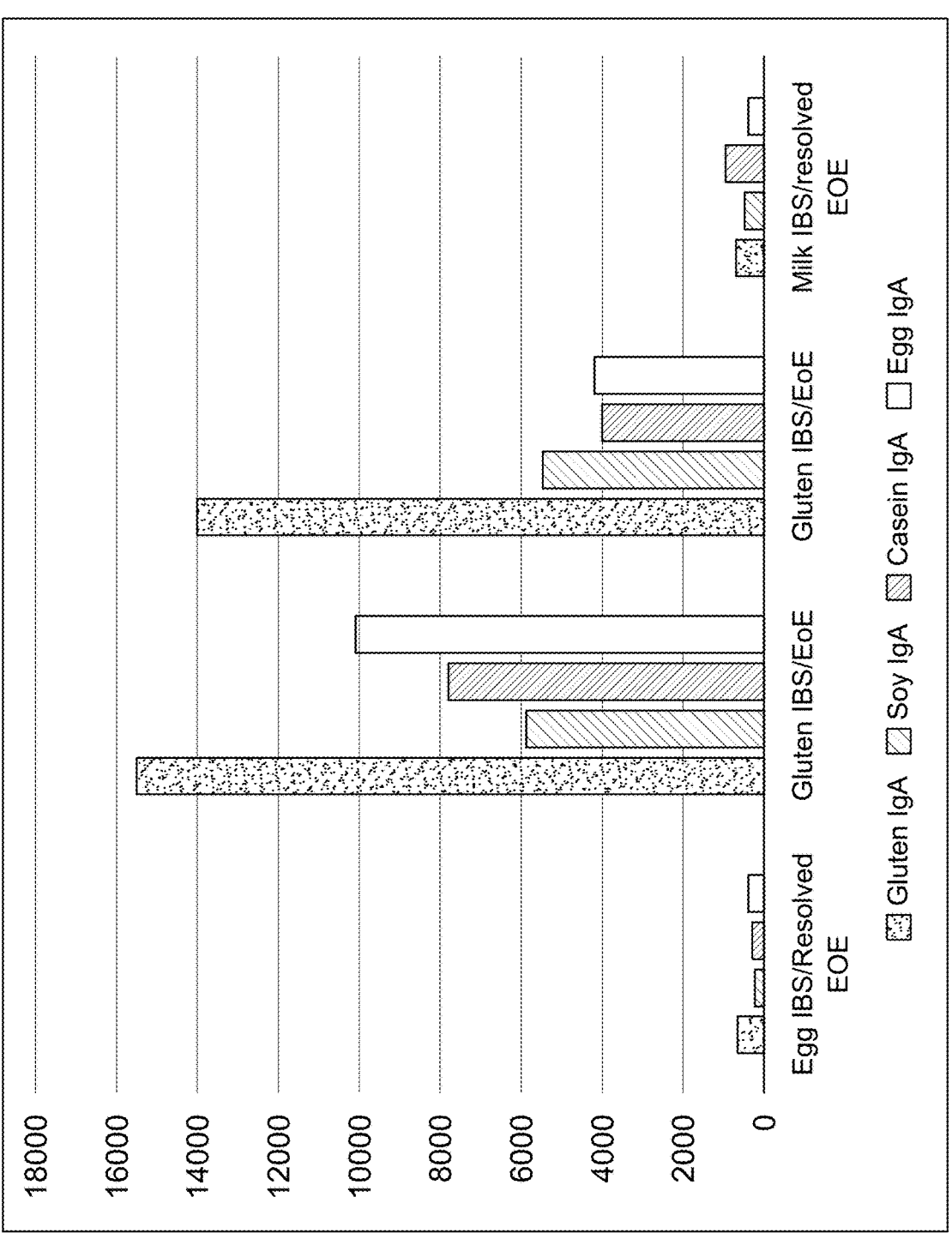
FIG. 10 shows small bowel relative values for food specific IgA for 4 patients with abdominal pain and discomfort.

Small bowel relative values for food specific IgA for 4 patients with abdominal pain and discomfort are shown in FIG. 10. Samples were obtained from patients with irritable bowel syndrome (IBS). More specifically, samples were obtained from the small bowel. The two with resolved eosinophilic esophagitis appear to have lower reactivities in the small bowel. One with resolved EoE (far left) noticed his abdominal pain recurred when adding in eggs as part of his elimination diet. His bowel sampling suggests that eggs are a stronger reaction. The other (far right) noticed resolution of 80% of her abdominal pain when she removed milk from her diet. Her small bowel demonstrated higher values of food specific IgA for casein. The two in the middle have active EOE and abdominal pain (one with right upper quadrant pain and the other with non specific "IBS"). Both have increased food specific antibodies to foods compared to those who resolved their EOE ang both demonstrate higher levels of IgA against gluten. Others without abdominal discomfort have lower values for foods than even the resolved EOE.

We claim:

1. A method of detecting the binding of one or more food specific immunoglobulin (Ig) antibodies to one or more food antigens in an esophageal secretion sample, the method comprising: contacting the esophageal secretion sample obtained from a subject with one or more food antigens and detecting the binding of the one or more food specific Ig antibodies to the one or more food antigens.

2. The method of claim 1, wherein the one or more food antigens are immobilized on a solid support.

3. The method of claim 1, wherein the esophageal secretion sample is obtained before the subject consumes a food comprising one or more of the food antigens.

4. The method of claim 1, wherein the esophageal secretion sample is obtained after the subject consumes a food comprising one or more of the food antigens.

5. The method of claim 1, further comprising comparing the binding of the one or more food specific Ig antibodies to the one or more food antigens in the esophageal secretion sample obtained prior to the subject consuming the food comprising the one or more of the food antigens to the esophageal secretion sample obtained after the subject consumed the food comprising the one or more of the food antigens.

6. A method of treating a subject with active or inactive eosinophilic esophagitis (EoE), the method comprising:
   a) detecting the presence of or level of one or more immunoglobulin (Ig) antibodies bound to the one or more food antigens in an esophageal secretion sample;
   b) comparing the level of the one or more Ig antibodies bound to the one or more food antigens in the esophageal secretion sample to the level of one or more Ig antibodies bound to the one or more food antigens in a reference sample;

c) determining that the level of the one or more Ig antibodies bound to a food specific antigen is higher in the esophageal secretion sample compared to the level of the one or more Ig antibodies bound to the same food specific antigen in a reference sample; and d) withdrawing one or more food types that correlate to the food antigen bound to the one or more Ig antibodies that is higher in the esophageal secretion sample of the subject, thereby treating the subject.

7. The method of claim 6, further comprising detecting EoE in the subject prior to the detecting step.

8. The method of claim 7, wherein EoE is detected in the subject by detecting an eosinophil granule protein in the mucosal tissue of the esophagus in the subject, comprising administering to the subject radiolabeled heparin under conditions wherein the radiolabeled heparin binds to an eosinophil granule protein to form a radiolabeled heparin/eosinophil granule protein complex, and detecting the radiolabeled heparin/eosinophil granule protein complex in the mucosal tissue of the esophagus, whereby detecting the radiolabeled heparin/eosinophil granule protein complex in the mucosal tissue of the esophagus detects eosinophilic esophagitis in the subject.

9. The method of claim 6, further comprising obtaining or having obtained the esophageal secretion sample from a subject.

10. The method of claim 9, wherein the subject has active eosinophilic esophagitis.

11. The method of claim 9, wherein the subject has resolved eosinophilic esophagitis.

12. The method of claim 9, wherein the subject has at least one symptom of esophagitis.

13. The method of claim 9, wherein the subject has irritable bowel syndrome.

14. The method of claim 6, wherein the sample comprises one or more food-specific Ig antibodies.

15. The method of claim 1, wherein the one or more food-specific Ig antibodies are IgG, IgA, IgM, IgD, IgE or a combination thereof.

16. The method of claim 1, wherein the one or more food antigens are wheat f1, soybean f14, casein f78, eggf245, or a combination thereof.

17. The method of claim 1, wherein the level of the one or more food specific Ig antibodies bound to the one or more food antigens are higher in the esophageal secretion sample compared to the level of the one or more food specific Ig antibodies bound to the one or more food antigens in a reference sample, indicating a food specific immune response.

* * * * *